US011964005B2

(12) United States Patent
Harris et al.

(10) Patent No.: US 11,964,005 B2
(45) Date of Patent: Apr. 23, 2024

(54) METHODS OF TREATING ATOPIC DERMATITIS

(71) Applicant: Receptos LLC, Princeton, NJ (US)

(72) Inventors: Sarah Harris, Princeton, NJ (US); Erin Babcock, San Diego, CA (US); Cristian Rodriguez, La Jolla, CA (US)

(73) Assignee: Receptos, LLC, Princeton, NJ (US)

( * ) Notice: Subject to any disclaimer, the term of this patent is extended or adjusted under 35 U.S.C. 154(b) by 0 days.

(21) Appl. No.: 17/696,028

(22) Filed: Mar. 16, 2022

(65) Prior Publication Data

US 2022/0305104 A1    Sep. 29, 2022

Related U.S. Application Data

(60) Provisional application No. 63/162,101, filed on Mar. 17, 2021.

(51) Int. Cl.
A61K 39/00 (2006.01)
A61K 9/00 (2006.01)
A61P 17/04 (2006.01)

(52) U.S. Cl.
CPC .... *A61K 39/001104* (2018.08); *A61K 9/0019* (2013.01); *A61P 17/04* (2018.01)

(58) Field of Classification Search
CPC .................................................. A61K 39/3955
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,530,101 A | 6/1996 | Queen et al. | |
| 5,565,332 A | 10/1996 | Hogenboom et al. | |
| 5,585,089 A | 12/1996 | Queen et al. | |
| 5,693,762 A | 12/1997 | Queen et al. | |
| 5,714,352 A | 2/1998 | Jakobovits | |
| 5,723,323 A | 3/1998 | Kauffman et al. | |
| 5,763,192 A | 6/1998 | Kauffman et al. | |
| 5,766,886 A | 6/1998 | Studnicka et al. | |
| 5,807,715 A | 9/1998 | Morrison et al. | |
| 5,814,476 A | 9/1998 | Kauffman et al. | |
| 5,817,483 A | 10/1998 | Kauffman et al. | |
| 5,824,514 A | 10/1998 | Kauffman et al. | |
| 5,976,862 A | 11/1999 | Kauffman et al. | |
| 6,180,370 B1 | 1/2001 | Queen et al. | |
| 6,204,023 B1 | 3/2001 | Robinson et al. | |
| 6,737,056 B1* | 5/2004 | Presta | C07K 16/18 530/387.3 |
| 7,915,388 B2 | 3/2011 | Wu et al. | |
| 2012/0097565 A1 | 4/2012 | Dix et al. | |
| 2014/0341913 A1 | 11/2014 | Tripp | |
| 2015/0017176 A1 | 1/2015 | Kostic et al. | |
| 2016/0002326 A1* | 1/2016 | Cuff | C07K 16/244 424/136.1 |

FOREIGN PATENT DOCUMENTS

| | | |
|---|---|---|
| EP | 0229246 | 1/1986 |
| EP | 0239400 | 9/1987 |
| EP | 0519596 | 12/1992 |
| EP | 0592106 | 4/1994 |
| WO | 90/05144 | 5/1990 |
| WO | 90/05370 | 5/1990 |
| WO | 90/14330 | 11/1990 |
| WO | 90/14424 | 11/1990 |
| WO | 90/14443 | 11/1990 |
| WO | 91/09967 | 7/1991 |
| WO | 92/01047 | 1/1992 |
| WO | 92/03461 | 3/1992 |
| WO | 92/11272 | 7/1992 |
| WO | 93/06213 | 4/1993 |
| WO | 94/18219 | 8/1994 |
| WO | 97/20032 | 6/1997 |
| WO | 99/06834 | 2/1999 |
| WO | 01/83525 | 11/2001 |
| WO | 2005/007699 | 1/2005 |
| WO | 2005/123126 | 12/2005 |
| WO | 2018057849 | 3/2018 |

OTHER PUBLICATIONS

Sidbury, Robert, et al., "Guidelines of Care for the Management of Atopic Dermatitis, Journal of the American Academy of Dermatology", Aug. 2014, vol. 71, No. 2, pp. 327-349.
Simpson, Eric, et al., "Atopic Dermatitis: Emerging Therapies", Seminars in Cutaneous Medicine and Surgery, Sep. 2017, vol. 36, pp. 124-130.
Simpson, E.L., et al., "Two Phase 3 Trials of Dupilumab Versus Placebo in Atopic Dermatitis", The New England Journal of Medicine, Dec. 15, 2016, vol. 375, No. 24, pp. 2335-2348.
Simpson, E.L., et al., Protocol, "A Phase 3 Confirmatory Study Investigating the Efficacy and Safety of Dupilumab Monotherapy Administered to Adult Patients with Moderate-to-Severe Atopic Dermatitis", New England Journal of Medicine, 2016, pp. 1-88.
Simpson, E.L., et al., Supplementary Amendment , "A Phase 3 Confirmatory Study Investigating the Efficacy and Safety of Dupilumab Monotherapy Administered to Adult Patients with Moderate-to-Severe Atopic Dermatitis", New England Journal of Medicine, 2016, pp. 1-88.
Simpson, Eric, "Two Randomized Trials of Dupilumab Versus Placebo in Atopic Dermatitis", International Committee of Medical Journal Editors, Aug. 12, 2016, pp. 1-86.
Sims, M.J., et al., "A Humanized CD 18 Antibody Can Block Function Without Cell Destruction", The Journal of Immunology, 1993, vol. 151, pp. 2296-2308.

(Continued)

*Primary Examiner* — Prema M Mertz
(74) *Attorney, Agent, or Firm* — McCarter & English, LLP

(57) ABSTRACT

The present disclosure is directed to methods of treating atopic dermatitis comprising administering to a subject in need thereof a therapeutically effective amount of an anti-IL-13 antibody, or antigen binding fragment thereof, thereby treating atopic dermatitis in the subject.

9 Claims, No Drawings
Specification includes a Sequence Listing.

(56) References Cited

OTHER PUBLICATIONS

Studnicka, Gary M., et al., "Human-Engineered Monoclonal Antibodies Retain Full Specific Binding Activity by Preserving Non-CDR Complementarity-Modulating Residues", Protein Engineering, 1994, vol. 7, No. 6, pp. 805-814.
Tada, Joji, "Diagnostic Standard for Atopic Dermatitis", English Version of a Paper Originally Published in the Journal of the Japan Medical Association, 2001, vol. 126, No. 1, pp. 1-6.
Takeda, Shun-ichi, et al., "Construction of Chimaeric Processed Immunoglobulin Genes Containing Mouse Variable and Human Constant Region Sequences", Nature, Apr. 4, 1985, vol. 314, pp. 452-454.
Taylor, Lisa D., et al., "A Transgenic Mouse that Expresses a Diversity of Human Sequence Heavy and Light Chain Immunoglobulins", Nucleic Acids Research, 1992, vol. 20, No. 23, pp. 6287-6295.
Thaci, Diamant, et al., "Efficacy and Safety of Dupilumab in adults with Moderate-to-Severe Atopic Dermatitis Inadequately Controlled by Topical Treatments: A Randomised, Placebo-Controlled, Dose-Ranging Phase 2b Trial", The Lancet, Jan. 2, 2016, vol. 387, pp. 40-52.
Tsoi, Lam C., et al., "Atopic Dermatitis Is an IL-13-Dominant Disease with Greater Molecular Heterogeneity Compared to Psoriasis", Journal of Investigative Dermatology, 2019, vol. 139, pp. 1480-1489.
Ulzii, Dugarmaa, et al., "Scratching Counteracts IL-13 Signaling by Upregulating the Decoy Receptor IL-13 Rα2 in Keratinocytes", International Journal of Molecular Sciences, 2019, vol. 20, No. 3324, pp. 1-12.
Verhoeyen, Martine, et al., "Reshaping Human Antibodies: Grafting an Antilysozyme Activity", Science, Mar. 25, 1988, vol. 239, pp. 1534-1536.
Vladich, Frank D., et al., "IL-13 R130Q, a Common Variant Associated with Allergy and Asthma, Enhances Effector Mechanisms Essential for Human Allergic Inflammation", The Journal of Clinical Investigation, Mar. 2005, vol. 115, No. 3, pp. 747-754.
Ward, Sally E., "Binding Activities of a Repertoire of Single Immunoglobulin Variable Domains Secreted from *Escherichia coli*", Nature, Oct. 12, 1989, vol. 341, pp. 544-546.
Wu, George Y., et al., "Receptor-Mediated in Vitro Gene Transformation by a Soluble DNA Carrier System", The Journal of Biological Chemistry, Apr. 5, 1987, vol. 262, No. 10, pp. 4429-4432.
Wynn, Thomas A., et al., "IL-13 Effector Functions", Annual Review of Immunology, 2003, vol. 21, pp. 425-456.
Ying, H., et al., "ABT-308, A Highly Potent Anti-IL-13 Therapeutic Antibody for the Treatment of Human Asthma", Diagnosis and Treatment of Asthma, 2010, Abstract, 1 Page.
Alexander, Helen, et al. "Novel Systemic Therapies in Atopic Dermatitis: What Do We Need to Fulfil the Promise of a Treatment Revolution?", F1000 Research, Faculty Rev, 132, Mar. 31, 2022, pp. 1-15.
Ariens, Lieneke, F.M., et al., "Dupilumab in Atopic Dermatitis: Rationale, Latest Evidence and Place in Therapy", Therapeutic Advances in Chronic Disease, 2018, vol. 9, No. 9, pp. 159-170.
Azzazy, Hassan, et al., "Phage Display Technology: Clinical Applications and Recent Innovations", Clinical Biochemistry, 2002, vol. 35, pp. 425-445.
Bieber, Thomas, "Interleukin-13: Targeting an Underestimated Cytokine in Atopic Dermatitis", Allergy, 2020, vol. 75, pp. 54-62.
Bird, Robert E., et al., "Single-Chain Antigen-Binding Proteins", Science, Oct. 21, 1988, vol. 242, pp. 423-426.
Boguniewicz, Mark, et al., "Atopic Dermatitis: A Disease of Altered Skin Barrier and Immune Dysregulation", Immunological Reviews, 2011, vol. 242, pp. 233-246.
Brightling, C.E., et al., "Interleukin-13: Prospects for New Treatments", Clinical Exp. Allergy, 2010, vol. 40, pp. 42-49.

Carter, Paul, et al., "Humanization of an Anti-p185 HER2 Antibody for Human Cancer Therapy", Proceedings of the National Academy of Sciences of the United States of America, May 1992, vol. 89, pp. 4285-4289.
Chiesa, Zelma C., et al., "Atopic Dermatitis in America Study: A Cross-Sectional Study Examining the Prevalence and Disease Burden of Atopic Dermatitis in the US Adult Population", Journal of Investigative Dermatology, 2019, vol. 139, pp. 583-590.
Chothia, Cyrus, et al., "Canonical Structures for the Hypervariable Regions of Immunoglobulins", Journal of Molecular Biology, 1987, vol. 196, pp. 901-917.
Chothia, Cyrus, et al., "Conformation of Immunoglobulin Hypervariable Regions", Nature, Dec. 1989, vol. 342, pp. 877-883.
Czarnowicki, Tali, et al., "Atopic Dermatitis Endotypes and Implications for Targeted Therapeutics", The Journal of Allergy and Clinical Immunology, 2019, vol. 143, pp. 1-11.
Eichenfield, Lawrence F., et al., Costs and Treatment Patterns Among Patients with Atopic Dermatitis Using Advanced Therapies in the United States: Analysis of a Retrospective Claims Database, Dermatology Therapy, 2020, vol. 10, pp. 791-806.
Esaki, Hitokazu, et al., "Identification of Novel Immune and Barrier Genes in Atopic Dermatitis by Means of Laser Capture Microdissection", The Journal of Allergy and Clinical Immunology, 2015, vol. 135, pp. 153-163.
Gavilondo, Jorge V., et al., "Antibody Engineering at the Millennium", BioTechniques, 2000, vol. 29, No. 1, pp. 128-145.
Gillies, Stephen D., et al., "High-Level Expression of Chimeric Antibodies Using Adapted cDNA Variable Region Cassettes", Journal of Immunological Methods, 1989, vol. 125, pp. 191-202.
Goodson, J. Max, "Chapter 6—Dental Applications", Medical Applications of Controlled Release, 1984, vol. 2, pp. 115-138.
Hezareh, Marjan, et al., "Effector Function Activities of a Panel of Mutants of a Broadly Neutralizing Antibody Against Human Immunodeficiency Virus Type 1", Journal of Virology, Dec. 2001, vol. 75, No. 24, pp. 12161-12168.
Holliger, Philipp, et al., ""Diabodies": Small Bivalent and Bispecific Antibody Fragments", Proceedings of the National Academy of Sciences of the United States of America, Jul. 1993, vol. 90, pp. 6444-6448.
Hoogenboom, Hennie R., et al., "Natural and Designer Binding Sites Made by Phage Display Technology", Immunology Today, 2000, vol. 21, pp. 371-378.
Hogenboom, Hennie R., "Designing and Optimizing Library Selection Strategies for Generating High-Affinity Antibodies", TibTech, Feb. 1997, vol. 15, pp. 6 2-70.
Howells, L., et al., "How Should Minimally Important Change Scores for the Patient-Oriented Eczema Measure be Interpreted? A Validation Using Varied Methods", British Journal of Dermatology, 2018, vol. 178, pp. 1135-1142.
Huston, James S., et al., "Protein Engineering of Antibody Binding Sites: Recovery of Specific Activity in an Anti-Digoxin Single-Chain Fv Analogue Produced in *Escherichia coli*", Proceedings of the National Academy of Sciences of the United States of America, Aug. 1988, vol. 85, pp. 5879-5883.
Johnsson, Bo, et al., "Immobilization of Proteins to a Carboxymethyldextran-Modified Gold Surface for Biospecific Interaction Analysis in Surface Plasmon Resonance Sensors", Analytical Biochemistry, 1991, vol. 198, pp. 268-277.
Johnsson, Bo, et al., "Comparison of Methods for Immobilization to Carboxymethyl Dextran Sensor Surfaces by Analysis of the Specific Activity of Monoclonal Antibodies", Journal of Molecular Recognition, 1995, vol. 8, pp. 125-131.
Jones, Peter T., et al., "Replacing the Complementarity-Determining Regions in a Human Antibody with those from a Mouse", Nature, May 29, 1986, vol. 321, pp. 522-525.
Jonsson, U., et al., "Introducing a Biosensor Based Technology for Real-Time Biospecific Interaction Analysis", Advances in Clinical Biology, 1993, vol. 51, pp. 19-26.
Jonsson, U., et al., "Real-Time Biospecific Interaction Analysis Using Surface Plasmon Resonance and a Sensor Chip Technology", Biotechniques, 1991, vol. 11, No. 5, pp. 620-627.

(56) References Cited

OTHER PUBLICATIONS

Kabat, Elvin A., "Attempts to Locate Complementarity-Determining Residues in the Variable Positions of Light and Heavy Chains", Annals of the New York Academy of Sciences, 1971, vol. 190, pp. 382-393.
Kellermann, Sirid-Aimee, et al., "Antibody Discovery: The Use of Transgenic Mice to Generate Human Monoclonal Antibodies for Therapeutics", Current Opinion In Biotechnology, 2002, vol. 13, pp. 593-597.
Kipriyanov, Sergey M., et al., "Single-Chain Antibody Streptavidin Fusions: Tetrameric Bifunctional scFv-Complexes with Biotin Binding Activity and Enhanced Affinity to Antigen", Human Antibodies, Hybridomas, 1995, vol. 6, No. 3, pp. 93-101.
Kipriyanov, Sergey M., et al., "Recombinant Single-Chain Fv Fragments Carrying C-Terminal Cysteine Residues: Production of Bivalent and Biotinylated Miniantibodies", Molecular Immunology, 1994, vol. 31, No. 14, pp. 1047-1058.
Langer, Robert "New Methods of Drug Delivery", Science, Sep. 28, 1990, vol. 249, pp. 1527-1533.
Little, M., et al., "Of Mice and Men: Hybridoma and Recombinant Antibodies", Immunology Today, Aug. 2002, vol. 21, No. 8, pp. 364-370.
MacCallum, Robert M., et al., "Antibody-Antigen Interactions: Contact Analysis and Binding Site Topography", Journal of Molecular Biology, 1996, vol. 262, pp. 732-745.
Marchalonis, John J., et al., "Evolutionary Factors in the Emergence of the Combinatorial Germline Antibody Repertoire", Advances in Experimental Medicine and Biology, 2001, vol. 484 pp. 13-30.
Morrison, Sherie L., et al., "Chimeric Human Antibody Molecules: Mouse Antigen-Binding Domains with Human Constant Region Domains", Proceedings of the National Academy of Sciences of the United States of America, Nov. 1984, vol. 81, pp. 6851-6855.
Morrison, Sherie L., "Transfectomas Provide Novel Chimeric Antibodies", Science, 1985, vol. 229, pp. 1202-1207.
Moy, Franklin J., et al., "Solution Structure of Human IL-13 and Implication for Receptor Binding", Journal of Molecular Biology, 2001, vol. 310, pp. 219-230.
Muraro, Antonella, et al., "Precision Medicine in Patients with Allergic Diseases: Airway Diseases and Atopic Dermatitis—Practall Document of the European Academy of Allergy and Clinical Immunology and the American Adaceny of Allergy, Asthma and Immunology", The Journal of Allergy and Clinical Immunology, May 2016, pp. 1347-1358.
Neuberger, Michael S., et al., "Recombinant Antibodies Possessing Novel Effector Functions", Nature, Dec. 13, 1984, vol. 312, pp. 604-608.
Oi, Vernon T., et al., "Chimeric Antibodies", BioTechniques, 1986, vol. 4, No. 3, pp. 214-221.

Padlan, Eduardo, A., et al., "Identification of Specificity—Determining Residues in Antibodies", The FASEB Journal, Jan. 1995, vol. 9, pp. 133-139.
Padlan, Eduardo A., "A Possible Procedure for Reducing the Immunogenicity of Antibody Variable Domains while Preserving their Ligand-Binding Properties", Molecular Immunology, 1991, vol. 28, No. 4/5, pp. 489-498.
Poljak, Roberto J., "Production and Structure of Diabodies", Structure, Dec. 15, 1994, vol. 2, pp. 1121-1123.
Powell, Michael F., et al., "Compendium of Excipients for Parenteral Formulations", PDA Journal of Pharmaceutical Science and Technology, 1998, vol. 52, pp. 238-311.
Presta, L.G., et al., "Humanization of an Antibody Directed Against IgE", The Journal of Immunology, 1993, vol. 151, pp. 2623-2632.
Roguska, Michael A.. et al., "Humanization of Murine Monoclonal Antibodies Through Variable Domain Resurfacing", Proceedings of the National Academy of Sciences of the United States of America, Feb. 1994, vol. 91, pp. 969-973.
Schneider, Lynda, et al., "Atopic Dermatitis: A Practice Parameter Update 2012", The Journal of Allergy and Clinical Immunology, Feb. 2013, vol. 131, No. 2, pp. 295-299 and 299.e1-299-e.27.
Shapiro, Gary S., et al., "DNA Target Motifs of Somatic Mutagenesis in Antibody Genes", Critical Reviews in Immunology, 2002, vol. 22, No. 3, pp. 183-200.
International Search Report based on co-pending PCT International Application No. PCT/US2022/020518, dated Jun. 13, 2022; pp. 1-7.
Written Opinion based on co-pending PCT International Application No. PCT/US2022/020518, dated Jun. 13, 2022; pp. 1-7.
Anonymous: "NCT04800315, A Phase 2, Multicenter, Global, Randomized, Double-blind, Placebo-controlled, Parallel-group Study to Evaulate the : Cendakimab (CC-93538) in Adult Subjects with Moderate to Severe Atopic Dermatitis", ClinicalTrials.gov, Mar. 16, 2021, pp. 1-13.
Guttman, Yassky E., et al., "Tralokinumab Phase 2b Study: Effects of the Anti-Interleukin-13 Monoclonal Antibody on Staph. Aureus Skin Colonisation and Systemic Levels of Inflammatory Biomarkers in Patients with Atopic Dermatitis", Database EM Base, Jun. 11, 2019, Journal Conference Abstract, pp. 1-2.
Wollenberg, Andreas, et al., "A Phase 2b Dose-Ranging Efficacy and Safety Study of Tralokinumab in Adult Patients with Moderate to Severe Atopic Dermatitis", Journal of the American Academy of Dermatology (4496), Jun. 1, 2017, vol. 76, No. 1, p. 1.
Loh, Tiffany Y., et al. "Therapeutic Potential of Lebrikizumab in the Treatment of Atopic Dermatitis", Journal of Asthma and Allergy, Feb. 11, 2020, vol. 13, pp. 109-114.
Simpson, Eric L., et al., "Efficacy and Safety of Lebrikizumab (an anti-IL-13 monoclonal antibody) in Adults with Moderate-to-Severe Atopic Dermatitis Inadequately Controlled by Topical Corticosteroids: A Randomized, Placebo-Controlled Phase II Trial (TREBLE)", Journal of the American Academy of Dermatology, May 1, 2018, vol. 78, No. 1, pp. 863-871.e11.

\* cited by examiner

METHODS OF TREATING ATOPIC DERMATITIS

CROSS-REFERENCE TO RELATED APPLICATION

This application claims the benefit of Provisional U.S. Patent Application No. 63/162,101, filed Mar. 17, 2021, which is incorporated herein, in its entirety, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 127754058018SEQUENCELISTING.txt. The size of the text file is 12 KB, and the text file was created on Mar. 16, 2022.

FIELD

The present disclosure relates to the use of anti-IL-13 antibodies to treat atopic dermatitis in subjects in need thereof.

BACKGROUND

Atopic dermatitis (AD) is a common and chronic inflammatory skin disorder that affects a broad demographic, with an increasing prevalence worldwide. Although reported prevalence rates of AD vary, it is estimated that AD affects between 3-10% of the US population, and worldwide, AD affects up to 20% of children and 3% of adults (Sacotte et al., Clin. Dermatol. 36:595-605 (2018)). Of those affected, about 40% have moderate to severe disease, consistent with high disease burden, resulting in a significant impact on a patient's quality of life (Chiesa et al., J. Invest. Dermatol. 139:583-90 (2019)). AD is associated with increased anxiety, depression, sleep disorders, reduced productivity, and impaired activity, all of approximately equivalent magnitude to those observed in psoriasis (Eckert et al., J. Am. Acad. Dermatol. 78:54-61 (2017)). A recent study performed in the United States focused on the costs and treatment patterns associated with more advanced therapies, such as dupilumab (anti-IL-4R monoclonal antibody), systemic corticosteroids, systemic immunosuppressants, and phototherapy. This study estimated that almost two-thirds of patients with moderate to severe AD who initiated systemic immunosuppressants, and a quarter of those who initiated dupilumab, discontinued treatment within 6 months. These patients represent a significant burden to the healthcare system, with costs in the United States representing approximately $20,000 per patient per year (Eichenfield et al., Dermatol. Ther. (Heidelb.) 10:791-806 (2020)). As such, there remains a clear unmet need for additional advancements in treatment options to address the complex medical and societal needs of patients with moderate to severe AD.

A multiplicity of factors, including epidermal barrier defects, dysregulation of innate immune responses, and altered Type 2 immunity, are implicated in the pathogenesis of AD, culminating in a series of complex inflammatory responses involving multiple cell types, cytokines and chemokines. Enhanced allergen/antigen penetration through an impaired skin barrier resulting in a type 2 T helper (Th2)-type milieu has been proposed as a critical link between the primary barrier defect in patients with AD and Th2 polarization (Boguniewicz et al., Immunol. Rev. 242: 233-46 (2011)). Th2 differentiation of naive CD4+ T cells predominates in AD causing an increased production of interleukins (IL), primarily IL-4, IL-5, and IL-13, which then leads to an increased level of immunoglobulin E (IgE) (Alexander et al., F1000Res. 8:F1000 Faculty Rev-132 (2019)). IL-4 and IL-13 are both key cytokines involved in type 2 inflammatory conditions; however, evidence continues to emerge that supports IL-13 as a primary cytokine involved in AD (Bieber, Allergy 75:54-62 (2020)).

Until recently, treatment for moderate or severe AD involved hydration of the skin, and/or application of topical treatments such as corticosteroids, calcineurin inhibitors, nonsteroidal phosphodiesterase 4 inhibitors, tar, vitamin D, or dilute bleach. First line therapy for moderate to severe AD is treatment with topical corticosteroids (TCS). Topical calcineurin inhibitors (TCI), are typically used as second line therapy, or as an alternative therapy for patients with TCS intolerance. Although topical therapies remain a mainstay in the treatment in AD, these treatments continue to be associated with limited efficacy. In addition, long-term application of TCS carries the risk of side-effects, such as acneiform eruptions, dyspigmentation, skin atrophy, and risks associated with systemic absorption (Sidbury et al., J. Am. Acad. Dermatol. 71:327-49 (2014)).

Moderate or severe cases of AD not adequately controlled by topical treatments are typically treated with phototherapy or other systemic treatment (e.g., oral corticosteroids, cyclosporine, methotrexate, mycophenolate, and azathioprine). For most patients, long term treatment with these agents only provide modest efficacy and carries the potential for significant safety issues and long-term complications, such as organ toxicities (Schneider et al.; Simpson et al., Semin. Cutan. Med. Surg. 36:124-30 (2017)).

More recently, biologic and small molecule therapies have proven to be promising investigational treatments for AD. In particular, the recent European Medicines Agency and the U.S. Food and Drug Administration approval of dupilumab represents a significant treatment advance for AD patients (Ariëns et al., Ther. Adv. Chronic Dis. 9:159-70 (2018)). Nevertheless, AD exhibits biological and clinical heterogeneity (Muraro et al., J. Allergy Clin. Immunol. 137:1347-58 (2016), Czarnowicki et al., J. Allergy Clin. Immunol. 143:1-11 (2019)), where even novel therapeutic agents such as dupilumab, have displayed variable efficacy responses in subjects with moderate to severe AD. Results from dupilumab's Phase 3 registrational program (SOLO 1 and SOLO 2), demonstrated efficacy in treating patients moderate to severe AD. However less than half of the subjects (38% to 36% respectively) enrolled in the pivotal studies experienced a reduction of Investigators' Global Assessment (IGA) to either 1 (almost clear) or 0 (clear) after 16 weeks of treatment. These data highlight some of the challenges physicians face in treating patients with moderate to severe disease, as even with advanced therapeutic agents such as dupilumab, a majority of the patients do not have adequate control of their disease. As such, there remains a high unmet need for novel targeted therapies to improve patient outcomes, lessen disease burden, and further expand the current treatment paradigms available for AD patients with more advanced disease. (Simpson et al. (2017); Simpson et al., N. Eng. J. Med. 375:2335-48 (2016)).

SUMMARY

One aspect is for a method of treating atopic dermatitis comprising administering to a subject in need thereof a therapeutically effective amount of an anti-IL-13 antibody, or antigen binding fragment thereof, thereby treating atopic dermatitis in the subject. In some embodiments, the anti-IL-13 antibody comprises an antigen binding domain comprising six CDRs: CDR-H1, CDR-H2, CDR-H3, CDR-L1, CDR-L2, and CDR-L3, wherein the anti-IL-13 antibody comprises at least one of: (a) CDR-H1 comprising residues 31-37 of SEQ ID NO:2; (b) CDR-H2 comprising residues 52-67 of SEQ ID NO:2; (c) CDR-H3 comprising residues 100-112 of SEQ ID NO:2; (d) CDR-L1 comprising residues 24-34 of SEQ ID NO:3; (e) CDR-L2 comprising residues 50-56 of SEQ ID NO:3; or (f) CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, and CDR-H3 comprising residues 100-112 of SEQ ID NO:2. In some embodiments, the anti-IL-13 antibody comprises CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, CDR-H3 comprising residues 100-112 of SEQ ID NO:2, CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises a heavy chain variable domain comprising the amino acid sequence of SEQ ID NO:2. In some embodiments, the anti-IL-13 antibody comprises a light chain variable domain comprising the amino acid sequence of SEQ ID NO:3. In some embodiments, the anti-IL-13 antibody comprises a heavy chain variable domain comprising the amino acid sequence of SEQ ID NO:2 and a light chain variable domain comprising the amino acid sequence of SEQ ID NO:3. In some embodiments, the anti-IL-13 antibody comprises an L240A mutation. In some embodiments, the anti-IL-13 antibody comprises an L241A mutation. In some embodiments, the anti-IL-13 antibody comprises an L240A mutation and L241A mutation. In some embodiments, the anti-IL-13 antibody is cendakimab. In some embodiments, the anti-IL-13 antibody is administered subcutaneously. In some embodiments, the anti-IL-13 antibody is administered at a dosage of about 100 mg to about 1000 mg to the subject. In some embodiments, the anti-IL-13 antibody is administered at a dosage of about 200 mg to about 900 mg to the subject. In some embodiments, the anti-IL-13 antibody is administered at a dosage of about 300 mg to about 800 mg to the subject. In some embodiments, the anti-IL-13 antibody is administered at a dosage of about 360 mg to about 720 mg to the subject. In some embodiments, the atopic dermatitis is a moderate atopic dermatitis. In some embodiments, the atopic dermatitis is a severe atopic dermatitis. In some embodiments, the atopic dermatitis is a moderate to severe atopic dermatitis.

Another aspect is for an anti-IL-13 antibody, or antigen binding fragment thereof, for use in the treatment of atopic dermatitis. In some embodiments, the anti-IL-13 antibody comprises an antigen binding domain comprising six CDRs: CDR-H1, CDR-H2, CDR-H3, CDR-L1, CDR-L2, and CDR-L3, wherein the anti-IL-13 antibody comprises at least one of: (a) CDR-H1 comprising residues 31-37 of SEQ ID NO:2; (b) CDR-H2 comprising residues 52-67 of SEQ ID NO:2; (c) CDR-H3 comprising residues 100-112 of SEQ ID NO:2; (d) CDR-L1 comprising residues 24-34 of SEQ ID NO:3; (e) CDR-L2 comprising residues 50-56 of SEQ ID NO:3; or (f) CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, and CDR-H3 comprising residues 100-112 of SEQ ID NO:2. In some embodiments, the anti-IL-13 antibody comprises CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, CDR-H3 comprising residues 100-112 of SEQ ID NO:2, CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises a heavy chain variable domain comprising the amino acid sequence of SEQ ID NO:2. In some embodiments, the anti-IL-13 antibody comprises a light chain variable domain comprising the amino acid sequence of SEQ ID NO:3. In some embodiments, the anti-IL-13 antibody comprises a heavy chain variable domain comprising the amino acid sequence of SEQ ID NO:2 and a light chain variable domain comprising the amino acid sequence of SEQ ID NO:3. In some embodiments, the anti-IL-13 antibody comprises an L240A mutation. In some embodiments, the anti-IL-13 antibody comprises an L241A mutation. In some embodiments, the anti-IL-13 antibody comprises an L240A mutation and L241A mutation. In some embodiments, the anti-IL-13 antibody is cendakimab. In some embodiments, the anti-IL-13 antibody is administered subcutaneously. In some embodiments, the anti-IL-13 antibody is administered at a dosage of about 100 mg to about 1000 mg to the subject. In some embodiments, the anti-IL-13 antibody is administered at a dosage of about 200 mg to about 900 mg to the subject. In some embodiments, the anti-IL-13 antibody is administered at a dosage of about 300 mg to about 800 mg to the subject. In some embodiments, the anti-IL-13 antibody is administered at a dosage of about 360 mg to about 720 mg to the subject. In some embodiments, the atopic dermatitis is a moderate atopic dermatitis. In some embodiments, the atopic dermatitis is a severe atopic dermatitis. In some embodiments, the atopic dermatitis is a moderate to severe atopic dermatitis.

A further aspect is for use of an anti-IL-13 antibody, or antigen binding fragment thereof, for the manufacture of a medicament for the treatment of atopic dermatitis. In some embodiments, the anti-IL-13 antibody comprises an antigen binding domain comprising six CDRs: CDR-H1, CDR-H2, CDR-H3, CDR-L1, CDR-L2, and CDR-L3, wherein the anti-IL-13 antibody comprises at least one of: (a) CDR-H1 comprising residues 31-37 of SEQ ID NO:2; (b) CDR-H2 comprising residues 52-67 of SEQ ID NO:2; (c) CDR-H3 comprising residues 100-112 of SEQ ID NO:2; (d) CDR-L1 comprising residues 24-34 of SEQ ID NO:3; (e) CDR-L2 comprising residues 50-56 of SEQ ID NO:3; or (f) CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, and CDR-H3 comprising residues 100-112 of SEQ ID NO:2. In some embodiments, the anti-IL-13 antibody comprises CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, CDR-H3 comprising residues 100-112 of SEQ ID NO:2, CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises a heavy chain variable domain comprising the amino acid sequence of SEQ ID NO:2. In some embodiments, the anti-IL-13 antibody comprises a light chain variable domain comprising the amino acid sequence of SEQ ID NO:3. In some embodiments, the anti-IL-13 antibody comprises a heavy chain variable domain comprising the amino acid sequence of SEQ ID NO:2 and a light chain variable domain comprising the amino acid sequence of SEQ ID NO:3. In some embodiments, the anti-IL-13 antibody comprises an L240A mutation. In some embodiments, the anti-IL-13 antibody comprises an L241A mutation. In some embodiments, the anti-IL-13 antibody comprises an L240A mutation and L241A mutation. In some embodiments, the anti-IL-13 antibody is cendakimab. In some embodiments, the anti-IL-13 antibody is formulated for subcutaneous administration. In some embodiments, the anti-IL-13 antibody is formulated for a dosage of about 100 mg to about 1000 mg. In some embodiments, the anti-IL-13 antibody is formulated for a dosage of about 200 mg to about 900 mg. In some embodiments, the anti-IL-13 antibody is formulated for a dosage of about 300 mg to about 800 mg. In some embodiments, the anti-IL-13 antibody is formulated for a dosage of about 360 mg to about 720 mg to the subject. In some embodiments, the atopic dermatitis is a moderate atopic dermatitis. In some embodiments, the atopic dermatitis is a severe atopic dermatitis. In some embodiments, the atopic dermatitis is a moderate to severe atopic dermatitis.

An additional aspect is for a method of reducing incidence of atopic dermatitis administering to a subject in need thereof a therapeutically effective amount of an anti-IL-13 antibody, or antigen binding fragment thereof, thereby reducing incidence of atopic dermatitis in the subject. In some embodiments, the anti-IL-13 antibody comprises an antigen binding domain comprising six CDRs: CDR-H1, CDR-H2, CDR-H3, CDR-L1, CDR-L2, and CDR-L3, wherein the anti-IL-13 antibody comprises at least one of: (a) CDR-H1 comprising residues 31-37 of SEQ ID NO:2; (b) CDR-H2 comprising residues 52-67 of SEQ ID NO:2; (c) CDR-H3 comprising residues 100-112 of SEQ ID NO:2; (d) CDR-L1 comprising residues 24-34 of SEQ ID NO:3; (e) CDR-L2 comprising residues 50-56 of SEQ ID NO:3; or (f) CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, and CDR-H3 comprising residues 100-112 of SEQ ID NO:2. In some embodiments, the anti-IL-13 antibody comprises CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, CDR-H3 comprising residues 100-112 of SEQ ID NO:2, CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises a heavy chain variable domain comprising the amino acid sequence of SEQ ID NO:2. In some embodiments, the anti-IL-13 antibody comprises a light chain variable domain comprising the amino acid sequence of SEQ ID NO:3. In some embodiments, the anti-IL-13 antibody comprises a heavy chain variable domain comprising the amino acid sequence of SEQ ID NO:2 and a light chain variable domain comprising the amino acid sequence of SEQ ID NO:3. In some embodiments, the anti-IL-13 antibody comprises an L240A mutation. In some embodiments, the anti-IL-13 antibody comprises an L241A mutation. In some embodiments, the anti-IL-13 antibody comprises an L240A mutation and L241A mutation. In some embodiments, the anti-IL-13 antibody is cendakimab. In some embodiments, the anti-IL-13 antibody is administered subcutaneously. In some embodiments, the anti-IL-13 antibody is administered at a dosage of about 100 mg to about 1000 mg to the subject. In some embodiments, the anti-IL-13 antibody is administered at a dosage of about 200 mg to about 900 mg to the subject. In some embodiments, the anti-IL-13 antibody is administered at a dosage of about 300 mg to about 800 mg to the subject. In some embodiments, the anti-IL-13 antibody is administered at a dosage of about 360 mg to about 720 mg to the subject. In some embodiments, the atopic dermatitis is a moderate atopic dermatitis. In some embodiments, the atopic dermatitis is a severe atopic dermatitis. In some embodiments, the atopic dermatitis is a moderate to severe atopic dermatitis.

Another aspect is for a method of treating atopic dermatitis comprising administering to a subject in need thereof a therapeutically effective amount of a pharmaceutical composition that prevents IL-13 interaction with IL-13Rα1 and IL-13Rα2. In some embodiments, the pharmaceutical composition comprises an anti-IL-13 antibody, or antigen binding fragment thereof, and in some embodiments, the anti-IL-13 antibody comprises an antigen binding domain comprising six CDRs: CDR-H1, CDR-H2, CDR-H3, CDR-L1, CDR-L2, and CDR-L3, wherein the anti-IL-13 antibody comprises at least one of: (a) CDR-H1 comprising residues 31-37 of SEQ ID NO:2; (b) CDR-H2 comprising residues 52-67 of SEQ ID NO:2; (c) CDR-H3 comprising residues 100-112 of SEQ ID NO:2; (d) CDR-L1 comprising residues 24-34 of SEQ ID NO:3; (e) CDR-L2 comprising residues 50-56 of SEQ ID NO:3; or (f) CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, and CDR-H3 comprising residues 100-112 of SEQ ID NO:2. In some embodiments, the anti-IL-13 antibody comprises CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, CDR-H3 comprising residues 100-112 of SEQ ID NO:2, CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises a heavy chain variable domain comprising the amino acid sequence of SEQ ID NO:2. In some embodiments, the anti-IL-13 antibody comprises a light chain variable domain comprising the amino acid sequence of SEQ ID NO:3. In some embodiments, the anti-IL-13 antibody comprises a heavy chain variable domain comprising the amino acid sequence of SEQ ID NO:2 and a light chain variable domain comprising the amino acid sequence of SEQ ID NO:3. In some embodiments, the anti-IL-13 antibody comprises an L240A mutation. In some embodiments, the anti-IL-13 antibody comprises an L241A mutation. In some embodiments, the anti-IL-13 antibody comprises an L240A mutation and L241A mutation. In some embodiments, the anti-IL-13 antibody is cendakimab. In some embodiments, the anti-IL-13 antibody is administered subcutaneously. In some embodiments, the anti-IL-13 antibody is administered at a dosage of about 100 mg to about 1000 mg to the subject. In some embodiments, the anti-IL-13 antibody is administered at a dosage of about 200 mg to about 900 mg to the subject. In some embodiments, the anti-IL-13 antibody is administered at a dosage of about 300 mg to about 800 mg to the subject. In some embodiments, the anti-IL-13 antibody is administered at a dosage of about 360 mg to about 720 mg to the subject. In some embodiments, the atopic dermatitis is a moderate atopic dermatitis. In some embodiments, the atopic dermatitis is a severe atopic dermatitis. In some embodiments, the atopic dermatitis is a moderate to severe atopic dermatitis.

A further aspect is for a method of determining the effectiveness of treating atopic dermatitis in a subject in need thereof comprising (a) administering to the subject a therapeutically effective amount of an anti-IL-13 antibody, or antigen binding fragment thereof, thereby treating atopic dermatitis in the subject; and (b) determining whether the subject exhibits an increase or decrease in the level of one or more of peripheral blood eosinophils, IgE, lactate dehydrogenase, IL-13, IL-22, TARC, and/or PARC from a baseline level of peripheral blood eosinophils, IgE, lactate dehydrogenase, IL-13, IL-22, TARC, and/or PARC in the subject prior to the administering of step (a). In some embodiments, the anti-IL-13 antibody comprises an antigen binding domain comprising six CDRs: CDR-H1, CDR-H2, CDR-H3, CDR-L1, CDR-L2, and CDR-L3, wherein the anti-IL-13 antibody comprises at least one of: (a) CDR-H1 comprising residues 31-37 of SEQ ID NO:2; (b) CDR-H2 comprising residues 52-67 of SEQ ID NO:2; (c) CDR-H3 comprising residues 100-112 of SEQ ID NO:2; (d) CDR-L1 comprising residues 24-34 of SEQ ID NO:3; (e) CDR-L2 comprising residues 50-56 of SEQ ID NO:3; or (f) CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, and CDR-H3 comprising residues 100-112 of SEQ ID NO:2. In some embodiments, the anti-IL-13 antibody comprises CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, CDR-H3 comprising residues 100-112 of SEQ ID NO:2, CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises a heavy chain variable domain comprising the amino acid sequence of SEQ ID NO:2. In some embodiments, the anti-IL-13 antibody comprises a light chain variable domain comprising the amino acid sequence of SEQ ID NO:3. In some embodiments, the anti-IL-13 antibody comprises a heavy chain variable domain comprising the amino acid sequence of SEQ ID NO:2 and a light chain variable domain comprising the amino acid sequence of SEQ ID NO:3. In some embodiments, the anti-IL-13 antibody comprises an L240A mutation. In some embodiments, the anti-IL-13 antibody comprises an L241A mutation. In some embodiments, the anti-IL-13 antibody comprises an L240A mutation and L241A mutation. In some embodiments, the anti-IL-13 antibody is cendakimab. In some embodiments, the anti-IL-13 antibody is administered subcutaneously. In some embodiments, the anti-IL-13 antibody is administered at a dosage of about 100 mg to about 1000 mg to the subject. In some embodiments, the anti-IL-13 antibody is administered at a dosage of about 200 mg to about 900 mg to the subject. In some embodiments, the anti-IL-13 antibody is administered at a dosage of about 300 mg to about 800 mg to the subject. In some embodiments, the anti-IL-13 antibody is administered at a dosage of about 360 mg to about 720 mg to the subject. In some embodiments, the atopic dermatitis is a moderate atopic dermatitis. In some embodiments, the atopic dermatitis is a severe atopic dermatitis. In some embodiments, the atopic dermatitis is a moderate to severe atopic dermatitis.

An additional aspect is for a method of treating or ameliorating at least one symptom or indication of atopic dermatitis comprising administering to a subject in need thereof a therapeutically effective amount of an anti-IL-13 antibody, or antigen binding fragment thereof, thereby treating or ameliorating the at least one symptom in the subject, wherein the at least one symptom is pruritus; dry skin; itching; red to brownish-gray patches of skin; small, raised bumps which that leak fluid and crust over when scratched; thickened skin; cracked skin; scaly skin; raw skin; skin sensitivity; or swollen skin. In some embodiments, the anti-IL-13 antibody comprises an antigen binding domain comprising six CDRs: CDR-H1, CDR-H2, CDR-H3, CDR-L1, CDR-L2, and CDR-L3, wherein the anti-IL-13 antibody comprises at least one of: (a) CDR-H1 comprising residues 31-37 of SEQ ID NO:2; (b) CDR-H2 comprising residues 52-67 of SEQ ID NO:2; (c) CDR-H3 comprising residues 100-112 of SEQ ID NO:2; (d) CDR-L1 comprising residues 24-34 of SEQ ID NO:3; (e) CDR-L2 comprising residues 50-56 of SEQ ID NO:3; or (f) CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, and CDR-H3 comprising residues 100-112 of SEQ ID NO:2. In some embodiments, the anti-IL-13 antibody comprises CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises CDR-H1 comprising residues 31-37 of SEQ ID NO:2, CDR-H2 comprising residues 52-67 of SEQ ID NO:2, CDR-H3 comprising residues 100-112 of SEQ ID NO:2, CDR-L1 comprising residues 24-34 of SEQ ID NO:3, CDR-L2 comprising residues 50-56 of SEQ ID NO:3, and CDR-L3 comprising residues 89-97 of SEQ ID NO:3. In some embodiments, the anti-IL-13 antibody comprises a heavy chain variable domain comprising the amino acid sequence of SEQ ID NO:2. In some embodiments, the anti-IL-13 antibody comprises a light chain variable domain comprising the amino acid sequence of SEQ ID NO:3. In some embodiments, the anti-IL-13 antibody comprises a heavy chain variable domain comprising the amino acid sequence of SEQ ID NO:2 and a light chain variable domain comprising the amino acid sequence of SEQ ID NO:3. In some embodiments, the anti-IL-13 antibody comprises an L240A mutation. In some embodiments, the anti-IL-13 antibody comprises an L241A mutation. In some embodiments, the anti-IL-13 antibody comprises an L240A mutation and L241A mutation. In some embodiments, the anti- IL-13 antibody is cendakimab. In some embodiments, the anti-IL-13 antibody is administered subcutaneously. In some embodiments, the anti-IL-13 antibody is administered at a dosage of about 100 mg to about 1000 mg to the subject. In some embodiments, the anti-IL-13 antibody is administered at a dosage of about 200 mg to about 900 mg to the subject. In some embodiments, the anti-IL-13 antibody is administered at a dosage of about 300 mg to about 800 mg to the subject. In some embodiments, the anti-IL-13 antibody is administered at a dosage of about 360 mg to about 720 mg to the subject. In some embodiments, the atopic dermatitis is a moderate atopic dermatitis. In some embodiments, the atopic dermatitis is a severe atopic dermatitis. In some embodiments, the atopic dermatitis is a moderate to severe atopic dermatitis.

Other objects and advantages will become apparent to those skilled in the art upon reference to the detailed description that hereinafter follows.

DETAILED DESCRIPTION

Applicants have solved the stated problem. Cendakimab is a recombinant, humanized, high-affinity neutralizing (immunoglobulin G1 kappa [IgG1κ]) monoclonal antibody (mAb). Cendakimab is highly selective for human IL-13 and was generated by humanization of a rodent anti-human IL-13 mAb, which was identified using hybridoma technology through immunization of mice with human 0110 variant recombinant IL-13. The fragment, crystallizable (Fc) region of cendakimab is mutated at residues L240A and L241A in the heavy chain hinge/CH2 region to reduce effector function as suggested by literature reports (Hezareh et al., J. Virol. 75:12161-68 (2001)). Cendakimab is produced by mammalian cell expression.

IL-13 is a cytokine that is expressed by a large number of cell types including most leukocytes, mast cells, epithelial cells, fibroblasts, and smooth muscle cells (Brightling et al., Clin. Exp. Allergy 40:42-49 (2010)). Cendakimab has high affinity for wild-type IL-13 and a common variant of IL-13, 0110, which is associated with and enhances human allergic inflammation (Vladich et al., J. Clin. Invest. 115:747-54 (2005)). Cendakimab binds an IL-13 epitope, comprised of residues in helix A and helix D. This binding in turn prevents IL-13 from binding to both IL-13 receptor alpha 1 (IL-13Rα1) and IL-13 receptor alpha 2 (IL-13Rα2) (Ying et al., American Thoracic Society Conference, Abstract 6644 (2010)).

IL-13, IL-13Rα1, and IL-13 Rα2 are overexpressed in the lesional skin of AD (Tsoi et al., J. Invest. Dermatol. 139: 1480-89 (2019)), Esaki et al., J. Allergy Clin. Immunol. 135:153-63 (2015)). In addition, mechanical scratching, as well as IL-13 itself, also upregulates IL-13 Rα2 expression (Ulzii et al., Int. J. Mol. Sci. 20:3324 (2019)). The scratch-induced IL-13 Rα2 upregulation may attenuate the IL-13-mediated epidermal barrier dysfunction and dermal fibrosis.

Applicants have found that anti-IL-13 antibodies are an effective therapeutic option for subjects with AD. New therapies for AD, like use of anti-IL-13 antibodies, provide a unique opportunity to potentially optimize efficacy.

Definitions

In this disclosure, a number of terms and abbreviations are used. The following definitions are provided.

As used herein, the term "about" or "approximately" means within 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or less of a given value or range.

The term "comprising" is intended to include embodiments encompassed by the terms "consisting essentially of" and "consisting of". Similarly, the term "consisting essentially of" is intended to include embodiments encompassed by the term "consisting of".

The indefinite articles "a" and "an", as used herein in the specification and in the claims, unless clearly indicated to the contrary, should be understood to mean "at least one".

The phrase "and/or", as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or, when used in the claims, "consisting of", will refer to the inclusion of exactly one element of a number or list of elements. In general, the term "or" as used herein shall only be interpreted as indicating exclusive alternatives (i.e., "one or the other but not both") when preceded by terms of exclusivity, "either", "one of", "only one of", "exactly one of". "Consisting essentially of", when used in the claims, shall have its ordinary meaning as used in the field of patent law.

The terms "IL-13" and "IL-13 wild type", as used herein, include a cytokine that is secreted primarily by T helper 2 cells. The terms "IL-13" and "IL-13 wild type" include a monomeric protein of 13 kDa polypeptide. The structure of IL-13 is described further in, for example, Moy et al., J. Mol. Biol. 310:219-30 (2001). The term IL-13 is intended to include recombinant human IL-13 (rh IL-13), which can be prepared by standard recombinant expression methods. Additionally, the term may include orthologs/homologs of IL-13 in other species, for example, dogs, cats, cows, horses, pigs, chicken, etc.

In some embodiments, the IL-13 polypeptide targets of the instant disclosure include human IL-13 proteins, including, variants, fragments, isoforms, and congeners thereof. The amino acid sequence of human IL-13 is known in the art and is depicted in SEQ ID NO:1 (NCBI accession No. AF043334.1 (ver. 1, updated Mar. 10, 2010); UNIPROT accession No. P35225 (ver. 170; reviewed Mar. 16, 2016)).

```
Sequence of human IL-13 wild type (SEQ ID NO: 1):
MALLLTTVIALTCLGGFASPGPVPPSTALRELIEELVNITQNQKAPLCN
GSMVWSINLTAGMYCAALESLINVSGCSAIEKTQRMLSGFCPHKVSAGQ
FSSLHVRDTKIEVAQFVKDLLLHLKKLFREGRFN
```

The term "IL-13 variant" (abbreviated herein as IL-13v), as used herein, includes any variant of IL-13. An example of a human IL-13 variant is wherein amino acid residue 130 of SEQ ID NO:1 is changed from Arginine to Glutamine (R130Q). This particular human IL-13 variant sequence is known in the art (NCBI accession No. AAH96141.2 (ver. 2, updated Sep. 23, 2014)).

The receptor portion of the IL-13 ligand/receptor system comprises a multimeric, transmembrane receptor that includes the alpha chain of the IL-4 receptor (IL-4Rα) and at least one of two known IL-13-specific binding chains (Wynn et al., Annu. Rev. Immunol. 21:425-56 (2003)). The effects are mediated primarily via a transcription factor, signal transducer and activator of transcription 6 (STATE).

Particularly, the antibody or an antigen-binding fragment thereof specifically binds to an IL-13 polypeptide, thereby diminishing or neutralizing the binding of the IL-13 ligand to its cognate receptor. Concomitantly, the IL-13 antibody, or antigen-binding portion thereof, may result in the inhibition and/or neutralization of the biological activity of the IL-13 ligand/receptor system.

"Biological activity" as used herein, refers to all inherent biological properties of the cytokine. Biological properties of IL-13 include, but are not limited to, binding IL-13 receptor to elicit inflammation, enhanced secretion of chemokines, increased migration of allergic effector cells, metaplasia, etc. in the epithelial tissue surrounding the mucosa of the GI tract.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed herein. In one embodiment, the antibody used in the compositions and methods of the disclosure is the anti-IL-13 antibody cendakimab.

In a full-length antibody, each heavy chain is comprised of a heavy chain variable region (abbreviated herein as HCVR or VH) and a heavy chain constant region. The heavy chain constant region is comprised of three domains, CHI, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FRI, CDRI, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgAI and IgA2) or subclass.

In some embodiments, the anti-IL-13 antibody has a heavy chain variable region as set forth in SEQ ID NO:2. In some embodiments, the anti-IL-13 antibody has a light chain variable region as set forth in SEQ ID NO:3.

Heavy Chain Variable Region
(SEQ ID NO: 2)
EVTLRESGPGLVKPTQTLTLTCTLYGFSLSTSDMGVDWIRQPPGKGLEW
LAHIWWDDVKRYNPALKSRLTISKDTSKNQVVLKLTSVDPVDTATYYCA
RTVSSGYIYYAMDYWGQGTLVTVSS
Light Chain Variable Region
(SEQ ID NO: 3)
DIQMTQSPSSLSASVGDRVTISCRASQDIRNYLNWYQQKPGKAPKLLIF
YTSKLHSGVPSRFSGSGSGTDYTLTISSLQPEDIATYYCQQGNTLPLTF
GGGTKVEIK The term "antigen-binding portion" of an antibody (or simply "antibody portion"), as used herein, refers to one or more fragments of an antibody that retain the ability to specifically bind to an antigen (e.g., IL-13). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., Nature 341:544-46 (1989); WO90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., Science 242:423-26 (1988); Huston et al., Proc. Natl. Acad. Sci. USA 85:5879-83 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., Proc. Natl. Acad. Sci. USA 90:6444-48 (1993); Poljak et al., Structure 2:1121-23 (1994)). Such antibody binding portions are known in the art (Kontermann and Dubel eds., Antibody Engineering (2001) Springer-Verlag. New York. 790 pp. (ISBN 3-540-41354-5)).

The term "antibody construct" as used herein refers to a polypeptide comprising one or more the antigen binding portions of the disclosure linked to a linker polypeptide or an immunoglobulin constant domain. Linker polypeptides comprise two or more amino acid residues joined by peptide bonds and are used to link one or more antigen binding portions. Such linker polypeptides are well known in the art (see, e.g., Holliger et al., Proc. Natl. Acad. Sci. USA 90:6444-48 (1993); Poljak et al., Structure 2: 1121-23 (1994)). An immunoglobulin constant domain refers to a heavy or light chain constant domain. Human IgG heavy chain and light chain constant domain amino acid sequences are known in the art and as described in the table below.

TABLE 1

Sequence of human IgG heavy chain constant domain and light chain constant domain

| Protein | Sequence Identifier | Sequence |
| --- | --- | --- |
| Ig gamma-1 constant region | 4 | ASTKGPSVFFLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig gamma-1 constant region mutant | 5 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig Kappa constant region | 6 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| Ig Lambda constant region | 7 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al., Human Antibodies and Hybridomas 6:93-101 (1995)) and use of a cysteine residue, a marker peptide and a C-terminal polyhistidine tag to make bivalent and biotinylated scFv molecules (Kipriyanov et al., Mol. Immunol. 31:1047-58 (1994)). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds IL-13 is substantially free of antibodies that specifically bind antigens other than IL-13). An isolated antibody that specifically binds IL-13 may, however, have cross-reactivity to other antigens, such as IL-13 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom et al., TIB Tech. 15:62-70 (1994); Azzazy et al., Clin. Biochem. 35:425-45 (2002); Gavilondo et al., BioTechniques 29:128-45 (2002); Hoogenboom et al., Immunol. Today 21:371-78 (2000)), antibodies isolated from an animal (e.g., a mouse) that is transgenic for human immunoglobulin genes (see e.g., Taylor et al., Nucleic Acids Res. 20:6287-95 (1992); Kellermann et al., Curr. Opin. Biotechnol. 13:593-97 (2002); Little et al., Immunol. Today 21:364-70 (2002)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding human IL-13 which can be generated using techniques well known in the art, such as, but not limited to, using human Ig phage libraries such as those disclosed in (WO2005/007699).

The term "chimeric antibody" refers to antibodies which comprise heavy and light chain variable region sequences from one species and constant region sequences from another species, such as antibodies having murine heavy and light chain variable regions linked to human constant regions. See, e.g., Morrison, Science 229:1202-07 (1985); Oi et al., BioTechniques 4:214-21 (1986); Gillies et al., J. Immunol. Methods 125: 91-202 (1989); U.S. Pat. Nos. 5,807,715; 4,816,567; and 4,816,397, which are incorporated herein by reference in their entireties. In addition, "chimeric antibodies" may be produced by art-known techniques. See Morrison et al., Proc. Natl. Acad. Sci. USA 81:851-55 (1984); Neuberger et al., Nature 312:604-08 (1984); Takeda et al., Nature 314:452-54 (1985).

In one embodiment, the chimeric antibodies for use in the compositions and/or methods of the disclosure are produced by replacing the heavy chain constant region of the murine monoclonal anti human IL-13 antibodies described in section 1 with a human IgGI constant region.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti human IL-13 antibodies and antigen binding portions are provided. Such antibodies were generated by obtaining murine anti-IL-13 monoclonal antibodies using traditional hybridoma technology followed by humanization using in vitro genetic engineering, such as those disclosed in WO 2005/123126. Human Ig sequences are known in the art. See, e.g., Kabat et al., Sequences of Proteins of Immunological Interest, U.S. Dept. Health (1983), entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, and in some embodiments improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; Riechmann et al., Nature 332:323-27 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321: 522-25 (1986); Verhoeyen et al., Science 239:1534-36 (1988); Sims et al., J. Immunol. 151:2296-2308 (1993); Chothia et al., J. Mol. Biol. 196:901-17 (1987); Carter et al., Proc. Natl. Acad. Sci. U.S.A. 89:4285-89 (1992); Presta et al., J. Immunol. 151:2623-32 (1993); Padlan, Mol. Immunol. 28:489-98 (1991); Studnicka et al., Protein Eng. 7:805-14 (1994); Roguska et al., Proc. Natl. Acad. Sci. U.S.A. 91:969-73 (1994); WO91/09967; PCT/US98/16280; PCT/US96/18978; PCT/US91/09630; PCT/US91/05939; PCT/US94/01234; PCT/GB89/01334; PCT/GB91/01134; PCT/GB92/01755; WO90/14443; WO90/14424; WO90/14430; EP 229246; EP 592,106; EP 519,596; EP 239,400; U.S. Pat. Nos. 5,565,332, 5,723,323, 5,976,862, 5,824,514, 5,817, 483, 5,814,476, 5,763,192, 5,723,323, 5,766,886, 5,714,352, 6,204,023, 6,180,370, 5,693,762, 5,530,101, 5,585,089, 5,225,539, 4,816,567, each entirely incorporated herein by reference, included references cited therein.

Other types of libraries may be comprised of antibody fragments from a source of genes that is not explicitly biased for clones that bind to an antigen. Thus, "naive antibody" or "natural antibody" libraries derive from natural, unimmunized, rearranged V genes.

"Synthetic antibody" libraries are constructed entirely by in vitro methods, introducing areas of complete or tailored degeneracy into the CDRs of one or more V genes. "Semi-synthetic libraries" combine natural and synthetic diversity, and are often created to increase natural diversity while maintaining a desired level of functional diversity. Thus, such libraries can, for example, be created by shuffling natural CDR regions (Soderlind et al., Nat. Biotechnol. 18:852-56 (2000)), or by combining naturally rearranged CDR sequences from human B cells with synthetic CDR1 and CDR2 diversity (Hoet et al., Nat. Biotechnol. 23:344-38 (2005)). The present disclosure encompasses the use of naive/natural, synthetic and semisynthetic antibody libraries, or any combination thereof.

The terms "Kabat numbering", "Kabat definitions", and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al., Ann. NY Acad. Sci.

190:382-91 (1971); Kabat et al., Sequences of Proteins of Immunological Interest, Fifth Edition, U.S. Department of Health and Human Services, NIH Publication No. 91-3242 (1991)). In some embodiments, for the heavy chain variable region of an anti-IL-13 antibody, the hypervariable region ranges from amino acid positions 31 to 37 of SEQ ID NO:2 for CDR1, amino acid positions 52 to 67 of SEQ ID NO:2 for CDR2, and amino acid positions 100 to 112 of SEQ ID NO:2 for CDR3. In some embodiments, for the light chain variable region of an anti-IL-13 antibody, the hypervariable region ranges from amino acid positions 24 to 34 of SEQ ID NO:3 for CDR1, amino acid positions 50 to 56 of SEQ ID NO:3 for CDR2, and amino acid positions 89 to 97 of SEQ ID NO:2 for CDR3.

As used herein, the terms "acceptor" and "acceptor antibody" refer to the antibody or nucleic acid sequence providing or encoding at least 80%, 81%, 82%, 83%, 84%, 85%, 86%, 87%, 88%, 89%, 90%, 91% 92%, 93%, 94%, 95%, 96%, 97%, 98%, 99%, or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, 81%, 82%, 83%, 84%, 85%, 86%, 87%, 88%, 89%, 90%, 91% 92%, 93%, 94%, 95%, 96%, 97%, 98%, 99%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., J. Mol. Biol. 196:901-17 (1987); Chothia et al., Nature 342:877-83 (1989)) found that certain sub-portions within Kabat CDRs adopt nearly identical peptide backbone conformations, despite having great diversity at the level of amino acid sequence. These sub-portions were designated as LI, L2 and L3 or HI, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan, FASEB J. 9:133-39 (1995), and MacCallum, J. Mol. Biol. 262:732-45 (1996). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although some embodiments use Kabat or Chothia.

As used herein, the term "canonical" residue refers to a residue in a CDR or framework that defines a particular canonical CDR structure as defined by Chothia et al., J. Mol. Biol. 196:901-07 (1987); Chothia et al., J. Mol. Biol. 227: 799-817 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In some embodiments, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or 'framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the disclosure the human heavy chain and light chain acceptor sequences are selected from the sequences described in Table 3 and Table 4 disclosed in U.S. Pat. No. 7,915,388, the contents of which are incorporated herein by reference.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin (See, e.g., Shapiro et al., Crit. Rev. Immunol. 22:183-200 (2002); Marchalonis et al., Adv. Exp. Med. Biol. 484:13-30 (2001)). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immuno specific ally binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, 81%, 82%, 83%, 84%, 85%, 86%, 87%, 88%, 89%, 90%, 91% 92%, 93%, 94%, 95%, 96%, 97%, 98%, 99% or more identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In some embodiments, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CHI, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In some embodiments, such mutations, however, will not be extensive. Usually, at least 80%, 81%, 82%, 83%, 84%, 85%, 86%, 87%, 88%, 89%, 90%, 91% 92%, 93%, 94%, 95% or more of the humanized antibody residues will correspond to those of the parental FR and CDR sequences.

As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

In some embodiments, the anti-IL-13 antibody is mutated at residue(s) L240A and/or L241A in the heavy chain hinge/CH2 region.

In some embodiments, the humanized anti-IL-13 antibody is cendakimab. Cendakimab has the sequences SEQ ID NO: 2 (heavy chain variable region) and SEQ ID NO: 3 (light chain variable region). Cendakimab is a humanized antibody that binds with great affinity to helices A and D of interleukin 13 (IL-13) (see US Patent Pub. No. 2014/0341913). Cendakimab comprises mutation at residues L240A and L241A in the heavy chain hinge/CH2 region.

The term "activity" includes activities such as the binding specificity/affinity of an antibody for an antigen, for example, an anti-IL-13 antibody that binds to an IL-13 antigen and/or the neutralizing potency of an antibody, for example, an anti-IL-13 antibody whose binding to IL-13 inhibits the biological activity of IL-13.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

Any known method may be employed to detect antibody-antigen interactions. For example, surface plasmon resonance (SPR) is an optical phenomenon that permits analysis of bio specific interactions by detection of alterations in protein concentrations within a biosensor matrix, for example using the BIACORE system (Pharmacia Biosensor, Piscataway, N.J.). See Jonsson et al., Ann. Biol. Clin. 51:19-26 (1993); Jonsson et al., Biotechniques 11:620-27 (1991); Johnsson et al., J. Mol. Recognit. 8:125-31 (1995); and Johnnson et al., Anal. Biochem. 198:268-77 (1991).

The anti-IL-13 antibodies used in the context of the methods of the present disclosure may have pH-dependent binding characteristics. For example, an anti-IL-13 antibody for use in the methods of the present disclosure may exhibit reduced binding to IL-13 at acidic pH as compared to neutral pH. Alternatively, an anti-IL-13 antibody of the disclosure may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-13 at acidic pH as compared to neutral pH" is expressed in terms of a ratio of the KD value of the antibody binding to IL-13 at acidic pH to the KD value of the antibody binding to IL-13 at neutral pH (or vice versa). For example, an antibody or antigen-binding fragment thereof may be regarded as exhibiting "reduced binding to IL-13 at acidic pH as compared to neutral pH" for purposes of the present disclosure if the antibody or antigen-binding fragment thereof exhibits an acidic/neutral KD ratio of about 3.0 or greater. In certain exemplary embodiments, the acidic/neutral KD ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

The aforementioned antibodies may be conjugated to other moieties and/or agents to achieve desired properties, e.g., physiological stability, increased half-life, increased bioavailability, etc. The term "antibody conjugate" refers to a binding protein, such as an antibody, chemically linked to a second chemical moiety, such as a therapeutic or cytotoxic agent. In other instances, the chemical moiety may be a diagnostic agent, e.g., a radio-ligand. The term "agent" is used herein to denote a chemical compound, a mixture of chemical compounds, a biological macromolecule, or an extract made from biological materials.

In some embodiments, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydro testosterone, glucocorticoids, procaine, tetracaine, lidocaine, propranolol, and puromycin and analogs or homologs thereof. The term "regulate" and 'modulate" are used interchangeably, and, as used herein, refers to a change or an alteration in the activity of a molecule of interest (e.g., the biological activity of IL-13). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator", as used herein, is a compound capable of changing or altering an activity or function of a molecule of interest (e.g., the biological activity of IL-13). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO 01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-13 polypeptides or polypeptides, nucleic acids, carbohydrates, or any other molecules that bind to IL-13.

The term "antagonist" or "inhibitor', as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of IL-13 and/or IL-13v. Antagonists and inhibitors of IL-13 and/or IL-13v may include, but are not limited to, proteins; nucleic acids, carbohydrates, or any other molecules, which bind to IL-13 or IL-13v.

The term "inhibit binding to the receptor" refers to the ability of the binding protein to prevent the binding of IL-13 to one or more of its receptors. Such inhibition of binding to the receptor would result in diminishing or abolishing the biological activity mediated by binding of IL-13 to its receptor or receptors.

As used herein, the term "effective amount" or "therapeutically effective amount" refers to the amount of an antibody, or antigen-binding portion thereof, which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

Pharmaceutical Compositions

The present disclosure includes methods which comprise administering an IL-13 antibody, or antigen-binding portion thereof, to a subject wherein the IL-13 antibody, or antigen-binding portion thereof, is contained within a pharmaceutical composition. The pharmaceutical compositions may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semisolid mixtures containing carbowax. See also Powell et al., J. Pharm. Sci. Technol. 52:238-311 (1998).

Various delivery systems are known and can be used to administer the pharmaceutical composition, e.g., encapsulation in liposomes, microparticles, microcapsules, recombinant cells capable of expressing the mutant viruses, receptor mediated endocytosis (see, e.g., Wu et al., J. Biol. Chem. 262:4429-32 (1987)). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition can be delivered subcutaneously or intravenously with a standard needle and syringe. In addition, with respect to subcutaneous delivery, a pen delivery device readily has applications in delivering a pharmaceutical composition. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, Science 249:1527-33 (1990).

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is, in some embodiments, filled in an appropriate ampoule.

The pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-13 antibody that can be used in the context of the present disclosure are disclosed, e.g., in US Patent Application No. 2012/0097565, the entire contents of which are expressly incorporated herein by reference.

The present disclosure provides a pharmaceutical composition comprising one or more of the aforementioned IL-13 antibodies, and antigen-binding portions thereof, and a pharmaceutically acceptable carrier. Additionally, in a related embodiment, the present disclosure provides a diagnostic composition comprising one or more of the aforementioned IL-13 antibodies, and antigen-binding portions thereof, and a plurality of reagents, buffers, and carriers for diagnostic testing. According to this aspect, the pharmaceutical composition may be formulated for intravenous administration, subcutaneous administration, intraperitoneal administration, or intramuscular administration. Still further according to this aspect, the pharmaceutical composition may be formulated for subcutaneous administration as a microneedle patch. The pharmaceutical compositions may be formulated for parenteral administration by bolus injection or by gradual perfusion over time. The diagnostic composition may be formulated for in vitro, in vivo, or ex vivo application.

Exemplary agents used in formulating the aforementioned IL-13 antibodies, and antigen-binding portions thereof, into pharmaceutical compositions and/or diagnostic compositions are provided in US Patent Application No. 2014/0341913, which is incorporated by reference herein. Specifically, exemplary agents used in formulating the aforementioned IL-13 antibodies, and antigen-binding portions thereof, into pharmaceutical compositions for the treatment of AD are provided in US Patent Application No. 2015/0017176, which is incorporated by reference herein.

Dosage and Administration

The amount of IL-13 antibody, or antigen-binding portion thereof, administered to a subject according to the methods of the present disclosure is, generally, a therapeutically effective amount.

In some embodiments, a therapeutically effective amount can be about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900, mg about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg or more of the anti-IL-13 antibody, or antigen-binding portion thereof.

In some embodiments, a therapeutically effective amount can be about 100 mg to about 1100 mg, about 120 mg to about 1100 mg, about 140 mg to about 1100 mg, about 160 mg to about 1100 mg, about 180 mg to about 1100 mg, about 200 mg to about 1100 mg, about 220 mg to about 1100 mg, about 240 mg to about 1100 mg, about 260 mg to about 1100 mg, about 280 mg to about 1100 mg, about 300 mg to about 1100 mg, about 320 mg to about 1100 mg, about 340 mg to about 1100 mg, about 360 mg to about 1100 mg, about 380 mg to about 1100 mg, about 400 mg to about 1100 mg, about 420 mg to about 1100 mg, about 440 mg to about 1100 mg, about 460 mg to about 1100 mg, about 480 mg to about 1100 mg, about 500 mg to about 1100 mg, about 520 mg to about 1100 mg, about 540 mg to about 1100 mg, about 560 mg to about 1100 mg, about 580 mg to about 1100 mg, about 600 mg to about 1100 mg, about 620 mg to about 1100 mg, about 640 mg to about 1100 mg, about 660 mg to about 1100 mg, about 680 mg to about 1100 mg, about 700 mg to about 1100 mg, about 720 mg to about 1100 mg, about 740 mg to about 1100 mg, about 760 mg to about 1100 mg, about 780 mg to about 1100 mg, about 800 mg to about 1100 mg, about 820 mg to about 1100 mg, about 840 mg to about 1100 mg, about 860 mg to about 1100 mg, about 880 mg to about 1100 mg, about 900 mg to about 1100 mg, about 920 mg to about 1100 mg, about 940 mg to about 1100 mg, about 960 mg to about 1100 mg, about 980 mg to about 1100 mg, about 1000 mg to about 1100 mg, about 1020 mg to about 1100 mg, about 1040 mg to about 1100 mg, about 1060 mg to about 1100 mg, about 1080 mg to about 1100 mg, about 100 mg to about 1080 mg, about 120 mg to about 1080 mg, about 140 mg to about 1080 mg, about 160 mg to about 1080 mg, about 180 mg to about 1080 mg, about 200 mg to about 1080 mg, about 220 mg to about 1080 mg, about 240 mg to about 1080 mg, about 260 mg to about 1080 mg, about 280 mg to about 1080 mg, about 300 mg to about 1080 mg, about 320 mg to about 1080 mg, about 340 mg to about 1080 mg, about 360 mg to about 1080 mg, about 380 mg to about 1080 mg, about 400 mg to about 1080 mg, about 420 mg to about 1080 mg, about 440 mg to about 1080 mg, about 460 mg to about 1080 mg, about 480 mg to about 1080 mg, about 500 mg to about 1080 mg, about 520 mg to about 1080 mg, about 540 mg to about 1080 mg, about 560 mg to about 1080 mg, about 580 mg to about 1080 mg, about 600 mg to about 1080 mg, about 620 mg to about 1080 mg, about 640 mg to about 1080 mg, about 660 mg to about 1080 mg, about 680 mg to about 1080 mg, about 700 mg to about 1080 mg, about 720 mg to about 1080 mg, about 740 mg to about 1080 mg, about 760 mg to about 1080 mg, about 780 mg to about 1080 mg, about 800 mg to about 1080 mg, about 820 mg to about 1080 mg, about 840 mg to about 1080 mg, about 860 mg to about 1080 mg, about 880 mg to about 1080 mg, about 900 mg to about 1080 mg, about 920 mg to about 1080 mg, about 940 mg to about 1080 mg, about 960 mg to about 1080 mg, about 980 mg to about 1080 mg, about 1000 mg to about 1080 mg, about 1020 mg to about 1080 mg, about 1040 mg to about 1080 mg, about 1060 mg to about 1080 mg, about 100 mg to about 1060 mg, about 120 mg to about 1060 mg, about 140 mg to about 1060 mg, about 160 mg to about 1060 mg, about 180 mg to about 1060 mg, about 200 mg to about 1060 mg, about 220 mg to about 1060 mg, about 240 mg to about 1060 mg, about 260 mg to about 1060 mg, about 280 mg to about 1060 mg, about 300 mg to about 1060 mg, about 320 mg to about 1060 mg, about 340 mg to about 1060 mg, about 360 mg to about 1060 mg, about 380 mg to about 1060 mg, about 400 mg to about 1060 mg, about 420 mg to about 1060 mg, about 440 mg to about 1060 mg, about 460 mg to about 1060 mg, about 480 mg to about 1060 mg, about 500 mg to about 1060 mg, about 520 mg to about 1060 mg, about 540 mg to about 1060 mg, about 560 mg to about 1060 mg, about 580 mg to about 1060 mg, about 600 mg to about 1060 mg, about 620 mg to about 1060 mg, about 640 mg to about 1060 mg, about 660 mg to about 1060 mg, about 680 mg to about 1060 mg, about 700 mg to about 1060 mg, about 720 mg to about 1060 mg, about 740 mg to about 1060 mg, about 760 mg to about 1060 mg, about 780 mg to about 1060 mg, about 800 mg to about 1060 mg, about 820 mg to about 1060 mg, about 840 mg to about 1060 mg, about 860 mg to about 1060 mg, about 880 mg to about 1060 mg, about 900 mg to about 1060 mg, about 920 mg to about 1060 mg, about 940 mg to about 1060 mg, about 960 mg to about 1060 mg, about 980 mg to about 1060 mg, about 1000 mg to about 1060 mg, about 1020 mg to about 1060 mg, about 1040 mg to about 1060 mg, about 100 mg to about 1040 mg, about 120 mg to about 1040 mg, about 140 mg to about 1040 mg, about 160 mg to about 1040 mg, about 180 mg to about 1040 mg, about 200 mg to about 1040 mg, about 220 mg to about 1040 mg, about 240 mg to about 1040 mg, about 260 mg to about 1040 mg, about 280 mg to about 1040 mg, about 300 mg to about 1040 mg, about 320 mg to about 1040 mg, about 340 mg to about 1040 mg, about 360 mg to about 1040 mg, about 380 mg to about 1040 mg, about 400 mg to about 1040 mg, about 420 mg to about 1040 mg, about 440 mg to about 1040 mg, about 460 mg to about 1040 mg, about 480 mg to about 1040 mg, about 500 mg to about 1040 mg, about 520 mg to about 1040 mg, about 540 mg to about 1040 mg, about 560 mg to about 1040 mg, about 580 mg to about 1040 mg, about 600 mg to about 1040 mg, about 620 mg to about 1040 mg, about 640 mg to about 1040 mg, about 660 mg to about 1040 mg, about 680 mg to about 1040 mg, about 700 mg to about 1040 mg, about 720 mg to about 1040 mg, about 740 mg to about 1040 mg, about 760 mg to about 1040 mg, about 780 mg to about 1040 mg, about 800 mg to about 1040 mg, about 820 mg to about 1040 mg, about 840 mg to about 1040 mg, about 860 mg to about 1040 mg, about 880 mg to about 1040 mg, about 900 mg to about 1040 mg, about 920 mg to about 1040 mg, about 940 mg to about 1040 mg, about 960 mg to about 1040 mg, about 980 mg to about 1040 mg, about 1000 mg to about 1040 mg, about 1020 mg to about 1040 mg, about 100 mg to about 1020 mg, about 120 mg to about 1020 mg, about 140 mg to about 1020 mg, about 160 mg to about 1020 mg, about 180 mg to about 1020 mg, about 200 mg to about 1020 mg, about 220 mg to about 1020 mg, about 240 mg to about 1020 mg, about 260 mg to about 1020 mg, about 280 mg to about 1020 mg, about 300 mg to about 1020 mg, about 320 mg to about 1020 mg, about 340 mg to about 1020 mg, about 360 mg to about 1020 mg, about 380 mg to about 1020 mg, about 400 mg to about 1020 mg, about 420 mg to about 1020 mg, about 440 mg to about 1020 mg, about 460 mg to about 1020 mg, about 480 mg to about 1020 mg, about 500 mg to about 1020 mg, about 520 mg to about 1020 mg, about 540 mg to about 1020 mg, about 560 mg to about 1020 mg, about 580 mg to about 1020 mg, about 600 mg to about 1020 mg, about 620 mg to about 1020 mg, about 640 mg to about 1020 mg, about 660 mg to about 1020 mg, about 680 mg to about 1020 mg, about 700 mg to about 1020 mg, about 720 mg to about 1020 mg, about 740 mg to about 1020 mg, about 760 mg to about 1020 mg, about 780 mg to about 1020 mg, about 800 mg to about 1020 mg, about 820 mg to about 1020 mg, about 840 mg to about 1020 mg, about 860 mg to about 1020 mg, about 880 mg to about 1020 mg, about 900 mg to about 1020 mg, about 920 mg to about 1020 mg, about 940 mg to about 1020 mg, about 960 mg to about 1020 mg, about 980 mg to about 1020 mg, about 1000 mg to about 1020 mg, about 100 mg to about 1000 mg, about 120 mg to about 1000 mg, about 140 mg to about 1000 mg, about 160 mg to about 1000 mg, about 180 mg to about 1000 mg, about 200 mg to about 1000 mg, about 220 mg to about 1000 mg, about 240 mg to about 1000 mg, about 260 mg to about 1000 mg, about 280 mg to about 1000 mg, about 300 mg to about 1000 mg, about 320 mg to about 1000 mg, about 340 mg to about 1000 mg, about 360 mg to about 1000 mg, about 380 mg to about 1000 mg, about 400 mg to about 1000 mg, about 420 mg to about 1000 mg, about 440 mg to about 1000 mg, about 460 mg to about 1000 mg, about 480 mg to about 1000 mg, about 500 mg to about 1000 mg, about 520 mg to about 1000 mg, about 540 mg to about 1000 mg, about 560 mg to about 1000 mg, about 580 mg to about 1000 mg, about 600 mg to about 1000 mg, about 620 mg to about 1000 mg, about 640 mg to about 1000 mg, about 660 mg to about 1000 mg, about 680 mg to about 1000 mg, about 700 mg to about 1000 mg, about 720 mg to about 1000 mg, about 740 mg to about 1000 mg, about 760 mg to about 1000 mg, about 780 mg to about 1000 mg, about 800 mg to about 1000 mg, about 820 mg to about 1000 mg, about 840 mg to about 1000 mg, about 860 mg to about 1000 mg, about 880 mg to about 1000 mg, about 900 mg to about 1000 mg, about 920 mg to about 1000 mg, about 940 mg to about 1000 mg, about 960 mg to about 1000 mg, about 980 mg to about 1000 mg, about 100 mg to about 980 mg, about 120 mg to about 980 mg, about 140 mg to about 980 mg, about 160 mg to about 980 mg, about 180 mg to about 980 mg, about 200 mg to about 980 mg, about 220 mg to about 980 mg, about 240 mg to about 980 mg, about 260 mg to about 980 mg, about 280 mg to about 980 mg, about 300 mg to about 980 mg, about 320 mg to about 980 mg, about 340 mg to about 980 mg, about 360 mg to about 980 mg, about 380 mg to about 980 mg, about 400 mg to about 980 mg, about 420 mg to about 980 mg, about 440 mg to about 980 mg, about 460 mg to about 980 mg, about 480 mg to about 980 mg, about 500 mg to about 980 mg, about 520 mg to about 980 mg, about 540 mg to about 980 mg, about 560 mg to about 980 mg, about 580 mg to about 980 mg, about 600 mg to about 980 mg, about 620 mg to about 980 mg, about 640 mg to about 980 mg, about 660 mg to about 980 mg, about 680 mg to about 980 mg, about 700 mg to about 980 mg, about 720 mg to about 980 mg, about 740 mg to about 980 mg, about 760 mg to about 980 mg, about 780 mg to about 980 mg, about 800 mg to about 980 mg, about 820 mg to about 980 mg, about 840 mg to about 980 mg, about 860 mg to about 980 mg, about 880 mg to about 980 mg, about 900 mg to about 980 mg, about 920 mg to about 980 mg, about 940 mg to about 980 mg, about 960 mg to about 980 mg, about 100 mg to about 960 mg, about 120 mg to about 960 mg, about 140 mg to about 960 mg, about 160 mg to about 960 mg, about 180 mg to about 960 mg, about 200 mg to about 960 mg, about 220 mg to about 960 mg, about 240 mg to about 960 mg, about 260 mg to about 960 mg, about 280 mg to about 960 mg, about 300 mg to about 960 mg, about 320 mg to about 960 mg, about 340 mg to about 960 mg, about 360 mg to about 960 mg, about 380 mg to about 960 mg, about 400 mg to about 960 mg, about 420 mg to about 960 mg, about 440 mg to about 960 mg, about 460 mg to about 960 mg, about 480 mg to about 960 mg, about 500 mg to about 960 mg, about 520 mg to about 960 mg, about 540 mg to about 960 mg, about 560 mg to about 960 mg, about 580 mg to about 960 mg, about 600 mg to about 960 mg, about 620 mg to about 960 mg, about 640 mg to about 960 mg, about 660 mg to about 960 mg, about 680 mg to about 960 mg, about 700 mg to about 960 mg, about 720 mg to about 960 mg, about 740 mg to about 960 mg, about 760 mg to about 960 mg, about 780 mg to about 960 mg, about 800 mg to about 960 mg, about 820 mg to about 960 mg, about 840 mg to about 960 mg, about 860 mg to about 960 mg, about 880 mg to about 960 mg, about 900 mg to about 960 mg, about 920 mg to about 960 mg, about 940 mg to about 960 mg, about 100 mg to about 940 mg, about 120 mg to about 940 mg, about 140 mg to about 940 mg, about 160 mg to about 940 mg, about 180 mg to about 940 mg, about 200 mg to about 940 mg, about 220 mg to about 940 mg, about 240 mg to about 940 mg, about 260 mg to about 940 mg, about 280 mg to about 940 mg, about 300 mg to about 940 mg, about 320 mg to about 940 mg, about 340 mg to about 940 mg, about 360 mg to about 940 mg, about 380 mg to about 940 mg, about 400 mg to about 940 mg, about 420 mg to about 940 mg, about 440 mg to about 940 mg, about 460 mg to about 940 mg, about 480 mg to about 940 mg, about 500 mg to about 940 mg, about 520 mg to about 940 mg, about 540 mg to about 940 mg, about 560 mg to about 940 mg, about 580 mg to about 940 mg, about 600 mg to about 940 mg, about 620 mg to about 940 mg, about 640 mg to about 940 mg, about 660 mg to about 940 mg, about 680 mg to about 940 mg, about 700 mg to about 940 mg, about 720 mg to about 940 mg, about 740 mg to about 940 mg, about 760 mg to about 940 mg, about 780 mg to about 940 mg, about 800 mg to about 940 mg, about 820 mg to about 940 mg, about 840 mg to about 940 mg, about 860 mg to about 940 mg, about 880 mg to about 940 mg, about 900 mg to about 940 mg, about 920 mg to about 940 mg, about 100 mg to about 920 mg, about 120 mg to about 920 mg, about 140 mg to about 920 mg, about 160 mg to about 920 mg, about 180 mg to about 920 mg, about 200 mg to about 920 mg, about 220 mg to about 920 mg, about 240 mg to about 920 mg, about 260 mg to about 920 mg, about 280 mg to about 920 mg, about 300 mg to about 920 mg, about 320 mg to about 920 mg, about 340 mg to about 920 mg, about 360 mg to about 920 mg, about 380 mg to about 920 mg, about 400 mg to about 920 mg, about 420 mg to about 920 mg, about 440 mg to about 920 mg, about 460 mg to about 920 mg, about 480 mg to about 920 mg, about 500 mg to about 920 mg, about 520 mg to about 920 mg, about 540 mg to about 920 mg, about 560 mg to about 920 mg, about 580 mg to about 920 mg, about 600 mg to about 920 mg, about 620 mg to about 920 mg, about 640 mg to about 920 mg, about 660 mg to about 920 mg, about 680 mg to about 920 mg, about 700 mg to about 920 mg, about 720 mg to about 920 mg, about 740 mg to about 920 mg, about 760 mg to about 920 mg, about 780 mg to about 920 mg, about 800 mg to about 920 mg, about 820 mg to about 920 mg, about 840 mg to about 920 mg, about 860 mg to about 920 mg, about 880 mg to about 920 mg, about 900 mg to about 920 mg, about 100 mg to about 900 mg, about 120 mg to about 900 mg, about 140 mg to about 900 mg, about 160 mg to about 900 mg, about 180 mg to about 900 mg, about 200 mg to about 900 mg, about 220 mg to about 900 mg, about 240 mg to about 900 mg, about 260 mg to about 900 mg, about 280 mg to about 900 mg, about 300 mg to about 900 mg, about 320 mg to about 900 mg, about 340 mg to about 900 mg, about 360 mg to about 900 mg, about 380 mg to about 900 mg, about 400 mg to about 900 mg, about 420 mg to about 900 mg, about 440 mg to about 900 mg, about 460 mg to about 900 mg, about 480 mg to about 900 mg, about 500 mg to about 900 mg, about 520 mg to about 900 mg, about 540 mg to about 900 mg, about 560 mg to about 900 mg, about 580 mg to about 900 mg, about 600 mg to about 900 mg, about 620 mg to about 900 mg, about 640 mg to about 900 mg, about 660 mg to about 900 mg, about 680 mg to about 900 mg, about 700 mg to about 900 mg, about 720 mg to about 900 mg, about 740 mg to about 900 mg, about 760 mg to about 900 mg, about 780 mg to about 900 mg, about 800 mg to about 900 mg, about 820 mg to about 900 mg, about 840 mg to about 900 mg, about 860 mg to about 900 mg, about 880 mg to about 900 mg, about 100 mg to about 880 mg, about 120 mg to about 880 mg, about 140 mg to about 880 mg, about 160 mg to about 880 mg, about 180 mg to about 880 mg, about 200 mg to about 880 mg, about 220 mg to about 880 mg, about 240 mg to about 880 mg, about 260 mg to about 880 mg, about 280 mg to about 880 mg, about 300 mg to about 880 mg, about 320 mg to about 880 mg, about 340 mg to about 880 mg, about 360 mg to about 880 mg, about 380 mg to about 880 mg, about 400 mg to about 880 mg, about 420 mg to about 880 mg, about 440 mg to about 880 mg, about 460 mg to about 880 mg, about 480 mg to about 880 mg, about 500 mg to about 880 mg, about 520 mg to about 880 mg, about 540 mg to about 880 mg, about 560 mg to about 880 mg, about 580 mg to about 880 mg, about 600 mg to about 880 mg, about 620 mg to about 880 mg, about 640 mg to about 880 mg, about 660 mg to about 880 mg, about 680 mg to about 880 mg, about 700 mg to about 880 mg, about 720 mg to about 880 mg, about 740 mg to about 880 mg, about 760 mg to about 880 mg, about 780 mg to about 880 mg, about 800 mg to about 880 mg, about 820 mg to about 880 mg, about 840 mg to about 880 mg, about 860 mg to about 880 mg, about 100 mg to about 860 mg, about 120 mg to about 860 mg, about 140 mg to about 860 mg, about 160 mg to about 860 mg, about 180 mg to about 860 mg, about 200 mg to about 860 mg, about 220 mg to about 860 mg, about 240 mg to about 860 mg, about 260 mg to about 860 mg, about 280 mg to about 860 mg, about 300 mg to about 860 mg, about 320 mg to about 860 mg, about 340 mg to about 860 mg, about 360 mg to about 860 mg, about 380 mg to about 860 mg, about 400 mg to about 860 mg, about 420 mg to about 860 mg, about 440 mg to about 860 mg, about 460 mg to about 860 mg, about 480 mg to about 860 mg, about 500 mg to about 860 mg, about 520 mg to about 860 mg, about 540 mg to about 860 mg, about 560 mg to about 860 mg, about 580 mg to about 860 mg, about 600 mg to about 860 mg, about 620 mg to about 860 mg, about 640 mg to about 860 mg, about 660 mg to about 860 mg, about 680 mg to about 860 mg, about 700 mg to about 860 mg, about 720 mg to about 860 mg, about 740 mg to about 860 mg, about 760 mg to about 860 mg, about 780 mg to about 860 mg, about 800 mg to about 860 mg, about 820 mg to about 860 mg, about 840 mg to about 860 mg, about 100 mg to about 840 mg, about 120 mg to about 840 mg, about 140 mg to about 840 mg, about 160 mg to about 840 mg, about 180 mg to about 840 mg, about 200 mg to about 840 mg, about 220 mg to about 840 mg, about 240 mg to about 840 mg, about 260 mg to about 840 mg, about 280 mg to about 840 mg, about 300 mg to about 840 mg, about 320 mg to about 840 mg, about 340 mg to about 840 mg, about 360 mg to about 840 mg, about 380 mg to about 840 mg, about 400 mg to about 840 mg, about 420 mg to about 840 mg, about 440 mg to about 840 mg, about 460 mg to about 840 mg, about 480 mg to about 840 mg, about 500 mg to about 840 mg, about 520 mg to about 840 mg, about 540 mg to about 840 mg, about 560 mg to about 840 mg, about 580 mg to about 840 mg, about 600 mg to about 840 mg, about 620 mg to about 840 mg, about 640 mg to about 840 mg, about 660 mg to about 840 mg, about 680 mg to about 840 mg, about 700 mg to about 840 mg, about 720 mg to about 840 mg, about 740 mg to about 840 mg, about 760 mg to about 840 mg, about 780 mg to about 840 mg, about 800 mg to about 840 mg, about 820 mg to about 840 mg, about 100 mg to about 820 mg, about 120 mg to about 820 mg, about 140 mg to about 820 mg, about 160 mg to about 820 mg, about 180 mg to about 820 mg, about 200 mg to about 820 mg, about 220 mg to about 820 mg, about 240 mg to about 820 mg, about 260 mg to about 820 mg, about 280 mg to about 820 mg, about 300 mg to about 820 mg, about 320 mg to about 820 mg, about 340 mg to about 820 mg, about 360 mg to about 820 mg, about 380 mg to about 820 mg, about 400 mg to about 820 mg, about 420 mg to about 820 mg, about 440 mg to about 820 mg, about 460 mg to about 820 mg, about 480 mg to about 820 mg, about 500 mg to about 820 mg, about 520 mg to about 820 mg, about 540 mg to about 820 mg, about 560 mg to about 820 mg, about 580 mg to about 820 mg, about 600 mg to about 820 mg, about 620 mg to about 820 mg, about 640 mg to about 820 mg, about 660 mg to about 820 mg, about 680 mg to about 820 mg, about 700 mg to about 820 mg, about 720 mg to about 820 mg, about 740 mg to about 820 mg, about 760 mg to about 820 mg, about 780 mg to about 820 mg, about 800 mg to about 820 mg, about 100 mg to about 800 mg, about 120 mg to about 800 mg, about 140 mg to about 800 mg, about 160 mg to about 800 mg, about 180 mg to about 800 mg, about 200 mg to about 800 mg, about 220 mg to about 800 mg, about 240 mg to about 800 mg, about 260 mg to about 800 mg, about 280 mg to about 800 mg, about 300 mg to about 800 mg, about 320 mg to about 800 mg, about 340 mg to about 800 mg, about 360 mg to about 800 mg, about 380 mg to about 800 mg, about 400 mg to about 800 mg, about 420 mg to about 800 mg, about 440 mg to about 800 mg, about 460 mg to about 800 mg, about 480 mg to about 800 mg, about 500 mg to about 800 mg, about 520 mg to about 800 mg, about 540 mg to about 800 mg, about 560 mg to about 800 mg, about 580 mg to about 800 mg, about 600 mg to about 800 mg, about 620 mg to about 800 mg, about 640 mg to about 800 mg, about 660 mg to about 800 mg, about 680 mg to about 800 mg, about 700 mg to about 800 mg, about 720 mg to about 800 mg, about 740 mg to about 800 mg, about 760 mg to about 800 mg, about 780 mg to about 800 mg, about 100 mg to about 780 mg, about 120 mg to about 780 mg, about 140 mg to about 780 mg, about 160 mg to about 780 mg, about 180 mg to about 780 mg, about 200 mg to about 780 mg, about 220 mg to about 780 mg, about 240 mg to about 780 mg, about 260 mg to about 780 mg, about 280 mg to about 780 mg, about 300 mg to about 780 mg, about 320 mg to about 780 mg, about 340 mg to about 780 mg, about 360 mg to about 780 mg, about 380 mg to about 780 mg, about 400 mg to about 780 mg, about 420 mg to about 780 mg, about 440 mg to about 780 mg, about 460 mg to about 780 mg, about 480 mg to about 780 mg, about 500 mg to about 780 mg, about 520 mg to about 780 mg, about 540 mg to about 780 mg, about 560 mg to about 780 mg, about 580 mg to about 780 mg, about 600 mg to about 780 mg, about 620 mg to about 780 mg, about 640 mg to about 780 mg, about 660 mg to about 780 mg, about 680 mg to about 780 mg, about 700 mg to about 780 mg, about 720 mg to about 780 mg, about 740 mg to about 780 mg, about 760 mg to about 780 mg, about 100 mg to about 760 mg, about 120 mg to about 760 mg, about 140 mg to about 760 mg, about 160 mg to about 760 mg, about 180 mg to about 760 mg, about 200 mg to about 760 mg, about 220 mg to about 760 mg, about 240 mg to about 760 mg, about 260 mg to about 760 mg, about 280 mg to about 760 mg, about 300 mg to about 760 mg, about 320 mg to about 760 mg, about 340 mg to about 760 mg, about 360 mg to about 760 mg, about 380 mg to about 760 mg, about 400 mg to about 760 mg, about 420 mg to about 760 mg, about 440 mg to about 760 mg, about 460 mg to about 760 mg, about 480 mg to about 760 mg, about 500 mg to about 760 mg, about 520 mg to about 760 mg, about 540 mg to about 760 mg, about 560 mg to about 760 mg, about 580 mg to about 760 mg, about 600 mg to about 760 mg, about 620 mg to about 760 mg, about 640 mg to about 760 mg, about 660 mg to about 760 mg, about 680 mg to about 760 mg, about 700 mg to about 760 mg, about 720 mg to about 760 mg, about 740 mg to about 760 mg, about 100 mg to about 740 mg, about 120 mg to about 740 mg, about 140 mg to about 740 mg, about 160 mg to about 740 mg, about 180 mg to about 740 mg, about 200 mg to about 740 mg, about 220 mg to about 740 mg, about 240 mg to about 740 mg, about 260 mg to about 740 mg, about 280 mg to about 740 mg, about 300 mg to about 740 mg, about 320 mg to about 740 mg, about 340 mg to about 740 mg, about 360 mg to about 740 mg, about 380 mg to about 740 mg, about 400 mg to about 740 mg, about 420 mg to about 740 mg, about 440 mg to about 740 mg, about 460 mg to about 740 mg, about 480 mg to about 740 mg, about 500 mg to about 740 mg, about 520 mg to about 740 mg, about 540 mg to about 740 mg, about 560 mg to about 740 mg, about 580 mg to about 740 mg, about 600 mg to about 740 mg, about 620 mg to about 740 mg, about 640 mg to about 740 mg, about 660 mg to about 740 mg, about 680 mg to about 740 mg, about 700 mg to about 740 mg, about 720 mg to about 740 mg, about 100 mg to about 720 mg, about 120 mg to about 720 mg, about 140 mg to about 720 mg, about 160 mg to about 720 mg, about 180 mg to about 720 mg, about 200 mg to about 720 mg, about 220 mg to about 720 mg, about 240 mg to about 720 mg, about 260 mg to about 720 mg, about 280 mg to about 720 mg, about 300 mg to about 720 mg, about 320 mg to about 720 mg, about 340 mg to about 720 mg, about 360 mg to about 720 mg, about 380 mg to about 720 mg, about 400 mg to about 720 mg, about 420 mg to about 720 mg, about 440 mg to about 720 mg, about 460 mg to about 720 mg, about 480 mg to about 720 mg, about 500 mg to about 720 mg, about 520 mg to about 720 mg, about 540 mg to about 720 mg, about 560 mg to about 720 mg, about 580 mg to about 720 mg, about 600 mg to about 720 mg, about 620 mg to about 720 mg, about 640 mg to about 720 mg, about 660 mg to about 720 mg, about 680 mg to about 720 mg, about 700 mg to about 720 mg, about 100 mg to about 700 mg, about 120 mg to about 700 mg, about 140 mg to about 700 mg, about 160 mg to about 700 mg, about 180 mg to about 700 mg, about 200 mg to about 700 mg, about 220 mg to about 700 mg, about 240 mg to about 700 mg, about 260 mg to about 700 mg, about 280 mg to about 700 mg, about 300 mg to about 700 mg, about 320 mg to about 700 mg, about 340 mg to about 700 mg, about 360 mg to about 700 mg, about 380 mg to about 700 mg, about 400 mg to about 700 mg, about 420 mg to about 700 mg, about 440 mg to about 700 mg, about 460 mg to about 700 mg, about 480 mg to about 700 mg, about 500 mg to about 700 mg, about 520 mg to about 700 mg, about 540 mg to about 700 mg, about 560 mg to about 700 mg, about 580 mg to about 700 mg, about 600 mg to about 700 mg, about 620 mg to about 700 mg, about 640 mg to about 700 mg, about 660 mg to about 700 mg, about 680 mg to about 700 mg, about 100 mg to about 680 mg, about 120 mg to about 680 mg, about 140 mg to about 680 mg, about 160 mg to about 680 mg, about 180 mg to about 680 mg, about 200 mg to about 680 mg, about 220 mg to about 680 mg, about 240 mg to about 680 mg, about 260 mg to about 680 mg, about 280 mg to about 680 mg, about 300 mg to about 680 mg, about 320 mg to about 680 mg, about 340 mg to about 680 mg, about 360 mg to about 680 mg, about 380 mg to about 680 mg, about 400 mg to about 680 mg, about 420 mg to about 680 mg, about 440 mg to about 680 mg, about 460 mg to about 680 mg, about 480 mg to about 680 mg, about 500 mg to about 680 mg, about 520 mg to about 680 mg, about 540 mg to about 680 mg, about 560 mg to about 680 mg, about 580 mg to about 680 mg, about 600 mg to about 680 mg, about 620 mg to about 680 mg, about 640 mg to about 680 mg, about 660 mg to about 680 mg, about 100 mg to about 660 mg, about 120 mg to about 660 mg, about 140 mg to about 660 mg, about 160 mg to about 660 mg, about 180 mg to about 660 mg, about 200 mg to about 660 mg, about 220 mg to about 660 mg, about 240 mg to about 660 mg, about 260 mg to about 660 mg, about 280 mg to about 660 mg, about 300 mg to about 660 mg, about 320 mg to about 660 mg, about 340 mg to about 660 mg, about 360 mg to about 660 mg, about 380 mg to about 660 mg, about 400 mg to about 660 mg, about 420 mg to about 660 mg, about 440 mg to about 660 mg, about 460 mg to about 660 mg, about 480 mg to about 660 mg, about 500 mg to about 660 mg, about 520 mg to about 660 mg, about 540 mg to about 660 mg, about 560 mg to about 660 mg, about 580 mg to about 660 mg, about 600 mg to about 660 mg, about 620 mg to about 660 mg, about 640 mg to about 660 mg, about 100 mg to about 640 mg, about 120 mg to about 640 mg, about 140 mg to about 640 mg, about 160 mg to about 640 mg, about 180 mg to about 640 mg, about 200 mg to about 640 mg, about 220 mg to about 640 mg, about 240 mg to about 640 mg, about 260 mg to about 640 mg, about 280 mg to about 640 mg, about 300 mg to about 640 mg, about 320 mg to about 640 mg, about 340 mg to about 640 mg, about 360 mg to about 640 mg, about 380 mg to about 640 mg, about 400 mg to about 640 mg, about 420 mg to about 640 mg, about 440 mg to about 640 mg, about 460 mg to about 640 mg, about 480 mg to about 640 mg, about 500 mg to about 640 mg, about 520 mg to about 640 mg, about 540 mg to about 640 mg, about 560 mg to about 640 mg, about 580 mg to about 640 mg, about 600 mg to about 640 mg, about 620 mg to about 640 mg, about 100 mg to about 620 mg, about 120 mg to about 620 mg, about 140 mg to about 620 mg, about 160 mg to about 620 mg, about 180 mg to about 620 mg, about 200 mg to about 620 mg, about 220 mg to about 620 mg, about 240 mg to about 620 mg, about 260 mg to about 620 mg, about 280 mg to about 620 mg, about 300 mg to about 620 mg, about 320 mg to about 620 mg, about 340 mg to about 620 mg, about 360 mg to about 620 mg, about 380 mg to about 620 mg, about 400 mg to about 620 mg, about 420 mg to about 620 mg, about 440 mg to about 620 mg, about 460 mg to about 620 mg, about 480 mg to about 620 mg, about 500 mg to about 620 mg, about 520 mg to about 620 mg, about 540 mg to about 620 mg, about 560 mg to about 620 mg, about 580 mg to about 620 mg, about 600 mg to about 620 mg, about 100 mg to about 600 mg, about 120 mg to about 600 mg, about 140 mg to about 600 mg, about 160 mg to about 600 mg, about 180 mg to about 600 mg, about 200 mg to about 600 mg, about 220 mg to about 600 mg, about 240 mg to about 600 mg, about 260 mg to about 600 mg, about 280 mg to about 600 mg, about 300 mg to about 600 mg, about 320 mg to about 600 mg, about 340 mg to about 600 mg, about 360 mg to about 600 mg, about 380 mg to about 600 mg, about 400 mg to about 600 mg, about 420 mg to about 600 mg, about 440 mg to about 600 mg, about 460 mg to about 600 mg, about 480 mg to about 600 mg, about 500 mg to about 600 mg, about 520 mg to about 600 mg, about 540 mg to about 600 mg, about 560 mg to about 600 mg, about 580 mg to about 600 mg, about 100 mg to about 580 mg, about 120 mg to about 580 mg, about 140 mg to about 580 mg, about 160 mg to about 580 mg, about 180 mg to about 580 mg, about 200 mg to about 580 mg, about 220 mg to about 580 mg, about 240 mg to about 580 mg, about 260 mg to about 580 mg, about 280 mg to about 580 mg, about 300 mg to about 580 mg, about 320 mg to about 580 mg, about 340 mg to about 580 mg, about 360 mg to about 580 mg, about 380 mg to about 580 mg, about 400 mg to about 580 mg, about 420 mg to about 580 mg, about 440 mg to about 580 mg, about 460 mg to about 580 mg, about 480 mg to about 580 mg, about 500 mg to about 580 mg, about 520 mg to about 580 mg, about 540 mg to about 580 mg, about 560 mg to about 580 mg, about 100 mg to about 560 mg, about 120 mg to about 560 mg, about 140 mg to about 560 mg, about 160 mg to about 560 mg, about 180 mg to about 560 mg, about 200 mg to about 560 mg, about 220 mg to about 560 mg, about 240 mg to about 560 mg, about 260 mg to about 560 mg, about 280 mg to about 560 mg, about 300 mg to about 560 mg, about 320 mg to about 560 mg, about 340 mg to about 560 mg, about 360 mg to about 560 mg, about 380 mg to about 560 mg, about 400 mg to about 560 mg, about 420 mg to about 560 mg, about 440 mg to about 560 mg, about 460 mg to about 560 mg, about 480 mg to about 560 mg, about 500 mg to about 560 mg, about 520 mg to about 560 mg, about 540 mg to about 560 mg, about 100 mg to about 540 mg, about 120 mg to about 540 mg, about 140 mg to about 540 mg, about 160 mg to about 540 mg, about 180 mg to about 540 mg, about 200 mg to about 540 mg, about 220 mg to about 540 mg, about 240 mg to about 540 mg, about 260 mg to about 540 mg, about 280 mg to about 540 mg, about 300 mg to about 540 mg, about 320 mg to about 540 mg, about 340 mg to about 540 mg, about 360 mg to about 540 mg, about 380 mg to about 540 mg, about 400 mg to about 540 mg, about 420 mg to about 540 mg, about 440 mg to about 540 mg, about 460 mg to about 540 mg, about 480 mg to about 540 mg, about 500 mg to about 540 mg, about 520 mg to about 540 mg, about 100 mg to about 520 mg, about 120 mg to about 520 mg, about 140 mg to about 520 mg, about 160 mg to about 520 mg, about 180 mg to about 520 mg, about 200 mg to about 520 mg, about 220 mg to about 520 mg, about 240 mg to about 520 mg, about 260 mg to about 520 mg, about 280 mg to about 520 mg, about 300 mg to about 520 mg, about 320 mg to about 520 mg, about 340 mg to about 520 mg, about 360 mg to about 520 mg, about 380 mg to about 520 mg, about 400 mg to about 520 mg, about 420 mg to about 520 mg, about 440 mg to about 520 mg, about 460 mg to about 520 mg, about 480 mg to about 520 mg, about 500 mg to about 520 mg, about 100 mg to about 500 mg, about 120 mg to about 500 mg, about 140 mg to about 500 mg, about 160 mg to about 500 mg, about 180 mg to about 500 mg, about 200 mg to about 500 mg, about 220 mg to about 500 mg, about 240 mg to about 500 mg, about 260 mg to about 500 mg, about 280 mg to about 500 mg, about 300 mg to about 500 mg, about 320 mg to about 500 mg, about 340 mg to about 500 mg, about 360 mg to about 500 mg, about 380 mg to about 500 mg, about 400 mg to about 500 mg, about 420 mg to about 500 mg, about 440 mg to about 500 mg, about 460 mg to about 500 mg, about 480 mg to about 500 mg, about 100 mg to about 480 mg, about 120 mg to about 480 mg, about 140 mg to about 480 mg, about 160 mg to about 480 mg, about 180 mg to about 480 mg, about 200 mg to about 480 mg, about 220 mg to about 480 mg, about 240 mg to about 480 mg, about 260 mg to about 480 mg, about 280 mg to about 480 mg, about 300 mg to about 480 mg, about 320 mg to about 480 mg, about 340 mg to about 480 mg, about 360 mg to about 480 mg, about 380 mg to about 480 mg, about 400 mg to about 480 mg, about 420 mg to about 480 mg, about 440 mg to about 480 mg, about 460 mg to about 480 mg, about 100 mg to about 460 mg, about 120 mg to about 460 mg, about 140 mg to about 460 mg, about 160 mg to about 460 mg, about 180 mg to about 460 mg, about 200 mg to about 460 mg, about 220 mg to about 460 mg, about 240 mg to about 460 mg, about 260 mg to about 460 mg, about 280 mg to about 460 mg, about 300 mg to about 460 mg, about 320 mg to about 460 mg, about 340 mg to about 460 mg, about 360 mg to about 460 mg, about 380 mg to about 460 mg, about 400 mg to about 460 mg, about 420 mg to about 460 mg, about 440 mg to about 460 mg, about 100 mg to about 440 mg, about 120 mg to about 440 mg, about 140 mg to about 440 mg, about 160 mg to about 440 mg, about 180 mg to about 440 mg, about 200 mg to about 440 mg, about 220 mg to about 440 mg, about 240 mg to about 440 mg, about 260 mg to about 440 mg, about 280 mg to about 440 mg, about 300 mg to about 440 mg, about 320 mg to about 440 mg, about 340 mg to about 440 mg, about 360 mg to about 440 mg, about 380 mg to about 440 mg, about 400 mg to about 440 mg, about 420 mg to about 440 mg, about 100 mg to about 420 mg, about 120 mg to about 420 mg, about 140 mg to about 420 mg, about 160 mg to about 420 mg, about 180 mg to about 420 mg, about 200 mg to about 420 mg, about 220 mg to about 420 mg, about 240 mg to about 420 mg, about 260 mg to about 420 mg, about 280 mg to about 420 mg, about 300 mg to about 420 mg, about 320 mg to about 420 mg, about 340 mg to about 420 mg, about 360 mg to about 420 mg, about 380 mg to about 420 mg, about 400 mg to about 420 mg, about 100 mg to about 400 mg, about 120 mg to about 400 mg, about 140 mg to about 400 mg, about 160 mg to about 400 mg, about 180 mg to about 400 mg, about 200 mg to about 400 mg, about 220 mg to about 400 mg, about 240 mg to about 400 mg, about 260 mg to about 400 mg, about 280 mg to about 400 mg, about 300 mg to about 400 mg, about 320 mg to about 400 mg, about 340 mg to about 400 mg, about 360 mg to about 400 mg, about 380 mg to about 400 mg, about 100 mg to about 380 mg, about 120 mg to about 380 mg, about 140 mg to about 380 mg, about 160 mg to about 380 mg, about 180 mg to about 380 mg, about 200 mg to about 380 mg, about 220 mg to about 380 mg, about 240 mg to about 380 mg, about 260 mg to about 380 mg, about 280 mg to about 380 mg, about 300 mg to about 380 mg, about 320 mg to about 380 mg, about 340 mg to about 380 mg, about 360 mg to about 380 mg, about 100 mg to about 360 mg, about 120 mg to about 360 mg, about 140 mg to about 360 mg, about 160 mg to about 360 mg, about 180 mg to about 360 mg, about 200 mg to about 360 mg, about 220 mg to about 360 mg, about 240 mg to about 360 mg, about 260 mg to about 360 mg, about 280 mg to about 360 mg, about 300 mg to about 360 mg, about 320 mg to about 360 mg, about 340 mg to about 360 mg, about 100 mg to about 340 mg, about 120 mg to about 340 mg, about 140 mg to about 340 mg, about 160 mg to about 340 mg, about 180 mg to about 340 mg, about 200 mg to about 340 mg, about 220 mg to about 340 mg, about 240 mg to about 340 mg, about 260 mg to about 340 mg, about 280 mg to about 340 mg, about 300 mg to about 340 mg, about 320 mg to about 340 mg, about 100 mg to about 320 mg, about 120 mg to about 320 mg, about 140 mg to about 320 mg, about 160 mg to about 320 mg, about 180 mg to about 320 mg, about 200 mg to about 320 mg, about 220 mg to about 320 mg, about 240 mg to about 320 mg, about 260 mg to about 320 mg, about 280 mg to about 320 mg, about 300 mg to about 320 mg, about 100 mg to about 300 mg, about 120 mg to about 300 mg, about 140 mg to about 300 mg, about 160 mg to about 300 mg, about 180 mg to about 300 mg, about 200 mg to about 300 mg, about 220 mg to about 300 mg, about 240 mg to about 300 mg, about 260 mg to about 300 mg, about 280 mg to about 300 mg, about 100 mg to about 280 mg, about 120 mg to about 280 mg, about 140 mg to about 280 mg, about 160 mg to about 280 mg, about 180 mg to about 280 mg, about 200 mg to about 280 mg, about 220 mg to about 280 mg, about 240 mg to about 280 mg, about 260 mg to about 280 mg, about 100 mg to about 260 mg, about 120 mg to about 260 mg, about 140 mg to about 260 mg, about 160 mg to about 260 mg, about 180 mg to about 260 mg, about 200 mg to about 260 mg, about 220 mg to about 260 mg, about 240 mg to about 260 mg, about 100 mg to about 240 mg, about 120 mg to about 240 mg, about 140 mg to about 240 mg, about 160 mg to about 240 mg, about 180 mg to about 240 mg, about 200 mg to about 240 mg, about 220 mg to about 240 mg, about 100 mg to about 220 mg, about 120 mg to about 220 mg, about 140 mg to about 220 mg, about 160 mg to about 220 mg, about 180 mg to about 220 mg, about 200 mg to about 220 mg, about 100 mg to about 200 mg, about 120 mg to about 200 mg, about 140 mg to about 200 mg, about 160 mg to about 200 mg, about 180 mg to about 200 mg, about 100 mg to about 180 mg, about 120 mg to about 180 mg, about 140 mg to about 180 mg, about 160 mg to about 180 mg, about 100 mg to about 160 mg, about 120 mg to about 160 mg, about 140 mg to about 160 mg, about 100 mg to about 140 mg, about 120 mg to about 140 mg, or about 100 mg to about 120 mg of the anti-IL-13 antibody, or antigen-binding portion thereof.

In one embodiment, the composition of the disclosure is administered once. In another embodiment, the composition is administered weekly. In another embodiment, the composition is administered for two weeks. In another embodiment, the composition is administered for three weeks. In another embodiment, the composition is administered for four weeks, five weeks, six weeks, seven weeks, eight weeks, nine weeks, ten weeks, eleven weeks, three months, four months, five months, six months, seven months, eight months, nine months, ten months, eleven months, twelve months, thirteen months, fourteen months, fifteen months, sixteen months, seventeen months, eighteen months, nineteen months, twenty months, twenty-one months, twenty-two months, twenty-three months, two years, three years, four years, five years, ten years, for the duration of the disease, or for the life of the subject. In one embodiment, the composition is administered subcutaneously. In another embodiment, the composition is administered intravenously. In one embodiment, the composition is administered intravenously for one administration, followed by weekly subcutaneous dosages.

The dose of the pharmaceutical compositions may be altered depending on the age, sex, health, and weight of the recipient, kind of concurrent treatment, if any, frequency of treatment, and the nature of the effect desired. Formulation used as preclinical and clinical therapeutics or in clinical diagnostics may be produced by those of skill, employing accepted principles of diagnosis and treatment. The dose ranges for the compositions may be large enough to produce the desired effect. Likewise, the dose of the diagnostic composition may be altered depending on the nature of the diagnosis, e.g., in vitro versus in vivo application. Methods of formulating the IL-13 antibodies, and antigen-binding portions thereof, into diagnostic agents, e.g., chelating an antibody to a diagnostic agent selected from a radio label, a colorimetric moiety, a fluorescent moiety, a chemiluminescent moiety, an enzymatic moiety, and immunogenic moiety, are known in the art.

The aforementioned compositions and pharmaceutical preparations may be packaged in the form of kits. The term "kit" as used herein refers to a packaged product comprising components with which to administer the anti-IL-13 antibody of the disclosure for treatment of AD. The kit, in some embodiments, comprises a box or container that holds the components of the kit. The box or container is affixed with a label or a Food and Drug Administration approved protocol. The box or container holds components of the disclosure which are, in some embodiments, contained within plastic, polyethylene, polypropylene, ethylene, or propylene vessels. The vessels can be capped-tubes or bottles. The kit can also include instructions for administering an anti-IL-13 antibody.

Combination Therapies

The term "combination therapy", as used herein, refers to the administration of two or more therapeutic substances, e.g., an anti-IL-13 antibody and another agent. The other drug(s) may be administered concomitant with, prior to, or following the administration of the anti-IL-13 antibody. Particularly, the additional agent is an agent that is useful in the diagnosis and/or therapy of dermatitis disorders.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present disclosure, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed stepwise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

Atopic Dermatitis

"Atopic Dermatitis", "AD", or "eczema", as used herein, refers to an inflammatory disease characterized by chronic inflammation of the skin. Symptoms of AD include, but are not limited to, pruritus (itchy skin and/or an itch sensation), dry skin, itching, which may be severe especially at night, red to brownish-gray patches of skin especially on the hands, feet, ankles, wrists, neck, upper chest, eyelids, inside the bend of the elbows and knees, and in infants, the face and scalp, small, raised bumps which may leak fluid and crust over when scratched, thickened skin, cracked skin, scaly skin, raw skin, skin sensitivity, swollen skin, and interruption and/or loss of sleep. AD most often begins before age 5 and may persist into adolescence and adulthood. In some patients, AD flares up periodically followed by periods of clearance that may last several years.

As used herein, the terms "treat", "treating", or the like, mean to alleviate symptoms, eliminate the causation of symptoms either on a temporary or permanent basis, or to prevent or slow the appearance of symptoms of AD. In certain embodiments, the present methods are useful for reducing the incidence of symptoms or indications associated with AD. Particular embodiments of the disclosure relate to methods for treating or ameliorating at least one symptom or indication associated with AD.

Specifically, the present methods are useful for treating or ameliorating at least one symptom or indication of AD. The symptoms or indications associated with AD that are treatable in accordance with this embodiment include, but are not limited to, pruritus; dry skin; itching; red to brownish-gray patches of skin; small, raised bumps which may leak fluid and crust over when scratched; thickened skin; cracked skin; scaly skin; raw skin; skin sensitivity; and swollen skin.

In embodiments directed to therapy of AD, the methods of the present disclosure comprise treating subjects with elevated levels of AD-associated markers. Examples of AD-associated markers include, but are not limited to, for example, peripheral blood eosinophils, Immunoglobulin E (IgE), lactate dehydrogenase, IL-13, IL-22, chemokine (C-C motif) ligand 17 (CCL17)/thymus- and activation-regulated chemokine (TARC), and chemokine (C-C motif) ligand 18 (CCL18)/pulmonary and activation-regulated chemokine (PARC).

In some embodiments, the subject or patient is an animal, in some embodiments a mammal or a bird. In some embodiments, the subject is selected from the group consisting of humans, dogs, cats, pigs, cows, buffalo and horses. In some embodiments, the subject is a human subject.

In some embodiments, the methods herein may be used to treat AD in child subjects who are less than 3 years old. For example, the present methods may be used to treat infant subjects who are less than 1 month, 2 months, 3 months, 4 months, 5 months, 6 months, 7 months, 8 months, 9 months, 10 months, 11 months or less than 12 months old. In other embodiments, the methods of the present disclosure may be used to treat children who are more than 3 years old, more than 4 years, 5 years, 6 years, 7 years, 8 years, 9 years, 10 years, 11 years, 12 years, 13 years, 14 years, or more than 15 years old (including all ages in between).

In related embodiments, the methods herein may be used to treat AD in adult subjects. By "adults," it is meant that the subject is at least 16 years old, which includes, a subject whose age is, for example, 16 years, 17 years, 18 years, 19 years, 20 years, 25 years, 30 years, 40 years, 50 years, 60 years, 70 years, 80 years, 90 years, or greater (including all ages in between).

In some embodiments, disclosed herein are methods for treating or ameliorating at least one symptom of AD in a subject in need thereof, comprising first selecting a subject who exhibits at least one symptom associated with AD, and administering a therapeutically effective amount of an anti-IL-13 antibody, or antigen-binding portion thereof, to the subject.

Selection of Subjects

In some embodiments, a method disclosed herein comprises first selecting a subject who has AD. In some embodiments, a method disclosed herein comprises first selecting a subject who has been diagnosed with AD. The second step comprises administering a composition of the instant disclosure comprising an anti-IL-13 antibody, or antigen-binding portion thereof.

In the context of the present embodiment, the selection step may be used to identify a subset of population which is more susceptible to the eosinophilic disorder. In these embodiments, the subject may display a particular trait or condition associated with the eosinophilic disorder. For example, a subject in need thereof may include a subject suffering from AD.

In other embodiments, the selection step may be used to identify a subset of population which is more likely to benefit from the therapy with the anti-IL-13 antibody, or antigen-binding portion thereof. An example of such a subset of population is AD patients who have an intolerance or inadequate response to treatment with topical medications for at least four weeks or who have required at least one systemic therapy to control AD.

In the therapeutic embodiments additionally including selection of a susceptible subject population, the methods may comprise implementing one or more reagents and/or tools for detecting disease-specific markers associated with AD. For instance, AD-associated markers may include protein markers such as elevated or reduced IgE, lactate dehydrogenase, IL-13, IL-22, TARC, or PARC. A combination of the aforementioned markers, e.g., a biomarker and a physiological marker, may also be employed.

Embodiments of the disclosure is directed to treatment of treatment-naive as well as previously-treated subjects. The subjects may include responders, non-responders, refractory or relapsed subjects.

The term "treatment-naïve" is meant to include subjects who have never been actively treated for AD. Existing modes of therapy of AD include, e.g., topical therapy (e.g., use of corticosteroid, hydrocortisone, or antihistamine creams; or wrapping the affected area with topical corticosteroids and wet bandages) or phototherapy (e.g., exposing the skin to controlled amounts of natural sunlight or artificial ultraviolet A (UVA) and narrow band ultraviolet B (UVB) either alone or with medications). Particularly, under this embodiment, there is provided a method for treating subjects suffering from AD who have previously undergone topical therapy.

Accordingly, embodiments of the disclosure relate to methods for treating, reducing the incidence of, preventing, or ameliorating at least one symptom or indication of AD in a subject who has previously undergone therapy for AD and who is deemed non-responsive to or have refracted or relapsed from the AD therapy, comprising administering a therapeutically effective amount of an anti-IL-13 antibody, or antigen-binding portion thereof, to the subject. The subject is, in some embodiments, a human subject who displays at least one symptom or indication associated with AD.

Determination of Treatment Efficacy

According to other aspects of the disclosure, methods for treating AD are tied to determination of effectiveness of treatment. Under this embodiment, the subject is administered a composition comprising a therapeutically effective amount of an anti-IL-13 antagonist and a change in the AD-associated marker is monitored before and/or after therapy. The therapy is deemed effective if at least one AD-associated marker (e.g., peripheral blood eosinophils, IgE, lactate dehydrogenase, IL-13, IL-22, TARC, and PARC, etc.) is reduced at a time after administration of the composition, as compared to the level of the marker in the subject prior to the administration. Under this embodiment, a reduction of at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67% 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91% 92%, 93%, 94%, 95%, 96%, 97%, 98%, 99% or more in the level of the marker after treatment with the composition containing the anti-IL-13 antibody, or antigen-binding portion thereof, compared to the level of the marker before treatment with the composition (or treatment with a placebo) signifies that the treatment is effective.

In another embodiment, a subject's global assessment of disease severity is determined.

In another embodiment, a clinician's global assessment of disease severity is determined. In yet another embodiment, a combination of subject's global assessment of disease severity and a clinician's global assessment of disease severity is determined.

In another embodiment, determining the subject's assessment of disease severity is determined in a subject both before administration of the antibody, or antigen-binding portion thereof (baseline), and after administration (post-treatment), is performed, wherein a reduction in the subject's assessment of disease severity compared to the baseline is indicative of the efficacy of treatment.

In another embodiment, determining the clinician's assessment of disease severity is determined in a subject both before administration of the antibody, or antigen-binding portion thereof (baseline), and after administration (post-treatment), is performed, wherein a reduction in the clinician's assessment of disease severity compared to the baseline is indicative of the efficacy of treatment.

In related embodiments, a composite (composite score) of a subject's score and a clinician's score before administration of the composition (baseline level) and after administration of the composition (post-treatment level) is determined, wherein a reduction in the composite score post-treatment compared to the baseline is indicative of the efficacy of treatment.

As will be appreciated by a person of ordinary skill in the art, an increase or decrease in an AD-associated biomarker can be determined by comparing (i) the level of the biomarker measured in a subject at a defined time point after administration of the composition comprising an anti-IL-13 antibody, or antigen-binding portion thereof, to (ii) the level of the biomarker measured in the patient prior to the administration of the composition comprising an anti-IL-13 antibody, or antigen-binding portion thereof (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, or more, after administration of the of the composition comprising an anti-IL-13 antibody, or antigen-binding portion thereof.

According to certain embodiments of the present disclosure, a subject may exhibit an increase or decrease in the level of one or more of peripheral blood eosinophils, IgE, lactate dehydrogenase, IL-13, IL-22, TARC, and/or PARC following administration of a composition comprising an anti-IL-13 antibody, or antigen-binding portion thereof. For example, at about day 1, day 4, day 8, day 15, day 22, day 25, day 29, day 36, day 43, day 50, day 57, day 64, day 71 or day 85, following administration of a first, second, third or fourth dose of a composition comprising an anti-IL-13 antibody, or antigen-binding portion thereof, the subject, according to the present disclosure, may exhibit an increase or decrease in peripheral blood eosinophils, IgE, lactate dehydrogenase, IL-13, IL-22, TARC, and/or PARC of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67% 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91% 92%, 93%, 94%, 95%, 96%, 97%, 98%, 99% or more from baseline (wherein "baseline" is defined as the level of peripheral blood eosinophils, IgE, lactate dehydrogenase, IL-13, IL-22, TARC, and/or PARC in the subject just prior to the first administration).

The present disclosure also includes methods for determining whether a subject is suitable for the therapy with a composition comprising an anti-IL-13 antibody, or antigen-binding portion thereof. For example, if an individual, prior to receiving a composition comprising an anti-IL-13 antibody, or antigen-binding portion thereof, exhibits a level of an AD-associated biomarker which signifies the disease state, the individual is therefore identified as a suitable patient for whom administration of a composition of the disclosure (a composition comprising an anti-IL-13 antibody, or antigen-binding portion thereof) would be beneficial. In related embodiments, the present disclosure includes methods for treating suitable subjects, wherein a suitable subject may be more susceptible to AD.

In other embodiments, the diagnostic methods may be aided by the power of gene expression assays.

In some embodiments, a subject who has been treated with an anti-IL-13 antibody, or antigen-binding portion thereof, is assessed at various time points using a plurality of specific and global markers. The specific marker may be a biomarker or a physiological marker described previously.

Additionally, related embodiments of the disclosure provide methods for monitoring of subjects undergoing therapy for AD comprising determining a parameter before and after therapy. In other embodiments, the parameter is selected from a subject's global assessment of disease severity; a clinician's global assessment of disease severity; a subject's global impression (e.g., based on wellness scoring); histology grades and stage-adjusted scores of the disease; number and severity of treatment-emergent adverse events (TEAE) (collectively termed "macroscopic assessments").

In the aforementioned embodiments relating to monitoring of therapy of AD based on macroscopic assessments, a post-treatment reduction of at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67% 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91% 92%, 93%, 94%, 95%, 96%, 97%, 98%, 99% or more in the subject's/clinician's assessment of disease severity, histology/stage scores, or TEAE numbers compared to pre-treatment levels is indicative of effective therapy. Likewise, a post-treatment increase of at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67% 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90% or more, or at least 1-fold, at least 1.2-fold, at least 1.5-fold, at least 1.8-fold, at least 2.0-fold, at least 2.5-fold, at least 3.0-fold or more in the betterment and/or wellness scores compared those obtained prior to treatment is indicative of effective therapy.

Applicants specifically incorporate the entire contents of all cited references in this disclosure. Further, when an amount, concentration, or other value or parameter is given as either a range or a list of upper values and lower values, this is to be understood as specifically disclosing all ranges formed from any pair of any upper range limit or value and any lower range limit or value, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

EXAMPLES

This is a global, multicenter, randomized, double-blind, placebo-controlled, parallel-group, dose-ranging, Phase 2 study to evaluate the efficacy and safety of cendakimab in adult subjects with moderate to severe AD. Subjects participating in the study must also be candidates for systemic therapy, defined as having an intolerance or inadequate response to treatment with topical medications for at least 4 weeks, or who have required systemic therapies to control their disease previously.

After completion of an up to 4-week screening period, approximately 200 eligible subjects (50 subjects per arm) will be randomized (1:1:1:1) to receive either cendakimab (720 mg QW, 720 mg Q2W, or 360 mg Q2W) or placebo. Treatment assignment will be stratified by geographic region (Japan versus rest of world); within rest of world region only, randomization will also be stratified by disease severity based on the baseline vIGA-AD score (3 [moderate] or 4 [severe]). Randomization will occur on Day 1 (Baseline) through the use of Interactive Response Technology (IRT) system.

The overall benefit/risk profile of the cendakimab 720 mg SC QW dose will be initially explored in this study. As this will be the first clinical study to further evaluate the safety and efficacy profile of cendakimab at higher cumulative exposures, additional safety assessments, such as increased onsite visit frequency, ongoing blinded safety reviews of the study data, oversight from an internal Safety Management Team (SMT), and oversight from an external independent Data Monitoring Committee (DMC), further described in Example 2.6) will be conducted during the study to ensure that the safety of the subjects is adequately monitored.

Clinical laboratory tests, vital signs, physical examinations (including height and weight), pregnancy tests, clinical symptom assessments, subject-reported outcomes, serum cendakimab concentrations, serum antibodies to cendakimab (to assess immunogenicity), concomitant medications, and AE assessments will be performed. Relevant biomarkers including but not limited to peripheral blood eosinophils, IgE, lactate dehydrogenase, IL-13, IL-22, CCL17 (TARC), and CCL18 (PARC) will be measured pre- and post-treatment.

Although concurrent treatment with background therapy to alleviate AD symptoms is prohibited during the Treatment and Follow Up periods of the study, the use of rescue medication, described in Example 4.4, may be employed for subjects who experience intolerable AD symptoms after randomization.

The maximum duration of subject participation in this study is approximately 36 weeks.

Subjects will participate up to 4 weeks in the Screening Period. Subjects will participate in a Screening Period that lasts up to 4 weeks. Over the treatment period, subjects will receive a total of 16 doses IP, administered once weekly, starting at Day 1/Week 0 and ending at Week 15. At Week 16, subjects will return for the End of Treatment Visit for safety and efficacy assessments. Following the Week 16 End of Treatment Visit, subjects will enter a 16 Week Follow Up Period, and will return for two additional visits to assess safety, clinical status, PK/PD, and serum antibodies to cendakimab. The Initial Follow Up Visit will be conducted 8 weeks after the End of Treatment Visit (Week 24) and the Final Follow Up/End of Study Visit will be conducted 16 weeks after the End of Treatment Visit (Week 32).

The blind should be maintained for persons responsible for the ongoing conduct of the study until after the primary analysis database lock, that is projected to be initiated after all subjects have completed Week 16/End of Treatment Visit assessments. Blinded persons may include but are not limited to: Clinical Research Physician, Clinical Research Scientist, Clinical Trial Manager, Study Statistician, Data Manager, Programmers, Clinical Research Associates.

The study will be conducted in compliance with the International Council on Harmonisation (ICH) of Technical Requirements for Registration of Pharmaceuticals for Human Use/Good Clinical Practice (GCP) and applicable regulatory requirements.

1.1—Study Duration for Subjects

The maximum duration of subject participation in this study is approximately 36 weeks.

Subjects will participate up to 4 weeks in the Screening Period. Upon randomization, subjects will enter the Treatment Phase of the study, and will receive a total of 16 doses of IP starting at Day 1 (Baseline) and ending at Week 15. At Week 16, subjects will return for the End of Treatment Visit for safety and efficacy assessments. Following the Week 16 End of Treatment Visit, subjects will enter a 16 Week Follow Up Period, and will return for two additional visits to assess safety, clinical status, PK/PD, and serum antibodies to cendakimab. The Initial Follow Up Visit will be conducted 8 weeks after the End of Treatment Visit (Week 24) and the Final Follow Up/End of Study Visit will be conducted 16 weeks after the End of Treatment Visit (Week 32).

End of Trial

The End of Trial is defined as either the date of the last visit of the last subject to complete the post-treatment follow-up, or the date of receipt of the last data point from the last subject that is required for primary, secondary and/or exploratory analysis, as prespecified in the protocol, whichever is the later date.

1.2—Study Population 1.2.1—Number of Subjects

Approximately 200 adult subjects (aged 18 to 75 years) with moderate to severe AD will be randomized worldwide.

1.2.2—Inclusion Criteria

Subjects must satisfy the following criteria to be enrolled in the study:

Subject must be ≥18 years and ≤75 years of age and have a body weight of ≥40 kg (88.2 lb) at the time of signing the informed consent form (ICF). Subjects in Japan must also be of legal age of consent (≥20 years of age) at the time of signing the ICF.

Subject has chronic AD as defined by Hanifin and Rajka (see, e.g., Tada, Japan Med. Assoc. J. 45:460-65 (2002)) that has been present for ≥1 year prior to the baseline visit (Day 1).

Subject has moderate to severe, active, and symptomatic AD defined by meeting all of the following criteria on the day of the baseline visit (Day 1):

BSA≥10%, and
EASI score≥16, and
vIGA-AD≥3, and
Pruritus NRS severity score≥4

Subject must have a documented history of inadequate response to treatment with topical medications for at least 4 weeks, unless topical treatments are otherwise medically inadvisable (e.g., because of important side effects, safety risks, and/or previous intolerance), or has required systemic therapy for control of disease Inadequate response is defined as either or both of:

failure to achieve and/or maintain a disease activity state comparable to IGA 0[clear] to 2[mild], despite treatment with a daily regimen of TCS of medium to higher potency (±TCI as appropriate), applied for at least 4 weeks (28 days) or for the maximum duration recommended by the product prescribing information, whichever was shorter, OR necessity of systemic therapy to control disease.

Subject must be willing to apply a stable dose of topical emollient (over-the-counter moisturizer) twice daily for ≥7 days prior to the Baseline visit and continue application throughout the study. Refer to Example 4.3 for additional requirements related to application of topical emollient throughout the study.

Subject must commit to avoid prolonged exposure to the sun and not to use tanning booths, sun lamps or other ultraviolet light sources during the study.

Subjects currently receiving concomitant medications for any reason other than AD, such as inhaled corticosteroids, leukotriene receptor antagonists (e.g., montelukast), or mast cell stabilizers (e.g., cromolyn sodium) for asthma, must be on a stable regimen, which is defined as not starting a new drug, changing, or stopping dosage within 7 days or 5 half-lives (whichever is longer) prior to Day 1 and through the treatment duration of the study.

Female subjects of childbearing potential must agree to practice a highly effective method of contraception. Highly effective methods of contraception are those that alone or in combination result in a failure rate of a Pearl index of less than 1% per year when used consistently and correctly. A female of childbearing potential (FCBP) is a female who: 1) has achieved menarche at some point, 2) has not undergone a hysterectomy or bilateral oophorectomy, or 3) has not been naturally postmenopausal (amenorrhea following cancer therapy does not rule out childbearing potential) for at least 24 consecutive months (i.e., has had menses at any time in the preceding 24 consecutive months) and must:

Have two negative pregnancy tests as verified by the Investigator prior to starting study therapy. She must agree to ongoing pregnancy testing during the course of the study and through the Final Follow-up Visit. This applies even if the subject practices true abstinence* from heterosexual contact.

Either commit to true abstinence* from heterosexual contact (which must be reviewed on a monthly basis and source documented) or agree to use, and be able to comply with, highly effective contraception without interruption throughout the study and for 5 months after the last dose of IP.

Acceptable methods of birth control in this study are the following:

a. combined hormonal (estrogen and progestogen containing) contraception, which may be oral, intravaginal, or transdermal. Note: Intravaginal and transdermal combined hormonal contraception are not approved by Japan Health Authority and would therefore not be acceptable methods contraception for subjects enrolled in this region.

b. progestogen-only hormonal contraception associated with inhibition of ovulation, which may be oral, injectable, or implantable. Note: progestogen-only hormonal contraception is not approved by Japan Health Authority and would therefore not be acceptable methods contraception for subjects enrolled in this region.

c. placement of an intrauterine device (IUD)

d. placement of an intrauterine hormone-releasing system (IUS)

e. bilateral tubal occlusion f. vasectomized partner g. sexual abstinence

Subject is willing to receive weekly SC injections throughout the study. Subject must understand and voluntarily sign an ICF prior to any study-related assessments/procedures being conducted. Subject is willing and able to adhere to the study visit schedule and other protocol requirements.

*True abstinence is acceptable when this is the preferred and usual lifestyle of the subject. Periodic abstinence (eg, calendar, ovulation, symptothermal, post-ovulation methods), withdrawal (coitus interruptus), and lactational amenorrhea method are not acceptable methods of contraception 1.2.3—Exclusion Criteria The presence of any of the following will exclude a subject from enrollment:

Evidence of an active and/or concurrent inflammatory skin condition (e.g., seborrheic dermatitis, psoriasis, acute allergic contact dermatitis, etc.) that would interfere with the investigator or subject driven evaluations of AD Evidence of acute AD flare between the Screening and Baseline/Randomization (eg, doubling of the EASI score between Screening and Baseline)

Use of topical treatments that could affect the assessment of AD (e.g., corticosteroids, calcineurin inhibitors, tars, antibiotic creams, topical antihistamines) within 7 days of the Day 1 visit.

Received phototherapy narrowband UVB (NB-UVB) or broad band phototherapy within 4 weeks prior to the Baseline visit.

Evidence of immunosuppression, subject is receiving, or has received systemic immunosuppressive or immunomodulating drugs (e.g. azathioprine, cyclosporine, systemic corticosteroids, IFN-γ, Janus kinase inhibitors, methotrexate, mycophenolate-mofetil, etc.) within 4 weeks prior to the Baseline visit.

Treatment with immunomodulatory biologics as follows:

a. Dupilumab within 3 months of Baseline visit.

b. Cell-depleting biologics, including to rituximab, within 6 months prior to the Baseline visit.

c. Other immunomodulatory biologics within 5 half-lives (if known) or 16 weeks prior to Baseline visit, whichever is longer.

d. Concurrent treatment with another IP, including through participation in an interventional trial for COVID-19. Prospective subjects may not participate in a concurrent IP study or have received an IP within 5 drug half-lives prior to signing the ICF for this study. Further, for subjects who received an investigational COVID-19 vaccine as part of a clinical trial prior to the first Screening Visit, enrollment must be delayed until the biologic impact of the vaccine is stabilized, as determined by discussion between the Investigator and the Clinical Trial Physician.

e. Received a live attenuated vaccine within one month prior to the first Screening Visit or anticipates the need to be vaccinated with a live attenuated vaccine during the study. Administration of any live attenuated vaccine will be prohibited during the study through the Final Follow-up Visit.

f. Previously received cendakimab treatment (formerly known as RPC4046 and ABT-308).

g. Liver function impairment or persisting elevations of aspartate aminotransferase/serum glutamic oxaloacetic transaminase (AST/SGOT) or alanine aminotransferase/serum glutamic pyruvic transaminase (ALT/SGPT) that are 2 or more times the upper limit of normal (ULN), or total bilirubin 1.5 times the ULN. Subjects with elevations that are not clinically significant in total bilirubin associated with Gilbert's syndrome may participate.

h. Active chronic or acute skin infection that requires treatment with systemic antibiotics, antivirals, antiparasitics, antiprotozoals, or antifungals within 2 weeks prior to Day 1, or superficial skin infections within 1 week prior to Day 1.

i. Active parasitic/helminthic infection or a suspected parasitic/helminthic infection. Subjects with suspected infections may participate if clinical and/or laboratory assessments rule out active infection prior to randomization.

j. Ongoing infection (including but not limited to, hepatitis B or C, human immunodeficiency virus [HIV], or tuberculosis as defined by standard medical guidelines and as outlined in Example 3.1 for which testing to rule out is required during screening).

k. A previous severe acute respiratory syndrome coronavirus 2 (SARS-CoV-2) infection within 4 weeks prior to screening. Symptoms must have completely resolved and based on Investigator assessment in consultation with the Clinical Trial Physician, there are no sequelae that would place the participant at a higher risk of receiving investigational treatment. Refer to Example 3.1.3 for additional guidance related to SARS-CoV-2 testing during screening.

l. Is pregnant or lactating.

m. A history of idiopathic anaphylaxis or a major immunologic reaction (such as anaphylactic reaction, anaphylactoid reaction, or serum sickness) to an immunoglobulin G (IgG) containing agent. A known hypersensitivity to any ingredient in the investigational product (IP) is also exclusionary.

n. History of cancer or lymphoproliferative disease, other than a successfully treated non-metastatic cutaneous squamous cell or basal cell carcinoma or adequately treated cervical carcinoma in situ, within 5 years of screening.

o. History of alcohol or drug abuse within 5 years prior to initiation of screening.

p. Any significant medical condition, laboratory abnormality, or psychiatric illness that would prevent the subject from participating in the study.

q. Any condition including the presence of laboratory abnormalities, which places the subject at unacceptable risk if he/she were to participate in the study.

r. Any other condition that confounds the ability to interpret data from the study.

Example 2—Procedures

Study assessments and procedures are described herein. The day of administration of the first dose of IP is defined as Day 1 (Baseline/pre-dose).

It is recommended that the study visits are scheduled in the morning. Whenever possible, the assessment order sequence, should remain constant and should be conducted at approximately the same time of day throughout the study.

2.1—Screening Period

Screening evaluations will be performed for all subjects to determine study eligibility. These evaluations must be completed within 28 days (4 weeks) prior to receiving the first dose of IP unless noted otherwise below. Waivers to the protocol will not be granted during the conduct of this study, under any circumstances.

Screening procedures will be performed for all subjects to determine study eligibility. All screening procedures must be completed within 4 weeks prior to receiving the first dose of IP.

The electronic patient-reported outcome (ePRO) instrument on a handheld device will be distributed to subjects at the Screening Visit. After completion of a training module, the Pruritus NRS will be completed by the subject daily for at least the last week (7 days) during the Screening Period (prior to Day 1); however, value to assess inclusion criteria will be assessed on Day 1 (Baseline/pre-dose).

Safety laboratory analyses and all assessments will be performed. Screening laboratory values must demonstrate subject eligibility; however, analytes may be repeated (and analyzed by the central laboratory) within the screening window, if necessary.

Written, signed, and dated informed consent from the subject prior to the performance of any study related procedures must be obtained by the Principal Investigator or designee. A copy of the signed informed consent must be given to the subject for his/her records.

The following evaluations will be performed at screening after informed consent/assent has been obtained:

Assessment of inclusion/exclusion criteria

Demographics and baseline characteristics

Medical history including atopy status (documentation of AD history, other atopic conditions, and past pharmacotherapy for AD, and other atopic conditions) and as well as details of any prior therapy or procedures to treat AD or other atopic conditions. Prior therapy and concomitant therapy (including all procedures occurring ≤28 days before screening).

Adverse event assessment begins when the subject signs the informed consent/assent form. Throughout the course of the study, every effort must be made to remain alert to possible AEs or serious AEs (SAEs). Once subjects consent, AEs/SAEs will be recorded at each study visit. Refer to Example 6 for definitions of AEs/SAEs, monitoring, and reporting Hematology, chemistry, coagulation panel, and urinalysis (central laboratory). The following safety laboratory tests will be performed to assess the safety profile of cendakimab:

Hematology: red blood cell (RBC) count, total and differential white blood cell (WBC) count (basophils, eosinophils, lymphocytes, monocytes, and neutrophils), platelet count, hemoglobin (hgb), hematocrit (hct), mean corpuscular volume (MCV), mean corpuscular hemoglobin (MCH) and mean corpuscular hemoglobin concentration (MCHC)

Blood chemistry: indices included at all required chemistry timepoints are sodium, potassium, chloride, calcium, magnesium, phosphate, blood urea nitrogen, glucose (random, at timepoints not requiring fasting), albumin, alkaline phosphatase, creatinine, creatine phosphokinase (CPK), ALT/SGPT, AST/SGOT, gamma glutamyltransferase (GGT), amylase, total bilirubin, direct bilirubin and C reactive protein (CRP); in addition, fasting lipid panel (total cholesterol, triglycerides, high-density lipoprotein, and low-density lipoprotein) and fasting glucose (instead of random glucose) will be performed only at Day 1 and Week 6/EOT/ET.

Coagulation: Prothrombin time (PT), activated partial thromboplastin time (aPTT), and international normalized ratio (INR)

Urinalysis: leukocytes, specific gravity, bilirubin, blood, glucose, ketones, pH, protein, and urobilinogen Testing for hepatitis B virus (HBV), hepatitis C virus (HCV), and HIV (central laboratory) will be performed at screening only.

HBV: Hepatitis B surface antigen (HBsAg) screening test and hepatitis B core antibody (HBcAb) test will be performed. Subjects who test positive for HBsAg will be excluded from the study. For subjects who test positive only for HBcAb, an HBV deoxyribonucleic acid (DNA) test must be performed. If the HBV DNA test is positive, the subject will be excluded from the study. If the HBV DNA test is negative (without antiviral therapy) and ALT and AST are ULN, the subject will be eligible for this study.

HCV: HCV antibody (anti-HCV IgG) test will be performed. Subjects testing positive for HCV antibody and have a positive confirmatory test (HCV ribonucleic acid [RNA]) will be excluded from the study. Subjects with evidence of cleared HCV infection (e.g., HCV antibody positive subjects who are negative for HCV RNA) and who have not received anti-HCV therapy for at least 12 weeks will be eligible for participation.

HIV: An HIV antibody test will be performed. Subjects testing positive for HIV (enzyme-linked immunosorbent assay [ELISA] test result, confirmed by western blot) will be excluded from the study.

Testing for tuberculosis (TB) will be performed at screening only. Active TB must be ruled out according to local medical practices. TB must be assessed with a TB skin test, QuantiFERON Gold test, or other interferon gamma release assay (IGRA) (e.g., T-SPOT). Subjects with latent TB must have documentation of completed prophylactic treatment by local standard of care. Subjects with an indeterminate test result using any IGRA test, must be discussed for eligibility on a case by case basis by the Sponsor's Medical Monitor or designee. Subjects with latent TB who were only partially treated or who are currently receiving prophylactic treatment will not be eligible for randomization.

Serum pregnancy test (only for FCBP). A test for the β-subunit of serum human chorionic gonadotropin (β-hCG) must be performed at screening in females of childbearing potential. Urine (or serum) β-hCG will be performed at Day 1 and at later timepoints. In the event of a positive urine test, the subject is not to be dosed, and confirmation with a serum pregnancy test should be performed. At screening and at each subsequent study visit, the Investigator will counsel FCBP subjects on pregnancy precautions for the duration of the study.

Physical examination: A complete physical examination (including evaluation of heart, lung, head and neck, abdomen, neurological assessment, and extremities) will be performed.

Height and weight

Vital signs: Heart rate, blood pressure (systolic and diastolic), respiratory rate, and temperature will be assessed at each visit. Blood pressure and pulse will be assessed in a sitting position and once the subject is at rest. An automated validated device may be used, if available.

Electrocardiogram (ECG): Single 12-lead ECG will be conducted only at the Screening Visit when the subject is at rest and may be repeated to confirm any abnormal findings.

AD disease activity assessments:
vIGA-AD
EASI
BSA
Pruritus NRS 2.1.1—Additional Information Regarding Safety Laboratory Assessments Analysis of samples will be conducted by a central laboratory. Details regarding collection of samples, shipment of samples, reporting of results, laboratory reference ranges, and alerting abnormal values will be supplied to the site before site initiation in a Study Laboratory Manual. The results of the analysis will be made available to each site by the central laboratory.

Additional and repeat laboratory safety testing may be performed locally at the discretion of the Investigator. As local laboratory data will not be collected in the electronic case report form (eCRF), if feasible, a sample should also be sent to the central laboratory. In addition, when safety laboratory samples are being collected to further assess AEs, it is recommended that serum samples to assess ADA and PK also be collected and sent to the central laboratory, when feasible. Laboratory samples required to confirm study eligibility (e.g., liver function test, serology panel, etc.) are required to be performed by the central laboratory if a retest is required during Screening. Retesting of specific laboratory parameters to confirm eligibility is allowed once during screening. If upon retest the subject still does not meet eligibility criteria, the subject should be screen failed.

2.1.2—Screening Failures and Rescreening of Potential Subjects

A screen failure is defined as a subject who has given informed consent/assent and failed to meet the inclusion and/or exclusion criteria. Subjects who initially fail to meet the inclusion/exclusion criteria may be re-screened as per the assessment of the Investigator. Subjects who are re-screened will be required to be re-consented and have all required Screening Visit procedures performed. Subjects may be re-screened only one additional time for the study without prior consultation with the Medical Monitor.

2.1.3—Rescreening of Subjects Who Develop COVID-19 During the Screening Period

Molecular testing for asymptomatic COVID-19 infection is not required in this study. However, where local requirements or institutional practice are more restrictive, asymptomatic COVID-19 screening may be performed locally, to ensure compliance with current local guidance. In addition, some subjects may develop suspected or confirmed symptomatic COVID-19 infection, or it is discovered that subjects have asymptomatic COVID-19 infection during the Screening Period. In such cases, subjects may be considered eligible for the study after meeting all Inclusion/Exclusion Criteria related to active infection, and after meeting the following criteria:

At least 10 days (20 days for severe/critical illness) have passed since symptoms first appeared or positive test result, and At least 24 hours have passed since last fever without the use of fever-reducing medications, and Symptoms (e.g., cough and shortness of breath) have resolved and In the opinion of the Investigator, there are no COVID-19 sequelae that may place the subject at a higher risk of receiving investigational treatment, and Negative follow-up molecular test for COVID-19 based on institutional, local or regional guidelines

2.2—Treatment Period

On Day 1, prior to randomization in the, the baseline assessments (including laboratory assessments, and the optional skin biopsy) will be completed prior to the administration of investigational product. The Investigator will review all available information to confirm subject eligibility.

- Screening laboratory tests will be used to determine eligibility for randomization with the exception of pregnancy tests, which will need to be confirmed by the Day 1 test results.
- A urine (or serum) pregnancy test must be performed for all females of childbearing potential on Day 1 and the results reviewed prior to randomization. A negative pregnancy test result must be obtained prior to randomization. If the urine pregnancy test result is positive but this is believed to be a false positive, the site must perform a serum pregnancy test at the local laboratory to confirm pregnancy status.
- Baseline laboratory tests will be performed on Day 1 for comparison with follow-up tests. However, the results of these tests will not be available prior to randomization on Day 1.
- The baseline vIGA-AD, EASI, BSA, and the subject reported Pruritus NRS performed on 1 Day will be used to assess subject eligibility; the stratification data point for vIGA-AD score will be provided for randomization.

After eligibility has been confirmed and baseline assessments have been completed, eligible subjects will be randomized to treatment on Day 1. Subsequent visits, assessments and procedures will be performed.

- Assessment of inclusion/exclusion criteria to confirm eligibility (Day 1 only)
- Concomitant therapy
- Assessment of AEs/SAEs. In addition, starting at Day 1, device (i.e., pre-filled syringe) failures or malfunctions should be captured, and device related AEs should also be collected.
- Hematology, chemistry, fasting lipid panel, and urinalysis
- Urine pregnancy test (only for FCBP)
- Physical examination (A complete physical examination (including evaluation of heart, lung, head and neck, abdomen, neurological assessment, and extremities) or an abbreviated (interim/brief) physical examination (including areas with previously noted abnormalities and/or that are associated with any new complaints from the subject) will be performed.
- Weight
- Vital signs
- Serum antibodies to cendakimab
- Serum cendakimab PK assessment
- Whole blood and serum biomarkers assessment
- SARS-CoV-2 serology assessment
- Pharmacogenetic assessment, if applicable per government and local regulations, will be collected one time at Day 1 (note, the sample may be obtained at any subsequent visit).
- Optional Skin Biopsy
- AD disease activity and efficacy assessments:
  - vIGA-AD
  - EASI
  - BSA
  - SCORAD
  - Pruritus NRS
  - PROMIS Sleep Disturbance SF
  - DLQI
  - HADS
  - IP administration Refer to Example 2.5 for a detailed description of the efficacy assessments and outcome measures conducted throughout the study.

2.2.1—End of Treatment or Early Termination

For subjects who complete treatment phase of the study (Week 16) or discontinue the study prematurely for any reason (i.e., subjects that do not complete Week 16) an EOT/ET visit will be conducted. For subjects who discontinue the study prematurely, every attempt should be made to complete the assessments detailed in the ET Visit conducted as close as possible to the time of study discontinuation. If study discontinuation occurs at the regularly scheduled visit, the ET Visit and all corresponding ET Visit procedures should be conducted. In addition, these subjects should return for the Follow-up Visits.

2.3—Follow-Up Period

All subjects will be followed for 16 weeks after the EOT/ET visit for AE reporting, as well as SAEs made known to the Investigator at any time thereafter that are suspected of being related to IP, as described in Example 6.1. Subjects will return for an Initial (Week 24) and a Final (Week 32) Follow-up Visit at 8 and 16 weeks, respectively after completion of the EOT/ET Visit. For subjects who prematurely discontinue from the study, the 16 Week Follow Up Period should be based off of the date of last study visit conducted during the Treatment Phase of the study (e.g., the ET visit) and therefore, may be conducted earlier then Week 24 and Week 32.

2.4—Efficacy Assessments

The following efficacy assessments are completed by the investigator include the validated Investigator Global Assessment for Atopic Dermatitis, Eczema Area and Severity Index, Body Surface Area (BSA) %, and the SCORing Atopic Dermatitis Index. Clinical efficacy evaluations of atopic dermatitis will be performed by an experienced and qualified medical professional, with experience in the conduct of AD clinical trials.

All efficacy evaluators must receive and document protocol specific and applicable efficacy assessment scales training prior to performing the evaluations. To assure consistency and reduce variability, the same evaluator must assess all dermatological clinical evaluations for any individual subject throughout the study whenever possible; a back-up experienced, and qualified, protocol-trained evaluator will only be allowed on rare occurrences, when the designated evaluator is unable to perform the evaluation. Every effort should be made to ensure that the same assessor conducts the assessments at all study visits for a given subject.

2.4.1—Validated Investigator Global Assessment

The vIGA-AD is a validated 5-point assessment intended to assess the global severities of key acute clinical signs of AD, including erythema, induration/papulation, oozing/crusting (lichenification excluded). The rating of cleared (0), almost cleared (1), mild (2), moderate (3) and severe (4), will be assessed at scheduled visit specified in Example 1. The vIGA-AD must be conducted before the EASI assessment. The IGA is a static evaluation conducted without regard to the score obtained at a previous visit.

2.4.2—Eczema Area Severity Index

The EASI is a composite scoring system assessed by the investigator based on the proportion of each of the four body regions (head and neck, upper limbs, lower limbs, and trunk) affected with AD and the intensity of each of four main signs of AD (e.g., erythema, induration/papulation, excoriation, and lichenification) and is based on a 4-point scale of 0 (none), 1 (mild), 2 (moderate), and 3 (severe). Assessment of the four main clinical signs is performed separately for four body regions: head and neck, upper limbs, trunk (including axillae and groin) and lower limbs (including buttocks). The total EASI score ranges from 0 to 72, with higher scores indicative of more severe disease.

2.4.3—Body Surface Area

Body Surface Area involvement will be calculated from the sum of the number of handprints of skin afflicted with atopic dermatitis in a body region. The number of handprints of skin afflicted with atopic dermatitis in a body region can be used to determine the extent (%) to which a body region is involved with AD. When measuring, the handprint unit refers to the size of each individual subject's hand with fingers in a closed position. BSA will be calculated by the investigator or qualified designee using the 1% handprint rule, in which the area represented by the palm with all five digits adducted together is approximately 1% of the subject's BSA.

2.4.4—SCORing Atopic Dermatitis Index

The SCORAD is a validated scoring index for atopic dermatitis, which combines extent (0 to 100), severity (0 to 18), and subjective symptoms (0 to 20) based on pruritus and sleep loss, each scored (0 to 10). The subject will assess the subjective symptoms (itch and sleepless) part of the assessment.

2.5—Subject Reported Efficacy Assessments and Outcome Measures

Subject reported efficacy assessments and outcome measure relevant to AD include the following assessments:

Pruritus Numeric Rating Scale
PROMIS Sleep Disturbance Short Form 8a
Patient Oriented Eczema Measure
Dermatology Quality of Life Index
Hospital Anxiety and Depression Scale 2.5.1—Pruritus Numeric Rating Scale Pruritus will be assessed by the subject using the Pruritus NRS, which was developed and validated as a single item, patient reported outcome (PRO) of itch severity. Clinical response is indicated by a ≥2-4-point change from baseline in Peak Pruritus NRS score. The intensity of pruritus will be assessed based on last 24 hours using a validated 11-point NRS, ranging from 0 ("no pruritus") to 10 ("the worst pruritus imaginable"). The subject will complete an electronic diary recording the intensity of their pruritus on daily basis, through Week 4, and weekly (e.g., on study visit/study drug administration days) thereafter through the Week 16 visit.

2.5.2—PROMIS Sleep Disturbance Short Form

The PROMIS Sleep Disturbance Short Form 8a is an 8-question subject questionnaire, designed to capture the subject's perceptions of sleep quality, sleep depth, and restoration associated with sleep over the past week. The questionnaire is scored by: [sum of items×8]÷number items answered]. The higher the total score, the more severe the symptom. Total scores less than 24 suggest no to slight sleep disturbance, 24-28 suggest mild disturbance, 29-38 moderate disturbance, and greater than 38 severe sleep disturbance.

The subject will complete the questionnaire onsite at study visits.

2.5.3—Patient Oriented Eczema Measure

The POEM is a validated tool used for monitoring atopic eczema severity. It is a 7-item questionnaire completed by the subject to assess the severity of eczema over the last week. The 7 questions each carry equal weight, and the responses are scored from 0 to 4 for a total score range of scored 0-28: To date, two published studies have broadly concurred that the minimally important change (MIC) of the POEM is 3 points (Howells, 2018).

The subject will complete the questionnaire onsite at study visits.

2.5.4—Dermatology Quality of Life Index

The DLQI will be completed by the subject at study visits. It is self-administered, easy-to-use, dermatology-specific quality of life (QOL) questionnaire that consists of 10 questions related to a subjects' perception of the impact of skin diseases on different aspects of their QOL over the last week. Questions are scored from 0 to 3, giving a possible total score range from 0 (meaning no impact of skin disease on quality of life) to 30 (meaning maximum impact on quality of life).

2.5.5—Hospital Anxiety and Depression Scale (HADS)

The HADS is questionnaire completed by the subject that assesses anxiety and depression in a non-psychiatric population. The HADS has two subscales (depression and anxiety), both with 7 questions. Responses are based on the relative frequency of symptoms over the past week, using a four-point scale ranging from 0 (not at all) to 3 (very often indeed). HADS is completed by the subject at study visits.

2.6—Safety Assessments

The safety parameters outlined in Example 1 that will be assessed in this study are the similar to those used in previously or currently conducted clinical studies of cendakimab. Careful safety monitoring of clinical and laboratory findings by both the sponsor's medical monitors and by the investigators has been implemented in this protocol. As this will be the first clinical study to further explore the safety and efficacy profile of cendakimab at higher cumulative exposures, additional risk minimization measures, such as the frequency of onsite visits, ongoing blinded safety reviews of the study data, oversight from an internal Safety Management Team (SMT), and oversight from an external independent Data Monitoring Committee (DMC), will be implemented throughout this Phase 2 study to ensure that the safety of the subjects is adequately monitored. An overview of the additional safety oversight measures for the study are summarized below.

2.6.1—Onsite Visit Frequency

All subjects will return to the site weekly for the first 3 weeks for routine safety monitoring, IP administration, and a 30-minute post IP administration observation period. Subjects will either return to the clinic weekly throughout the 16-week treatment period, or starting at Week 3, subjects may have the option to return to the clinic every other week for IP administration, and have their alternate week injections administered at home by a visiting home health nurse.

Subjects who utilize the home health nurse option will be required to return to the site every 2 weeks at a minimum (e.g., Week 4[Visit 5/Day 29], Week 6 [Visit 7/Day 43], Week 8 [Visit 9/Day 57, Week 10 [Visit 11/Day 71], Week 12 [Visit 13/Day85, Week 14 [Visit 15/Day 99], and Week 16[Visit 17/Day 113]) to ensure additional safety assessments, such as the collection safety laboratory samples, and onsite assessments by investigator and site personnel can be performed. Subject who utilize the home health services option for any visits will still be contacted by site personnel (within 24 hours) to assess for any changes in concomitant medication use, and assess for adverse events, to ensure there is continuity in the safety oversight being performed by the investigator and site personnel.

2.6.2—Blinded Safety Data Reviews

From the start of the study (defined as first subject randomized) blinded safety reviews will be conducted by the internal study team/blinded data review team members on an ongoing basis. In addition, safety data will also be assessed by the SMT on a regular basis, and specific members of the SMT may also participate in the ongoing study data review related activities. The expected frequency of these planned reviews is outlined below:

- A preliminary interim blinded safety review involving the internal study team and the SMT will also be conducted after the first 8 subjects have received at least 4 weeks of treatment with IP. A similar review will be initiated after the first 8 Japanese subjects have received at least 4 weeks of treatment. The purpose of these preliminary interim reviews will be to review data in a blinded, aggregate fashion to assess for any potential clinically significant safety findings early in the study conduct.
- From the start of the study (as defined as first subject randomized) ongoing blinded safety reviews will be conducted by the internal study team/data review team members on approximately a monthly basis. More frequent review may be conducted on an ad-hoc basis if needed.

2.6.3—Internal Safety Management Team

In addition to ongoing safety monitoring conducted by Investigators and study personnel, cumulative and interval blinded AEs, AESI, SAEs, discontinuations due to AEs, and abnormal laboratory findings will be reviewed internally by the Sponsor Safety Management Team (SMT). The SMT is comprised of lead representatives from multiple Sponsor functions engaged in the cendakimab development program. The scope, conduct, processes, and accountabilities are specified by Sponsor Standard Operating Procedure (SOP).

Subject or study level safety assessments, and any subsequent study conduct related recommendations and/or actions provided by the SMT will be made from blinded data only. The DMC will be informed of relevant subject or study level decisions made by the SMT.

2.6.4—Data Monitoring Committee Safety Oversight

A DMC, that is independent of the study team, and SMT, has been established to provide an additional level of safety oversight. The DMC will function in advisory capacity, making recommendations to study team and SMT based on their independent assessment of the safety data. Members of the internal study team/data review team or SMT may also consult with the DMC on an ad-hoc basis throughout the duration of the study to discuss relevant safety findings (e.g., AESI, SAE, findings related to subject discontinuation, etc.) that may arise during study the conduct of the study.

2.7—Anti-Drug Antibody Assessments

Serum samples to assess blood levels of antibodies to cendakimab will be obtained pre-dose, at the EOT/ET visit, and the Follow-up Visits at various timepoints.

Details of the procedures to be followed for sample collection, processing, storage, shipment, and testing will be documented in a separate Study Laboratory Manual.

The development of serum antibodies to cendakimab will be monitored to assess the impact of immunogenicity on safety, PK, and efficacy of cendakimab. The impact of immunogenicity will be evaluated by considering the results of PK, pharmacodynamic, and immunogenicity data taken together. Samples will be stored for additional analysis if necessary.

Further analysis on samples that are positive for ADA may be performed, including assessment of neutralizing antibodies when warranted. Samples will be stored for up to 5 years after study completion.

2.8—Pharmacokinetics

Serum samples to assess cendakimab concentrations will be obtained pre-dose at study visits, at the EOT/ET visit, and at the Follow-up Visits at various timepoints.

Details of the procedures to be followed for sample collection, processing, storage, shipment, and testing will be documented in a separate Study Laboratory Manual.

2.9—Biomarkers, Pharmacodynamics, Pharmacogenomics 2.9.1—Whole Blood and Serum Biomarker Assessments Blood samples will be obtained pre-dose at the EOT/ET visit, and the Follow-up Visits at various timepoints to evaluate levels of various biomarkers in whole blood and serum, including but not limited to peripheral blood eosinophils, IgE, lactate dehydrogenase, IL-13, IL-22, CCL17 (TARC), and CCL18 (PARC), and possible assessments of SARS-CoV-2 serologic status, at various timepoints. Serum will be collected for measurements of SARS-CoV-2 serology (anti-SARS-CoV-2 total or IgG) per national and local regulations. Of note, serum will be collected for SARS-CoV-2 serology at Day 1 (baseline), EOT/ET Visit, as well as approximately 4 weeks after a documented or suspected SARS-CoV-2 infection, if applicable.

A pharmacogenomics sample will be collected only at one timepoint and is scheduled at Day 1 (see Example 1) for biomarker assessment including but not limited to IL-13 single nucleotide polymorphism (SNP) characterization. The pharmacogenetic sample will be collected from subjects, provided that necessary governmental and local approvals have been obtained. If needed, the pharmacogenetic sample can be collected at any subsequent timepoint during the study.

These samples will be shipped to a central laboratory for analysis. Details of the procedures to be followed for sample collection, processing, storage, and shipment will be documented in a separate Study Laboratory Manual.

2.9.2—Tissue Biomarker Assessments

Skin punch biopsies will be optional but will be critical to a full understanding of response to these therapies in AD patients. Looking to future studies, having as many skin samples as possible will also allow for greater understanding of which tissue measures may have viable blood/serum surrogates and what can only be assessed accurately from biopsies. Skin punch biopsies from the site of the same AD lesion will be taken at baseline, at the EOT/ET, and at the Final Follow Up Visit. For comparison, a biopsy of adjacent nonlesional skin will be taken at baseline, in order to provide a reference point. Samples will either be frozen, placed in formalin, or sent into an equivalent process as appropriate for the experimental end use of the material (eg, separate processing for RNA extraction). Details for the biopsy procedures will be provided in the Study Laboratory Manual.

Example 3—Description of Study Treatments 3.1—Description of Investigational Product(s)

The active ingredient of cendakimab is a recombinant humanized IgG1 monoclonal antibody directed against human IL-13. Investigational products (cendakimab and placebo solutions for injection) are to be stored at 2° to 8° C. The IP should not be frozen. The labeling will be in accordance with GCP and any other local regulatory requirements. During the study, IP will be dispensed in pre-filled syringes (PFS) provided by the Sponsor.

Cendakimab solution for injection (or placebo) will be provided as a sterile liquid in PFS at a concentration of 180 mg/mL (or placebo), a 2.0 mL fill will be utilized in the study, and IP will be packaged in cartons (2 PFS per carton).

Additional instructions related to IP handling, preparation, dispensation, and administration will be provided in a separate Study Pharmacy Manual.

3.2—Treatment Administration Schedule

Two injections at a volume of 2 mL will be administered SC once weekly using a PFS of cendakimab 180 mg/ml (active IP) or matching placebo. In order to maintain the blind, all subjects, regardless of their treatment assignment, will receive 2 injections of either active IP, placebo, or a combination of both. Subjects will be randomized 1:1:1:1 to one of the following treatment arms:

Cendakimab 720 mg SC once weekly for 16 weeks, that will be administered via 2 injections of active IP each week.

Cendakimab 720 mg SC every other week for 16 weeks. Starting at the baseline visit, 2 injections of active IP will be administered. On the alternate weeks, 2 injections of placebo will be administered.

Cendakimab 360 mg SC every other week for 16 weeks. Starting at the baseline visit, 1 injection of active IP and 1 injection of matching placebo will be administered. On the alternate weeks, 2 injections of placebo will be administered weekly to maintain the blind.

Matching placebo SC once weekly for 16 weeks, that will be administered via 2 injections of placebo each week.

The first 3 doses of IP are required to be administered in the clinic. For the first 3 dosing visits, subjects will be required to remain in the clinic for at least 30 minutes for further observation. Per Investigator discretion, the number of injections administered in the clinic, and the post injection observation time period may be extended, as needed, to comply with local requirements.

Thereafter, dosing with two SC injections of IP will continue weekly through the Week 15 visit. Starting at Week 3 (Visit 4/Day 22), subjects have the option to return to the clinic every other week for IP administration, and have their alternate weekly injection administered at home by a licensed home health care provider. Subjects who utilize the home health care service will be required to return to the site every 2 weeks at a minimum (e.g., Week 4 [Visit 5/Day 29], Week 6 [Visit 7/Day 43], Week 8 [Visit 9/Day 57], Week 10 [Visit 11/Day 71], Week 12 [Visit 13/Day85], Week 14 [Visit 15/Day 99], and Week 16 [Visit 17/Day 113]) during the treatment phase of study for scheduled laboratory collections, and additional safety and efficacy assessments. In addition, on the weeks that the IP is not administered in-clinic, the subject will be contacted by site personnel (within 24 hours) to assess for any changes in concomitant medication use and assess for adverse events.

Subjects for whom home health care provider services are not available in their region, or who choose not to utilize the service, will be required return to the clinic weekly to receive all of their IP injections.

The two SC doses should be administered in to separate locations, in the abdomen or other appropriate alternate location including the thigh or back of the upper arm (rotating the injection site each time), avoiding any blood vessels, thickened or tender skin, scars, fibrous tissue, stretch marks, bruises, redness, nevi, or other skin imperfections.

3.2.1—Administration by a Visiting Home Health Care Provider

Starting at Week 3, subjects may have the option to return to the clinic every other week for IP administration, and have their alternate week injections administered at home by a visiting home health nurse. Subjects who utilize the home health nurse option will be required to return to the site every 2 weeks at a minimum (e.g., Week 4 [Visit 5/Day 29]. Week 6 [Visit 7/Day 43], Week 8 [Visit 9/Day 57], Week 10 [Visit 11/Day 71], Week 12 [Visit 13/Day 85], Week 14 [Visit 15/Day 99], and Week 16 [Visit 17/Day 113]) during the treatment phase of study for scheduled laboratory collections, and additional safety and efficacy assessments. The home health care providers will be trained and will be able to monitor for injection site reactions at the time of administration. Within 24 hours of the home health care provider visit, the subject will be contacted by the site personnel to assess for any changes in concomitant medications and/or adverse events. Subjects for whom home health nurse services are not available in their region, or who choose not to utilize the visit home health nurse service option, will be required return to the clinic weekly for their injections.

3.2.2—Missed Dose(s)

If subjects are unable to take a dose on the usually scheduled day:

They may take the dose within ±3 days of the normal dosing day and then continue dosing on their regular day the next week If the dose cannot be taken within ±3 days of the normal dosing day, they should wait to take their next dose on their regular dosing day the following week Any missed doses will be captured within the study records. If 3 or more consecutive doses are missed, the subject will be required to permanently discontinue IP.

3.2.3—Overdose

An overdose is any dose of IP given to a subject or taken by a subject that exceeds the dose described in the protocol. There is no information regarding overdose with cendakimab. Any overdose, with or without associated AEs, must be promptly reported to the Medical Monitor (see Example 6.1). Any doses of IP administered more frequently than the minimum of 3 calendar days in between dose administrations allowed by visit window, further described in Example 3.2.2, should be reported as an overdose.

3.2.4—Dose Adjustments

There is no provision for dose adjustments in this study. Subjects who cannot tolerate their assigned dose of IP, as determined by the Investigator, will be permanently discontinued from IP.

3.2.5—Guidelines for Temporary Interruption of Dosing

Dosing for subject should be interrupted (temporary discontinuation of IP) if any of the following events occur:

The subject experiences any AE, intercurrent medical condition, or major surgery that could present an unreasonable risk to the subject due to study treatment continuation, as determined by the Investigator The subject experiences a single or multiple severe laboratory abnormalities. Laboratory tests should be repeated for confirmation, within 48 to 72 hours from when the abnormality was first observed, when pragmatically possible.

The subject experiences an infection requiring parenteral treatment with antibiotic, antifungal, antiviral, antiparasitic, or antiprotozoal medications.

For an infection requiring oral treatment with antibiotic, antifungal, antiviral, antiparasitic, or antiprotozoal medications for longer than 2 weeks, interruption of IP is not required; however, the Investigator should determine if an interruption of dosing is in the best interest of the subject.

For local infections and recurrent infections, the investigator should determine the appropriate action related to the interruption of IP. Depending on the severity of the infection, the investigator should contact the Medical Monitor to determine if additional actions, such as discontinuation of IP would be in the best interest of the subject.

For subjects who develop suspected or confirmed symptomatic COVID-19 infection, or it is discovered that subjects have asymptomatic COVID-19 infection during the Treatment Period. IP should be temporary interrupted until the following conditions are met:

For symptomatic subjects:
  At least 10 days (20 days for severe/critical illness) have passed since symptoms first appeared or positive test result, and
  At least 24 hours have passed since last fever without the use of fever-reducing medications, and
  Symptoms (e.g., cough and shortness of breath) have resolved and
  In the opinion of the Investigator, there are no COVID-19 sequelae that may place the subject at a higher risk of receiving investigational treatment, and,
  Negative follow-up molecular test for COVID-19 based on institutional, local or regional guidelines and/or requirements For asymptomatic subjects:
  At least 7 days have passed since positive test result (based on date of collection, not date of test result availability).
  Negative follow-up molecular test for COVID-19 based on institutional, local or regional guidelines and/or requirements The decision to interrupt dosing of IP remains the responsibility of the treating physician. However, prior to interruption of dosing, the Investigator may contact the Medical Monitor. Once the laboratory abnormality stabilizes or the condition resolves, IP dosing may be resumed at the discretion of the Investigator, preferably at the next scheduled visit. The Medical Monitor may also be consulted to discuss the timing and appropriateness for the reintroduction of IP. If 3 or more consecutive doses are missed, the subject must be permanently discontinued from IP, as defined in Example 3.2.6.

3.2.6—Criteria for Discontinuation of Dosing

Dosing will be required to be permanently discontinued (treatment discontinuation) for a subject if the subject experiences any of the events listed below following initiation of IP.

SAE which is suspected of being related to IP, and study treatment continuation could present an unreasonable risk to the subject as determined by the Investigator, or Sponsor.
  Experiences any of the following severe laboratory abnormalities suspected of being related to IP. Laboratory tests should be repeated for confirmation prior to permanent IP discontinuation, within 48 to 72 hours from when the abnormality was first observed, or when pragmatically possible.
  Neutrophil count≤0.5×103/µL
  Platelet count ≤50×103/µL
  ALT and/or AST values >3×ULN with total bilirubin >2×ULN or INR>1.5, excluding confirmed Gilbert's Syndrome and therapeutic anticoagulation
  ALT and/or AST>5×ULN for greater than 2 weeks duration
  ALT or AST>8×ULN
  Experiences a severe or serious (per Investigator assessment) opportunistic infection (suggestive of subject being immunocompromised)
  Receives a malignancy diagnosis, excluding carcinoma in situ of the cervix or squamous or basal cell carcinoma of the skin if it can be successfully treated by local resection
  Experiences an anaphylactic reaction or other severe systemic reaction (e.g., hypersensitivity, allergic, or autoimmune) suspected of being related to IP by the Investigator or the Sponsor
  Experiences 2 separate occurrences of severe injection site reactions (ISR) that last longer than 24 hour.
  A severe ISR is defined as an ISR that manifests with symptoms causing severe discomfort/pain; symptoms requiring medical/surgical attention/intervention; interference with activities of daily life (ADLs) including inability to perform daily social and functional activities (e.g., absenteeism and/or bed rest); and/or when drug therapy is required
  Becomes pregnant
  Uses prohibited systemic immunosuppressive or immunomodulating drugs
  Uses systemic rescue therapy
  Misses 3 or more consecutive doses These subjects will be encouraged to remain in the study and complete all required study assessments (which the exception of dosing with IP) remaining in the treatment period and follow up period of the study. In order to prevent missing data, the site staff will ensure attempts are made to reach subjects by phone or email that do not maintain contact with the Investigator. Any subject discontinuing the study prematurely will be asked to complete the ET Visit and the Initial and the Final Follow-up Visits.

3.3—Packaging and Labelling

The label(s) for IP will include Sponsor name, address and telephone number, the protocol number, IP name, dosage form and strength (where applicable), amount of IP per container, lot number, expiry date (where applicable), medication identification/kit number, dosing instructions, storage conditions, and required caution statements and/or regulatory statements as applicable. Additional information may be included on the label as applicable per local regulations.

Cendakimab and placebo solutions differ slightly in physical appearance and when presented in vials, the slight color difference in IP cannot be fully blinded. Therefore, for the PFS a label cover on the active and placebo syringes (to be applied during packaging/labeling) will be used to maintain the blind.

3.4—Investigational Product Accountability and Disposal

Applicant (or designee) will review with the Investigator and relevant site personnel the process for IP return, disposal, and/or destruction including responsibilities for the site versus Applicant (or designee).

All supplies of IP and placebo will be accounted for in accordance with GCP. There will be an individual IP accountability record for each subject and the Investigator should maintain accurate records relating to IP supplies received during the study. These records should include the amount of and dates clinical drug supplies were received, dispensed and administered to the subject by the investigative site or by a home healthcare service, or returned by the designated investigative site staff or by a home healthcare service and returned to the Sponsor. If errors or damages in the clinical drug supply shipments occur, the Investigator should contact the IP supplier and the Study Monitor immediately. Copies of the IP accountability records will be provided by each Investigator for inclusion in the Trial Master File after database lock. The Study Monitor will periodically check the supplies of IP held by the Investigator or pharmacist to verify accountability of all IP used.

Applicant will provide IP only to the identified subjects of this study, according to the procedures described in this study protocol. After the end of the study, the Study Monitor will ensure that all unused IP and all medication containers, as applicable, can be destroyed on-site as long as proper documentation is supplied. If destruction on-site is not possible then any unused medication and containers, as applicable, will be returned to the Sponsor or designee. The Study Monitor will perform final accountability, package, seal and prepare for shipment. The clinical research organization (CRO) will verify that a final report of drug accountability is prepared and maintained in the Investigator Trial Master File.

3.5—Investigational Product Compliance

Applicant will ensure that the IP will be used only in accordance with the protocol and that subjects are correctly instructed on how to take their IP and that each subject is fully compliant with their assigned dosage regimen. Investigational product non-compliance is defined as taking less than 80% or more than 120% of IP doses during the entire study. Records of IP used and intervals between visits will be kept during the study. Drug accountability will be noted by the field monitor during site visits and at the completion of the study. The IP should be dispensed by the Investigator, or by a qualified individual under Applicant's supervision. An up-to-date treatment inventory/dispensing record must be maintained.

Example 4—Concomitant Medications and Procedures

All treatments (including prescription and over the counter [OTC] medications, herbal and dietary supplements, dietary modifications, and procedures) used by subjects within the 4 weeks (28 days) prior to the first Screening Visit or at any time during the study are regarded as prior or concomitant treatments and must be documented on the appropriate section of the eCRF. In addition, a history of previous treatments for AD will be documented.

All concomitant treatments, including blood and blood products, used from 28 days prior to the first Screening Visit until the Final Safety Follow-up Visit, or Final Study Visit must be reported on the eCRF.

4.1—Permitted Concomitant Medications and Procedures

The following concomitant medications are permitted during the study:

Oral antihistamines are permitted; however, the dose and regimen should remain stable from at least 2 weeks prior to the Day 1 (Baseline) Week 16, EOT/ET visit). Subjects should also refrain from dosing within 24 hours prior to a study visit.

Subjects may use inhaled corticosteroids, leukotriene receptor antagonists (e.g., montelukast), or mast cell stabilizers (e.g., cromolyn sodium) for indications other than AD, such as asthma, if on stable doses/regimens for at least 4 weeks prior to the first Screening Visit and regimens should remain stable throughout the treatment duration of the study. If one of these medications was recently discontinued, it must have been discontinued at least 4 weeks prior to the first Screening Visit.

Medically necessary dose adjustments (e.g. to treat unanticipated exacerbations, etc.) will be permitted; however, changes should consistent with local treatment guidelines. In addition, the Medical Monitor should be consulted to discuss the potential impact of the medication changes.

Ophthalmic corticosteroids are allowed for subjects receiving a stable dose to treat allergic conjunctivitis.

Unless prohibited, subjects may be administered any other medications necessary for the treatment of concurrent medical conditions or adverse events, as deemed necessary by the investigator. Following Day 1, addition of concomitant medications or any change in the dosage should be limited to those considered medically necessary.

4.2—Prohibited Concomitant Medications and Procedures

The introduction of medications or therapies for other medical conditions known to affect AD (e.g., systemic corticosteroids, mycophenolate-mofetil, interferon gamma (IFN-γ), Janus kinase inhibitors, biologic therapies, TCS (except when given for rescue therapy), TCI, cyclosporine, azathioprine, methotrexate, phototherapy, etc.) are not permitted during the study.

Additional details related to the concomitant medications and procedures that are prohibited throughout the duration of the study are initially identified in the exclusion criteria (Example 5.3) are summarized below.

Topical treatments that could affect the assessment AD (e.g., corticosteroids, calcineurin inhibitors, tars, antibiotic creams, topical antihistamines) within 7 days of the Day 1 visit, and throughout the duration of study.

Treatment with systemic antibiotics, antivirals, antiparasitics, antiprotozoals, or antifungals within 2 weeks prior to Day 1; however, during the study, use will be allowed to treat infection related adverse events.

Phototherapy narrowband UVB (NB-UVB) or broad band phototherapy within 4 weeks prior to the baseline visit, and throughout the duration of the study.

Systemic immunosuppressive or immunomodulating drugs (e.g. azathioprine, cyclosporine, systemic corticosteroids, IFN-γ, Janus kinase inhibitors, methotrexate, mycophenolate-mofetil, etc.) within 4 weeks prior to the Baseline visit, and throughout the duration of the study.

Treatment with immunomodulatory biologics as follows, and throughout the duration of the study:
Dupilumab within 3 months of Baseline visit.
Cell-depleting biologics, including to rituximab, within 6 months prior to the Baseline visit.
Other immunomodulatory biologics within 5 half-lives (if known) or 16 weeks prior to Baseline visit, whichever is longer With the exception of oral antihistamines, any additional medications and/or treatments that could affect AD are also prohibited throughout the study.

Due to the potential to affect AD with ultraviolet light exposure, subjects must also avoid prolonged exposure to the sun and not to use tanning booths, sun lamps or other ultraviolet light sources during the study.

Concurrent treatment with another IP, including through participation in an interventional trial for COVID-19 are prohibited throughout the duration of the study. Prospective subjects may not participate in a concurrent IP study or have received an IP within 5 drug half-lives prior to signing the ICF/assent for this study. Further, for subjects who received an investigational COVID-19 vaccine as part of a clinical trial prior to the first Screening Visit, enrollment must be delayed until the biologic impact of the vaccine is stabilized, as determined by discussion between the Investigator and the Clinical Trial Physician.

Live attenuated vaccines are prohibited within one month prior to the first Screening Visit, and throughout the duration of the study.

Unless a prohibited, subjects may be administered any other medications necessary for the treatment of concurrent medical conditions or adverse events, as deemed necessary by the investigator. Following Day 1, addition of concomitant medications or any change in the dosage should be limited to those considered medically necessary.

4.3—Required Concomitant Medications and Procedures

Non-medicated topical emollient should be applied twice daily for days prior to the Baseline/Day 1 visit and application (at the same twice daily frequency) should continue throughout the study. On study visit days, subjects must not moisturize or apply emollient before the visit. The last application emollient should be applied the night before the planned study visit. Non-medicated emollient is allowed after the visit is completed, and the same type of emollient should be used throughout the duration of the study.

4.4—Rescue Medication

In the event a subject develops intolerable AD symptoms that requires rescue therapy, exceptions related to prohibited medications, such as TCS use, will be permitted. The use of rescue therapy should be discouraged throughout the treatment phase of trial, and reserved for only severe symptoms associated with AD flares. In such cases, subjects may continue study participation, while continuing concomitant rescue therapy use; however, discontinuation of IP may be required depending on the type of rescue medication that is administered.

Subjects requiring rescue therapy should consider the addition of TCS prior to considering systemic treatment. Any subject who requires TCS rescue therapy treatment are encouraged to continue the TCS for as brief a period as possible (e.g. less than 7 days), while continuing with treatment with IP, and maintaining the study visit schedule.

Any subject requiring systemic rescue therapy to treat their AD during the treatment phase of the study will be discontinued from IP and will be encouraged to continue participation in the study without IP administration. Subjects who decline further participation in the study should proceed with the Early Termination Visit and follow up visit assessments. Subjects requiring systemic rescue therapy during the follow up period of the study should continue the study visits as planned. All instances of rescue therapy administration that occur during the course of study participation will be captured accordingly within the source documentation in the eCRF.

The impact of rescue therapy will also be evaluated by defining these endpoints as missing for subjects who initiate rescue therapy prior to Week 16 and analyzed according to methods described in Example 5.

Example 5—Statistical Considerations 5.1—Overview

This is a Phase 2, multicenter, global, randomized, double-blind, placebo-controlled, parallel-group study to evaluate the safety and efficacy of cendakimab in adult subjects with moderate to severe AD. Subjects will be randomized to receive study medication for 16 weeks and the randomization will be stratified by geographic region (Japan versus rest of world) and, within RoW region only, randomization will also be stratified by disease severity based on baseline v-IGA-AD score (3 [moderate] or 4 [severe]). An independent DMC will be used to review the safety data regularly during the course of the study.

5.2—Study Population Definitions

The following analysis populations will be used in the statistical analysis:

Modified intent-to-treat (mITT) Population

All randomized participants who received at least 1 dose of investigational product (IP).

The mITT population will be used as the primary population for all efficacy parameters. Subjects who prematurely withdraw from the trial for any reason and for whom an assessment is not performed for any reason will still be included in the mITT population. Subjects will be included in the treatment group to which they are randomized. Subjects who were randomized with a misreported stratum will be classified according to their original (misreported) stratum.

Safety Population

The Safety population will consist of all subjects who received at least one dose of IP. This population will be used for all summaries of safety data. Subjects randomized to placebo who receive any dose of cendakimab will be summarized in the cendakimab group. Subjects randomized to cendakimab who receive only placebo will be summarized in the placebo group; otherwise, they will be summarized in the cendakimab group.

Pharmacokinetic Population

All subjects who received at least one dose of active drug and have at least one measurable concentration data.

Biomarkers

All participants that received any study treatment and have any available biomarker measurement.

5.3—Sample Size and Power Considerations

Approximately 200 subjects will be randomized in this Phase 2 dose ranging study. Randomization will be equal among the four dose groups of placebo, 300 mg Q2W, 720 mg Q2W, and 720 mg QW (approximately 50 subjects per group). Assuming a 10% dropout rate, a sample size of 45 subjects per group will provide approximately 90% power to detect a treatment difference relative to placebo (difference in means) of 35% with respect to the primary endpoint of percentage change from baseline in EASI scores at Week 16. In these power calculations superiority over placebo for a particular dose group is met if the lower bound of the (2-sided) 95% confidence interval (z-score) for the treatment difference exceeds zero (adjusted for multiplicity).

The sample size calculations are based on the following considerations for comparing mean percentage changes from baseline in EASI scores at Week 16 versus placebo. In particular, the recent Phase 2b study of dupilumab reported an observed mean for placebo of 18.1% and corresponding treatment differences of 50.1% (standard error [SE=6.7%]) and 55.7% (SE=6.7%), for the doses of 300 mg Q2W, and 300 mg QW, respectively (Thagi, 2016). This study evaluating cendakimab is designed to detect a (true) treatment difference relative to placebo of 35%. Applicant assumes a (true) mean of 20% for placebo, and means for the active dose groups corresponding to treatment differences of 25% (300 mg Q2W), 30% (720 mg Q2W), and 35% (720 mg QW), with a common standard deviation (SD) of 50%. Applicant notes that the common SD assumption of 50% for the percentage change from baseline in EASI scores at Week 16 was also assumed in the dupilumab Phase 2b study design (Thagi et al., Lancet 387:40-52 (2016)). Under these assumptions, it is estimated that with a sample size of forty-five subjects per group the study provides approximately 90% power to detect superiority relative to placebo for at least one dose at the overall type-1 error of $\alpha=0.05$ (two-sided) using a hierarchical testing approach (In the order of 720 mg QW vs placebo, 720 mg Q2W vs placebo, and 300 mg Q2W vs placebo).

In addition, the study will provide more than 90% power to detect superiority relative to placebo for at least one dose with respect to the key secondary endpoint of IGA response (0—clear, 1—almost clear) at Week 16 assuming true proportions of 2% (placebo), 15% (300 mg Q2W), 25% (720 mg Q2W), and 25% (720 mg QW). Applicant notes that the Phase 2 dupilumab study reported proportions of 30% and 33% for the doses of 300 mg Q2W, and 300 mg QW, respectively (Thagi et al. (2016)). The hierarchical testing approach used for the primary endpoint was utilized to maintain the overall type-1 error of $\alpha=0.05$ (two-sided) with respect to the IGA response endpoint. However, multiplicity adjustments are not implemented across endpoints jointly (e.g., for both the primary and key secondary endpoints simultaneously).

5.4—Background and Demographic Characteristics

Summaries for the demographics, baseline characteristics, medical history, prior medications, and protocol deviations will be presented for the mITT population by treatment groups. Concomitant medications will be presented for the Safety population by treatment groups. Individual listings will also be provided, including concomitant medical procedures for the Safety population.

5.5—Subject Disposition

The disposition of subjects will be summarized with numbers and percentages by treatment group for all enrolled subjects. Summaries will include the number and percentage of subjects in the following categories:

Randomized, dosed (at least one dose of study treatment), permanently discontinued from IP, discontinued from the study, discontinued from IP and remained in study follow up, and completed study Primary reasons for discontinuation from the study 5.6—Efficacy Analysis 5.6.1—Percentage Change from Baseline in EASI Scores at Week 16

The primary efficacy endpoint of percentage change from baseline in EASI scores at Week 16 will be analyzed using an analysis of covariance (ANCOVA) model, based on the modified intent to treat (mITT) population, with treatment group indicators as the main effects adjusting for baseline EASI scores, and the stratification factors of vIGA-AD score (3 [moderate] or 4 [severe]) and region (Japan vs RoW) as covariates. For each of the active treatment arms, the adjusted mean percentage changes from baseline and corresponding differences versus placebo in EASI scores at Week 16 will be estimated (based on Least-Squares Means) along with 95% Wald confidence intervals (CIs) and p-values.

Missing EASI scores at Week 16 (e.g., due to study dropout or other reasons for lack of assessment) will be handled using a multiple imputation (MI) approach (Berglund, SAS Institute, Paper 2018-2015) under a missing at random (MAR) assumption. In the sequel, Applicant refers to this as the MI approach.

To adjust for multiplicity, a standard hierarchical approach will be utilized by conducting comparisons, each at the 2-sided 0.05 alpha-level (based on the aforementioned adjusted p-values), in the order of 720 mg QW vs placebo, 720 mg Q2W vs placebo, and 360 mg Q2W vs placebo.

Sensitivity analyses will be conducted to support the primary analysis by utilizing an alternative missing data approach as well as by assessing the impact of rescue therapy. The first sensitivity analysis will replace the MI approach for missing EASI scores at Week 16 with imputation by LOCF (last observation carried forward). The impact of rescue therapy will be evaluated by defining EASI scores after rescue therapy (prior to Week 16) initiation as missing. The second sensitivity analysis will apply the MI approach with the addition (further degree) of missingness due to rescue. The third sensitivity analysis will combine the first and second sensitivity analyses by replacing the MI approach in the second sensitivity analysis with LOCF.

5.6.2—Subgroup Analysis of Primary Endpoint

To assess whether the treatment effect is consistent across various groups, subgroup analyses will be performed for the primary endpoint at Week 16. Treatment differences and 2-sided 95% CIs will be provided for each subgroup listed below.

Forest plots for the treatment differences by subgroup will also be provided.

1. Non-elderly adults [<65 years] versus elderly adults [≥65 years])
2. vIGA-AD baseline score (4 versus 3)
3. Sex (female versus male)
4. Region (Rest of world versus Japan)
5. Race (white versus non-white)
6. Prior experience with systemic immunosuppressive drugs If there are not enough subjects (e.g., <8% mITT population, based on observed cases) in each subgroup and treatment category, the corresponding subgroup analyses will not be performed; instead, summary statistics will be provided.

5.6.3—Analysis Methods

For the first key secondary endpoint of proportion of subjects with both a vIGA-AD score of 0 (clear) or 1 (almost clear) and a reduction of 2 or more points in v-IGA-AD score from baseline at Week 16 will be analyzed based on the mITT population using a stratified CMH test at a two-sided 5% significance level. The randomization stratification levels are: (1) Japan region, (2) RoW region and vIGA-AD score 3, and (3) RoW region and vIGA-AD score 4. Estimates of the differences in proportions between each treatment group versus placebo, and associated 95% confidence intervals will be provided along with p-values. Missing endpoint values (e.g., due to study dropout or other reasons for lack of assessment) will be imputed as non-responders. A sensitivity analysis will be conducted based on defining subjects who initiate rescue therapy (prior to Week 16) as missing and treated as non-responders.

The second key secondary endpoint of proportion of subjects with a 75% improvement from baseline in EASI (EASI-75) at Week 16 will be analyzed in the same manner as above.

The hierarchical testing approach used for the primary endpoint will be utilized to adjust for multiplicity with respect to the 3 active doses for each of these key secondary endpoints. However, multiplicity adjustments are not implemented across the primary and two key secondary endpoints simultaneously.

The following endpoints will be analyzed in the same manner as the key secondary endpoints, excepting that p-values will not be provided:

The secondary endpoint of proportion of subjects with Pruritus NRS change of ≥4 from Baseline at Week 16

The secondary endpoint of proportion of subjects with a 90% improvement from Baseline in EASI (EASI-90) at Week 16

The following endpoints will be analyzed in the same manner as the primary endpoint, excepting that p-values will not be provided:

The secondary endpoint of percentage change from baseline in Pruritus NRS at Week 16

The secondary endpoint of percent change in SCORAD Scores from Baseline at Week 16

The secondary endpoint of mean percent change in Body Surface Area (BSA) involved with AD from Baseline at Week 16

For the secondary endpoint of time to achieve at least 4 points of improvement in the severity of pruritus NRS scale in the first 16 weeks of treatment, the distribution of times to the first event of 4-point improvement will be compared based on Kaplan-Meier (K-M) and log-rank approaches. Comparisons versus placebo, for each dose group separately, will be based on a stratified log-rank test with associated p-value provided. The stratification levels are: (1) Japan region, (2) RoW region and IGA score 3, and (3) RoW region and vIGA-AD score 4. The K-M estimates for the cumulative proportions of subjects achieving a 4-point improvement, by specific timepoints, will be provided by dose group as well as differences with placebo and associated 95% confidence intervals. These will be reported at various timepoints (e.g. Day 1 to 28, followed by weekly assessments).

5.7—Safety Analysis

All analyses of safety data will be conducted using the Safety population by treatment for the entire study duration of 32 weeks. The assessment of safety will include AEs, SAEs, AEs leading to discontinuation of study treatment, and AEs leading to discontinuation from the study; changes from baseline in laboratory values and vital signs; and incidence and type of laboratory, vital signs, and physical examination abnormalities. Individual data listings will also be provided.

Adverse events will be monitored during the trial, and the data will be summarized by worst severity grade. Adverse events, with focus on treatment-emergent AEs, will be summarized by MedDRA system organ class, and preferred term. Investigational product-related adverse events, adverse events leading to death or to discontinuation from treatment, events assessed as Moderate or Severe, IP-related events, and serious adverse events, and events of interest.

Laboratory assessments will be performed by a central laboratory. All summaries will be based on the Standard International System of Units (SI) provided by the central lab. Each subject's hematology, blood chemistry, and urinalysis values will be flagged as "low", "normal", or "high" relative to the normal ranges of the central laboratory.

Summary statistics of actual values and changes from baseline in vital signs will be provided by visit.

5.8—Other Topics 5.8.1—Analysis of Exploratory Endpoints

Exploratory efficacy endpoints will be summarized using descriptive statistics by treatment group. For continuous endpoints, number of subjects (n), mean, SD, SE, median, minimum, and maximum will be provided. Binary endpoints will be summarized by number and percentages.

5.8.2—Pharmacokinetics, Pharmacodynamics, and Exposure-Response

Serum trough concentrations (Ctrough) of cendakimab will be summarized with descriptive statistics by treatment and visit. Additional analysis may be conducted as appropriate (e.g., by ADA status).

Population PK analysis will be performed using nonlinear mixed-effects modeling to characterize the population PK of cendakimab and to identify key covariate effects (e.g., immunogenicity, intrinsic and extrinsic factors). Data from other studies may be included if appropriate. Exposure-response and pharmacodynamic relationships will be conducted for efficacy, safety, and biomarker endpoints. Details on the studies and methodology will be outlined in a separate PK Analysis Plan, and results will be issued separately from the clinical study report as a stand-alone report.

5.8.3—Data Monitoring Committee

Additional safety monitoring will be performed by an external, independent Data Monitoring Committee (DMC). A DMC will be convened that will include physicians with experience in treating subjects with type 2 inflammatory diseases, as well as a statistician, all of whom are not otherwise involved in the study conduct and for whom there is no identified conflict of interest.

During the study, the DMC will review selected data (to be specified in the DMC charter) on a regular basis for the assessment of benefit-risk and determination of study continuation. An independent third party will prepare the reports of aggregate data summaries and individual subject data listings, as appropriate, for the DMC members for each scheduled meeting. Operational details for the DMC, including a blinding plan to assure that all personnel involved in the conduct of the study remain blinded to the results of data reviews, will also be described in the DMC charter. The DMC will function in advisory capacity, making recommendations based on their independent assessment of the safety data. Unblinded safety data may be reviewed on a periodic or ad-hoc basis by the DMC, as needed, to further enhance the ongoing assessment of the risk/benefit of the IP.

Example 6—Adverse Events 6.1—Monitoring, Recording, and Reporting of Adverse Events An AE is any noxious, unintended, or untoward medical occurrence that may appear or worsen in a subject during the course of a study. It may be a new intercurrent illness, a worsening concomitant illness, an injury, or any concomitant impairment of the subject's health, including laboratory test values (as specified by the criteria in Example 6.3), regardless of etiology. Any worsening (i.e., any clinically significant adverse change in the frequency or intensity of a pre-existing condition) should be considered an AE. A diagnosis or syndrome should be recorded on the AE page of the CRF rather than the individual signs or symptoms of the diagnosis or syndrome.

Abuse, withdrawal, sensitivity or toxicity to an investigational product should be reported as an AE. Overdose, accidental or intentional, whether or not it is associated with an AE should be reported on the overdose CRF (see Example 3.2 for the definition of overdose). Any sequela of an accidental or intentional overdose of an investigational product which meets the definition of an adverse event, should be reported as an AE on the CRF. If the sequela of an overdose meets serious criteria, then it must be marked as serious on the CRF. The overdose itself should not be reported as an AE.

In the event of overdose, the subject should be monitored as appropriate and should receive supportive measures as necessary. There is no known specific antidote for cendakimab overdose. Actual treatment should depend on the severity of the clinical situation and the judgment and experience of the treating physician.

All subjects will be monitored for AEs during the study. Assessments may include monitoring of any or all of the following parameters: the subject's clinical symptoms, laboratory, pathological, radiological or surgical findings, physical examination findings, or findings from other tests and/or procedures.

All AEs will be recorded by the Investigator from the time the subject signs informed consent until 16 weeks after the last dose of IP, or the last Follow Up visit, whichever is longer, as well as those SAEs made known to the Investigator at any time thereafter that are suspected of being related to IP. All adverse events (serious/non-serious) will be recorded on the CRF and in the subject's source documents. Refer to Example 6.5 for instructions on how to report SAEs to Drug Safety.

6.2—Evaluation of Adverse Events

A qualified Investigator will evaluate all adverse events as to:

6.2.1—Seriousness

An SAE is any AE occurring at any dose that:
Results in death;
Is life-threatening (i.e., in the opinion of the Investigator, the subject is at immediate risk of death from the AE);
Requires inpatient hospitalization or prolongation of existing hospitalization (hospitalization is defined as an inpatient admission, regardless of length of stay);
Results in persistent or significant disability/incapacity (a substantial disruption of the subject's ability to conduct normal life functions);
Is a congenital anomaly/birth defect;
Constitutes an important medical event.

Important medical events are defined as those occurrences that may not be immediately life-threatening or result in death, hospitalization, or disability, but may jeopardize the subject or require medical or surgical intervention to prevent one of the other outcomes listed above. Medical and scientific judgment should be exercised in deciding whether such an AE should be considered serious.

Events not considered to be SAEs are hospitalizations for:
a procedure that is planned (i.e., planned prior to start of treatment on study); must be documented in the source document and the CRF. Hospitalization or prolonged hospitalization for a complication remains a reportable SAE.
an elective treatment of or an elective procedure for a pre-existing condition, unrelated to the studied indication, that has not worsened from baseline.
emergency outpatient treatment or observation that does not result in admission, unless fulfilling other seriousness criteria above.

For each AE, the Investigator will provide information on severity, start and stop dates, relationship to the IP, action taken regarding the IP, and outcome.

6.2.2—Severity/Intensity

For each AE, the Investigator must assess the severity/intensity of the event.

The following grading scale should be used to evaluate severity/intensity:
Mild
Asymptomatic or mild symptoms; clinical or diagnostic observations only
Intervention not indicated
Activities of daily life (ADLs) minimally or not affected
No or minimal intervention/therapy may be required
Moderate
Symptom(s) cause moderate discomfort
Local or noninvasive intervention indicated
More than minimal interference with ADLs but able to carry out daily social and functional activities.
Drug therapy may be required
Severe (could be non-serious or serious)
Symptoms causing severe discomfort/pain
Symptoms requiring medical/surgical attention/intervention
Interference with ADLs including inability to perform daily social and functional activities (e.g., absenteeism and/or bed rest)
Drug therapy is required The term "severe" is often used to describe the intensity of a specific event (as in mild, moderate or severe myocardial infarction); the event itself, however, may be of relatively minor medical significance (such as severe headache). This criterion is not the same as "serious" which is based on subject/event outcome or action criteria associated with events that pose a threat to a subject's life or functioning.

Seriousness, not severity, serves as a guide for defining regulatory obligations.

6.2.3—Causality

Applicant will determine the relationship between the administration of the IP and the occurrence of an AE as Not Suspected or Suspected as defined below:
Not suspected: a causal relationship of the adverse event to IP administration is unlikely or remote, or other medications, therapeutic interventions, or underlying conditions provide a sufficient explanation for the observed event.
Suspected: there is a reasonable possibility that the administration of IP caused the adverse event. 'Reasonable possibility' means there is evidence to suggest a causal relationship between the IP and the adverse event.

Causality should be assessed and provided for each AE based on currently available information. Causality is to be reassessed and provided as additional information becomes available.

6.2.4—Duration

For each AE, Applicant will provide a record of the start and stop dates of the event.

6.2.5—Action Taken

Applicant will report the action taken with IP as a result of each AE, as applicable (e.g., discontinuation, interruption, or dose reduction of IP, as appropriate) and report if concomitant and/or additional treatments were given for the event.

6.2.6—Outcome

Applicant will report the outcome of the event for each AE.

All SAEs that have not resolved upon discontinuation of the subject's participation in the study must be followed until recovered (returned to baseline), recovered with sequelae, or death (due to the SAE).

6.3—Abnormal Laboratory Values

An abnormal laboratory value is considered to be an AE if the abnormality:
results in discontinuation from the study;
requires treatment, modification/interruption of IP dose, or any other therapeutic intervention; or is judged to be of significant clinical importance, e.g., one that indicates a new disease process and/or organ toxicity or is an exacerbation or worsening of an existing condition.

Regardless of severity grade, only laboratory abnormalities that fulfill a seriousness criterion need to be documented as a serious adverse event.

If a laboratory abnormality is one component of a diagnosis or syndrome, then only the diagnosis or syndrome should be recorded as the AE. If the abnormality was not a part of a diagnosis or syndrome, then the laboratory abnormality should be recorded as the AE. If possible, the laboratory abnormality should be recorded as a medical term and not simply as an abnormal laboratory result (e.g., record thrombocytopenia rather than decreased platelets).

6.4—Pregnancy

All pregnancies or suspected pregnancies occurring in either a female subject of childbearing potential or partner of childbearing potential of a male subject are immediately reportable events.

6.5—Females of Childbearing Potential

Pregnancies and suspected pregnancies (including elevated β-hCG or positive pregnancy test in a female subject of childbearing potential regardless of disease state) occurring while the subject is on IP, or within or within 5 months of the subject's last dose of IP are considered immediately reportable events. Investigational product is to be discontinued immediately. The pregnancy, suspected pregnancy, or positive pregnancy test must be reported to Applicant's Drug Safety immediately by email, phone or facsimile, or other appropriate method, using the Pregnancy Initial Report Form, or approved equivalent form.

The female subject may be referred to an obstetrician-gynecologist or another appropriate healthcare professional for further evaluation.

Applicant will follow the female subject until completion of the pregnancy and must notify Applicant Drug Safety immediately about the outcome of the pregnancy (either normal or abnormal outcome) using the Pregnancy Follow-up Report Form or approved equivalent form.

If the outcome of the pregnancy was abnormal (e.g., spontaneous abortion), Applicant will report the abnormal outcome as an AE. If the abnormal outcome meets any of the serious criteria, it must be reported as an SAE to Applicant Drug Safety within 24 hours of Applicant's knowledge of the event.

All neonatal deaths that occur within 28 days of birth should be reported, without regard to causality, as an SAE. In addition, any infant death after 28 days that the Investigator suspects is related to the in utero exposure to the IP should also be reported as an SAE.

6.5—Reporting of Serious Adverse Events

Any AE that meets any serious criterion requires reporting as an SAE within 24 hours of the Investigator's knowledge of the event. This instruction pertains to initial SAE reports as well as any follow-up reports.

This requirement applies to all SAEs (regardless of relationship to IP) that occur during the study (from the time the subject signs informed consent until 16 weeks after the last dose of IP, or the last Follow Up Visit, whichever is longer) or any SAE made known to the Investigator at any time thereafter that are suspected of being related to IP. Serious adverse events occurring prior to treatment (after signing the ICF) are to be recorded within the CRF, but do not require reporting to Applicant Drug Safety.

Where required by local legislation, Applicant is responsible for informing the Institutional Review Board/Ethics Committee (IRB/EC) of the SAE and providing them with all relevant initial and follow-up information about the event. Applicant keep copies of all SAE information on file including correspondence with Applicant and the IRB/EC.

The SAE is recorded within the CRF, and the data is transmitted electronically to Applicant Drug Safety. In the event electronic transmission is not available, a paper SAE Report Form will be completed and sent directly to Applicant Drug Safety, ensuring the event is recorded on the CRF as well.

6.6—Adverse Events of Special Interest

Although the risk for serious infections is expected to be low in this Phase 2 study, Adverse Events of special interest (AESI) have identified to provide further safety monitoring guidance to the investigators. AESIs fall into a number of categories based on the safety observations from dupilumab, lebrikizumab, other cendakimab clinical studies and the potential pharmacologic effects of IL-4 receptor antagonist and anti-IL-13 antibodies. Applicant will identify AEs that meet the following criteria for adverse events of special interest (AESIs). All AESIs must be reported within 24 hours of the Applicant's knowledge of the event. These include the following:

Anaphylactic reactions

Systemic or severe hypersensitivity reactions

Severe injection site reactions (ISR) that last longer than 24 hours

A severe ISR is defined as an ISR that manifests with symptoms causing severe discomfort/pain; symptoms requiring medical/surgical attention/intervention; interference with ADLs including inability to perform daily social and functional activities (e.g., absenteeism and/or bed rest); and/or when drug therapy is required Malignancies except in situ carcinoma of the cervix or non-metastatic squamous cell or basal cell carcinoma of the skin Helminthic or parasitic infections Opportunistic infections Any severe infections; or infections requiring treatment with parenteral antibiotic, antiviral, or antifungal medications; or infections requiring treatment with oral antibiotic, antiviral, or antifungal medications for longer than 2 weeks 6.7—Expedited Reporting of Adverse Events For the purpose of regulatory reporting, Applicant Drug Safety will determine the expectedness of events suspected of being related to cendakimab based on the Investigator Brochure.

Example 7—Discontinuations 7.1—Treatment Discontinuation

The following events are considered sufficient reasons for permanently discontinuing a subject from the IP:

Adverse event

Physician decision

Lack of efficacy

Protocol deviation

Withdrawal by subject

Death

Lost to follow-up

Non-compliance with IP

Other (to be specified on the eCRF)

Subjects who are permanently discontinued from IP will be encouraged to continue participation in the study without IP administration in order to complete all remaining required study assessments including efficacy evaluations. Subjects who decline further participation in the study should complete the early termination visit, and follow up visit assessments.

The reason for discontinuation of treatment should be recorded in the CRF and in the source documents.

The decision to discontinue a subject from treatment remains the responsibility of the treating physician, which will not be delayed or refused by the Sponsor. However, prior to discontinuing a subject, the Investigator may contact the Medical Monitor and forward appropriate supporting documents for review and discussion.

7.2—Study Discontinuation

The following events are considered sufficient reasons for discontinuing a subject from the study:
Screen failure
Adverse event
Physician decision
Withdrawal by subject
Death
Lost to follow-up
Other (to be specified on the eCRF)

The reason for study discontinuation should be recorded in the eCRF and in the source documents. Because follow-up of subjects who discontinue from the study prematurely is of particular importance, every attempt should be made to collect all or specific final data on a discontinued subject.

---

We claim:

1. A method of treating atopic dermatitis comprising administering to a subject in need thereof a therapeutically effective amount of an anti-IL-13 antibody, or antigen binding fragment thereof, thereby treating atopic dermatitis in the subject, wherein the anti-IL-13 antibody comprises an antigen binding domain comprising six CDRs: CDR-H1, CDR-H2, CDR-H3, CDR-L1, CDR-L2, and CDR-L3, wherein:
   (a) CDR-H1 comprises residues 31-37 of SEQ ID NO:2;
   (b) CDR-H2 comprises residues 52-67 of SEQ ID NO:2;
   (c) CDR-H3 comprises residues 100-112 of SEQ ID NO:2;
   (d) CDR-L1 comprises residues 24-34 of SEQ ID NO:3;
   (e) CDR-L2 comprises residues 50-56 of SEQ ID NO:3; and
   (f) CDR-L3 comprises residues 89-97 of SEQ ID NO:3.

2. The method of claim 1, wherein the anti-IL-13 antibody comprises a heavy chain variable domain comprising the amino acid sequence of SEQ ID NO:2.

3. The method of claim 1, wherein the anti-IL-13 antibody comprises a light chain variable domain comprising the amino acid sequence of SEQ ID NO:3.

4. The method of claim 1, wherein the anti-IL-13 antibody comprises a heavy chain variable domain comprising the amino acid sequence of SEQ ID NO:2 and a light chain variable domain comprising the amino acid sequence of SEQ ID NO:3.

5. The method of claim 1, wherein the anti-IL-13 antibody comprises an L240A mutation at position 117 of SEQ ID NO:4.

6. The method of claim 1, wherein the anti-IL-13 antibody comprises an L241A mutation at position 118 of SEQ ID NO:4.

7. The method of claim 1, wherein the anti-IL-13 antibody comprises an L240A mutation at position 117 of SEQ ID NO:4 and L241A mutation at position 118 of SEQ ID NO:4.

8. The method of claim 7, wherein the anti-IL-13 antibody is cendakimab.

9. The method of claim 1, wherein the anti-IL-13 antibody is administered subcutaneously.

* * * * *

SEQUENCE LISTING

```
<160> NUMBER OF SEQ ID NOS: 7

<210> SEQ ID NO 1
<211> LENGTH: 132
<212> TYPE: PRT
<213> ORGANISM: Homo sapiens

<400> SEQUENCE: 1

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130

<210> SEQ ID NO 2
<211> LENGTH: 123
<212> TYPE: PRT
<213> ORGANISM: Artificial Sequence
<220> FEATURE:
<223> OTHER INFORMATION: Synthetic

<400> SEQUENCE: 2

Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30

Asp Met Gly Val Asp Trp Ile Arg Gln Pro Pro Gly Lys Gly Leu Glu
        35                  40                  45

Trp Leu Ala His Ile Trp Trp Asp Asp Val Lys Arg Tyr Asn Pro Ala
    50                  55                  60
```

```
Leu Lys Ser Arg Leu Thr Ile Ser Lys Asp Thr Ser Lys Asn Gln Val
 65                  70                  75                  80

Val Leu Lys Leu Thr Ser Val Asp Pro Val Asp Thr Ala Thr Tyr Tyr
                 85                  90                  95

Cys Ala Arg Thr Val Ser Ser Gly Tyr Ile Tyr Tyr Ala Met Asp Tyr
            100                 105                 110

Trp Gly Gln Gly Thr Leu Val Thr Val Ser Ser
            115                 120
```

<210> SEQ ID NO 3
<211> LENGTH: 107
<212> TYPE: PRT
<213> ORGANISM: Artificial Sequence
<220> FEATURE:
<223> OTHER INFORMATION: Synthetic

<400> SEQUENCE: 3

```
Asp Ile Gln Met Thr Gln Ser Pro Ser Ser Leu Ser Ala Ser Val Gly
  1               5                  10                  15

Asp Arg Val Thr Ile Ser Cys Arg Ala Ser Gln Asp Ile Arg Asn Tyr
                 20                  25                  30

Leu Asn Trp Tyr Gln Gln Lys Pro Gly Lys Ala Pro Lys Leu Leu Ile
             35                  40                  45

Phe Tyr Thr Ser Lys Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Tyr Cys Gln Gln Gly Asn Thr Leu Pro Leu
                 85                  90                  95

Thr Phe Gly Gly Gly Thr Lys Val Glu Ile Lys
            100                 105
```

<210> SEQ ID NO 4
<211> LENGTH: 330
<212> TYPE: PRT
<213> ORGANISM: Homo sapiens

<400> SEQUENCE: 4

```
Ala Ser Thr Lys Gly Pro Ser Val Phe Phe Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
```

-continued

```
        145                 150                 155                 160
Tyr Val Asp Gly Val Glu Val His Asn Ala Lys Thr Lys Pro Arg Glu
                    165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 5
<211> LENGTH: 330
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 106
<212> TYPE: PRT
<213> ORGANISM: Homo sapiens

<400> SEQUENCE: 6

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 7
<211> LENGTH: 105
<212> TYPE: PRT
<213> ORGANISM: Homo sapiens

<400> SEQUENCE: 7

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80
```

```
His Arg Ser Tyr Ser Cys Gln Val Thr His Glu Gly Ser Thr Val Glu
                85                  90                  95
Lys Thr Val Ala Pro Thr Glu Cys Ser
            100             105
```